US008741611B2

(12) United States Patent
Brown et al.

(10) Patent No.: US 8,741,611 B2
(45) Date of Patent: Jun. 3, 2014

(54) METHODS FOR IMPROVING MALIC ACID PRODUCTION IN FILAMENTOUS FUNGI

(75) Inventors: Stephen Brown, Davis, CA (US); Sheryl Luttringer, Loomis, CA (US); Debbie Yaver, Davis, CA (US); Alan Berry, Granite Bay, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 12/870,523

(22) Filed: Aug. 27, 2010

(65) Prior Publication Data

US 2011/0053233 A1    Mar. 3, 2011

Related U.S. Application Data

(60) Provisional application No. 61/238,962, filed on Sep. 1, 2009, provisional application No. 61/327,224, filed on Apr. 23, 2010, provisional application No. 61/356,971, filed on Jun. 21, 2010.

(51) Int. Cl.
    *C12P 7/46* (2006.01)
    *C12N 1/00* (2006.01)

(52) U.S. Cl.
    USPC ........................................ 435/145; 435/254.3

(58) Field of Classification Search
    None
    See application file for complete search history.

(56) References Cited

U.S. PATENT DOCUMENTS

| 3,063,910 A | 11/1962 | Abe et al. | |
|---|---|---|---|
| 5,536,661 A * | 7/1996 | Boel et al. | 435/254.3 |
| 7,504,490 B1 | 3/2009 | Weinstock et al. | |

FOREIGN PATENT DOCUMENTS

| EP | 2471943 A1 | 7/2010 |
|---|---|---|
| WO | WO2007061590 | 5/2007 |
| WO | WO 2008/144626 | 11/2008 |
| WO | WO2009011974 | 1/2009 |
| WO | WO 2009/065778 | 5/2009 |
| WO | WO2009/155382 | 12/2009 |
| WO | WO2010003728 | 1/2010 |
| WO | WO2010111344 | 9/2010 |
| WO | 2011024583 A1 | 3/2011 |
| WO | 2011066304 A2 | 6/2011 |

OTHER PUBLICATIONS

Accession # Q2USG3. Uniprot/TrEMBL database Jan. 24, 2006.*
Accession # Q2UGL1. Uniprot/TrEMBL database Jan. 24, 2006.*
Argyrou et al. The Plant Cell, vol. 13, 953-964, Apr. 2001.*
Grobler et al., The mael Gene of *Schizosaccharomyces pombe* Encodes a Permease for Malate and other C₄, Dicarboxylic Acids, 1995, *Yeast* 11, 1485-1491.
Sauer et al., Microbial production of organic acids: expanding the markets, 2008, *Trends in Biotechnology* 26, 100-108.
Zelle et al., Malic Acid Production by *Saccharomyces cerevisiae*: Engineering of Pyruvate Carboxylation, Oxaloacetate Reduction, and Malate Export, 2008, *Appl. Environ. Microbiol.* 74, 2766-2777.
Bercovitz et al., Localization of Pyruvate Carboxylase in Organic Acid-Producing *Aspergillus* Strains, 1990, *Appl. Environ. Microbiol.* 56, 1594-1597.
Battat et al. Optimization of L-Malic Acid Production by *Aspergillus flavus* in a Stirred Fermentor, 1991, *Biotechnol. Bioengineering* 37, 1108-1116.
Bauer et al., By-product formation during exposure of respiring *Saccharomyces cerevisiae* cultures to excess glucose is not caused by a limited capacity of pyruvate carboxylase, 1999, *FEMS Microbiol Lett.* 179, 107-113.
Pines et al., Overexpression of cytosolic malate dehydrogenase (MDH2) causes overproduction of specific organic acids in *Saccharomyces cerevisiae*, 1997, *Appl. Microbiol. Biotechnol.* 48, 248-255.
Peleg et al., Malic acid accumulation by *Aspergillus flavus*,1988, *Appl. Microbiol. Biotechnol.* 28, 69-75.
Camarasa et al., Characterization of *Schizosaccharomyces pombe* Malate Permease by Expression in *Saccharomyces cerevisiae*, Applied and Environmental Microbiology, Sep. 2001, p. 4144-4151.
Fedorova et al., Genomic Islands in the Pathogenic Filamentous Fungus *Aspergillus fumigates*, PLoS Genetics, Apr. 2008, vol. 4, Issue 4, 1-13.
Nierman, 2005, Nature 438 (22), p. 1151-1156, 2005.
Birren et al, 2008—UniProt Accession No. B6JXU3.
Elleuche, 2009, Curr Genet 55, 211-222.
Fedorova et al, 2007—Uniprot Access No. A1C406.
Goldberg et al, 2006, J Chem Technol Biotechnol 81 (10), 1601-1611.
Nielsen and Jewett, 2008, FEMS Yeast Res 8, 122-131.
Nierman et al, 2005—Uniprot Acces No. Q4WCF3.
Bush et al., Geneseq EBI Access No. AWP70496, 2010.
Winkler et al, Geneseq EBI Access No. ATT44026, 2009.
Nevoigt, 2008, Microbiol Mol Biol Revs 72(3), 379-412.
Ludwig et al, 1998, Plant Physiol 117 (3), 1071-1081.
WO 2011-024583—Eng Equiv—EP 2 471 943.
Zelle, Rintze Meindert. Metabolic engineering of *Saccharomyces cerevisiae* for C4-dicarboxylic acid production. PhD Thesis. Delft Univerisy of Technology, Delft, 2011.
Lubertozzi et al, 2008, Biotechnol Advances 27, 53-75.
Whisstock et al 2003 Qtr Rev Biophys 36(3) 307-340.

* cited by examiner

*Primary Examiner* — Oluwatosin Ogunbiyi
(74) *Attorney, Agent, or Firm* — Eric J. Fechter

(57) ABSTRACT

The present invention relates to methods of producing a C4 dicarboxylic acid, comprising: (a) cultivating a filamentous fungal host cell comprising a polynucleotide selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase; wherein the filamentous fungal host cell is capable of secreting increased levels of the C4 dicarboxylic acid compared to the filamentous fungal host cell without the heterologous polynucleotide when cultivated under the same conditions; and (b) recovering the C4 dicarboxylic acid. The present invention also relates to methods for increasing C4 dicarboxylic acid production, filamentous fungal host cells and malate dehydrogenase variants.

31 Claims, 18 Drawing Sheets

```
         M   L   T   P     P   K   F     E   D   E     K   Q   L   G     P   V   G     I   R   E
   1 ATGCTCACAC CTCCCAACTT TGAGGATGAG AAGCAGCTGG GCCCCGTGGG TATCCCGGAG
         R   L   R   H     F   T   W     A   W   Y     T   L   T   M     S   G   G     G   L   A
  61 AGGCTTCGCC ATTTCACTTG GGCCTGGTAC ACATTAACGA TGAGTGGAGG AGGGCTGGCC
         V   L   I   I     S   Q   P     F   G   F     R   G   L   R     E   I   G     L   A   V
 121 GTCCTCATCA TCAGCCAGCC CTTTGGGTTC CGCGGATTGA GAGAGATCGG CATCGCTGTC
         Y   I   L   N     L   I   L     F   A   L     V   C   S   T     M   A   I     R   F   I
 181 TATATCCTCA ACCTGATCCT CTTCGCCCTT GTCTGCTCTA CCATGGCTAT AAGGTTCATC
         L   H   G   N     L   L   E     S   L   R     H   D   R   E     G   L   F     F   P   T
 241 CTGCACGGCA ACCTTCTGGA GTCCCTCCGT CATGACCGCG AGGGTCTCTT CTTCCCGACC
         F   W   L   S     V   A   T     I   I   C     G   L   S   R     Y   F   G     E   E   S
 301 TTCTGGCTCT CCGTCGCAAC CATCATCTGC GGCTTGTCTC GCTACTTCGG TGAAGAATCG
         N   E   S   F     Q   L   A     L   E   A     L   F   W   I     Y   C   V     C   T   L
 361 AATGAGTCCT TCCAACTAGC CCTCGAAGCC CTCTTCTGGA TCTACTGCGT CTGCACCTTA
         L   V   A   I     I   Q   Y     S   F   V     F   S   S   H     K   Y   G     L   Q   T
 421 CTCGTCGCAA TCATCCAATA CTCGTTCGTC TTCTCATCCC ACAAGTACGG CCTTCAAACC
         M   M   P   S     W   I   L     P   A   F     P   I   M   L     S   G   T     I   A   S
 481 ATGATGCCTT CATGGATCCT TCCAGCCTTC CCCATCATGC TCAGCGGCAC CATCGCCTCC
         V   L   G   E     Q   Q   P     A   R   A     A   L   P   I     L   G   A     G   V   T
 541 GTCCTCGGTG AACAACAACC CGCTCGCGCA GCCCTCCCCA TCATCGGCCC CGGCGTCACC
         F   Q   G   L     G   F   S     L   S   F     M   M   Y   A     H   Y   L     G   R   L
 601 TTCCAGGGCC TCGGCTTCTC CATCAGCTTC ATGATGTACG CCCACTACAT CGGCCGACTG
         M   E   S   G     L   P   H     S   D   H     R   P   G   M     F   I   C     V   G   P
 661 ATGGAGTCCG GCCTCCCCCA CAGCGACCAC AGACCAGGCA TGTTCATCTG CGTCGGACCC
         P   A   F   T     A   L   A     L   V   G     M   S   K   G     L   P   E     D   F   K
 721 CCCGCCTTCA CAGCCCTCGC CCTCGTCGGC ATGAGCAAAG GCCTCCCCGA AGACTTCAAG
         L   L   H   D     A   H   A     L   E   D     G   R   I   I     E   L   L     A   I   S
 781 CTGCTCCACG ACGCCCACGC CCTGGAAGAT GGCCGCATCA TCGAGCTGCT GGCCATCTCC
         A   G   V   F     L   W   A     L   S   L     W   F   F   C     I   A   I     V   A   V
 841 GCCGGCGTCT TCCTCTGGGC CCTGAGTCTC TGGTTCTTCT GCATCGCCAT TGTCGCCGTC
         I   R   S   P     P   E   A     F   H   L     N   W   A   M     V   F     P   N   T
 901 ATCCGCTCGC CCCCCGAGGC CTTCCACCTC AACTGGTGGG CCATGGTCTT CCCCAACACC
         G   F   T   L     A   T   I     T   L   G     K   A   L   N     S   N   G     V   K   G
 961 GGCTTCACCC TGGCCACCAT CACCCTGGGC AAGGCTCTCA ACAGTAACGG TGTGAAGGGC
         V   G   S   A     M   S   I     C   I   V     C   M   Y   I     F   V   F     V   N   N
1021 GTCGGTTCCG CCATGTCTAT CTGCATCGTG TGCATGTATA TCTTCGTCTT CGTCAACAAT
         V   R   A   V     I   R   K     D   I   M     Y   P   G   K     D   E   D     V   S   D
1081 GTCCGCGCCG TTATCCGGAA GGATATCATG TACCCGGGTA AGATGAGGA TGTATCTGAT
         *
1141 TAG
```

Fig. 3

```
            M  F  A  A  R  Q  S     F  N  L     L  Q  K  R     A  F  S     A  S  A
   1  ATGTTCGCTG CTCGCCAGTC TTTCAACCTC CTCCAGAAGC GCGCCTTCTC CGCCTCTGCC
      S  Q
  61  AGCCAGCTGT GTGATTGAAT GGATCCATTG GACCTCCGAG CTAGCTCTGC AACATCAACA
                                                    A  S  K     V  A  V  L     G  A  A  ·
 121  AAACTAACAT ACTAACTTAT CTTCTTCATA GGCTTCCAAG GTTGCCGTTC TTGGTGCCGC
      ·  G  G  I     G  Q  P  L     S  L  L     L  K  L     N  P  R  V     S  E  L  ·
 181  TGGTGGCATT GGCCAGCCTC TCTCCCTTCT CCTCAAGCTC AACCCCCGTG TTTCTGAGCT
      ·  A  L  Y     D  I  R  G     G  P
 241  TGCCCTCTAC GATATCCGCG GTGGCCCTGG TATGTTTTTG CACAGCTTGC AACATCTCCG
                                                          G  V  A     A  D  L  S  ·
 301  ACTTCGGTGA TTCAAGACAG GGCTAACATA AGGATACAAT AGGTGTTGCC GCTGACCTGA
      ·  H  I  N     T  N  S     T  V  S  G     Y  F  A     T  P  S     G  L  R  D  ·
 361  GCCACATCAA CACCAACAGC ACCGTCTCTG GCTACGAGGC TACCCCCTCT GGCCTCCGTG
      ·  A  L  K     G  S  E     I  V  L  I     P  A  G     V  P  R     K  P  G  M  ·
 421  ATGCTCTCAA GGGCTCCGAG ATCGTCCTCA TCCCTGCCGG TGTTCCTCGC AAGCCCGGCA
      ·  T  R  D
 481  TGACCCGTGA CGGTATGAAC CGTTAACTTG TCAATGGCAC TGGGAATTGA ATACTAATTA
                  D  L  F     N  T  N  A     S  I  V     R  D  L     A  K  A  A  ·
 541  TAATATCGCC AGACCTGTTC AACACCAACG CCTCCATTGT CCGCGACCTT GCTAAGGCCG
      ·  A  E  A     S  P  E     A  N  I  L     V  I  S     N  P
 601  CCGCCGAGGC TTCCCCCGAG GCCAACATCC TCGTCATCTC CAACCCTGTA TGACGCTTTC
                                                       V  N  S  T     V  P  I  ·
 661  CACCCACTGC TACCAGTTAT CTCGCGCTAA TTGCAATCAG GTCAACTCCA CCGTCCCCAT
      ·  V  S  E     V  F  K  S     K  G  V     Y  N  P     K  R  L  F     G  V  T  ·
 721  CGTCTCTGAG GTCTTCAAGT CCAAGGGTGT CTACAACCCC AAGCGTCTCT TCGGTGTCAC
      ·  T  I  D     V  V  R  A     S  R  F     I  S  Q     V  Q  K  T     D  P  S  ·
 781  TACCCTTGAC GTTGTCCGTG CCTCTCGCTT CATCTCCCAG GTCCAGAAGA CCGACCCCTC
      ·  N  E  A     V  T  V  V     G  G  H     S  G  V     T  I  V  P     L  L  S  ·
 841  CAACGAGGCC GTCACTGTCG TCGGTGGTCA CTCCGGTGTG ACCATTGTCC CTCTTCTCTC
      ·  Q  S  S     H  P  S  I     E  G  K     T  R  D     E  L  V  N     R  I  Q  ·
 901  CCAGTCCAGC CACCCCAGCA TTGAGGGTAA GACCCGCCAT GAGCTCGTCA ACCGCATCCA
      ·  F  G  G     D  E  V  V     K  A  K     D  G  A     G  S  A  T     L  S  M  ·
 961  GTTCGGTGGT GATGAGGTTG TCAAGGCCAA GGATGGTGCT GGCTCTGCCA CCCTCTCCAT
      ·  A  M  A     G  A  R  M     A  E  S     L  L  K     A  A  Q  G     E  K  G  ·
1021  GGCCATGGCT GGTGCTCGCA TGGCTGAGTC CCTCCTGAAG GCCGCCCAGG GTGAGAAGGG
      ·  V  V  E     P  T  F  V     D  S  P     L  Y  K     D  Q  G  V     D  F  F  ·
1081  TGTCGTTGAG CCCACTTTCG TCGACAGCCC TCTCTACAAG GACCAGGGTG TTGACTTCTT
      ·  A  S  K     V  F  L  G     P  N  G     V  F  K     I  L  P  V     G  Q  V  ·
1141  CGCCTCCAAG GTCGAGCTCG GCCCCAACGG TGTTGAGAAG ATCCTCCCCG TTGGCCAGGT
      ·  N  A  Y     E  E  K  L     E  A  C     L  G     D  L  K  K     N  I  Q  ·
1201  CAACGCCTAC GAGGAGAAGC TCCTCGAGGC CTGCCTTGGT GACCTCAAGA AGAACATCCA
      ·  K  G  I     D  F  V  K     A  N  P     *
1261  GAAGGGTATT GACTTCGTCA AGGCCAACCC TTAA
```

Fig. 5

```
      M  V  K  A
   1 ATGGTCAAAG CTGGTGAGTT AGCAATCCTT AACAGATGAC ACTCTCATAG GTACTAACTC
              A  V  L  G  A  S  G     G  I  G  Q
  61 GAAACGTTAC CGGTACTTCG AGCTTCTGGT CGCATTGGCC ACGTATCGAT ATCCCCACGC
                                                          P  L  S  ·
 121 CTTACAACCC TGGTCACAAT ATGACCTTGT TCGATACTGA CTATCTCCCA AGCCACTGTC
     ·  L  L  L     K  T  C  P     L  V  E     E  L  A     L  Y  D  V     V  N  T  ·
 181 TCTCCTGTTG AAGACCTGTC CCTTAGTTGA AGAGCTTGCT CTCTACGATG TTGTGAACAC
     ·  P  G  V     A  A  D  L     S  H  I     S  S  I     A
 241 CCCTGGTGTT GCTGCTGATC TATCCCACAT CTCGTCTATC GCTGTACGTT ACTGCCACAA
                                                                    K
 301 TGCGAATTGC CCGATGGAAG AGGCGAAAAA TGGTATCTTG CTTACCTGGG CGATTAGAAA
        I  S  C  F     L  P  K     D  D  G     L  K  Q  A     L  T  G     A  N  I
 361 ATCTCTGGTT TTCTGCCCAA AGATGATGGG CTGAAGCAGG CCCTTACTGG TGCTAATATT
        V  V  I     P  A  G  I     P
 421 GTTGTCATCC CGGCTGGTAT TCCCCGTAAG TCCCTACCCT TTCGCATTGC TCCTCGTATG
                                      R  K  P     G  M  T     R  D  D  L  ·
 481 TTCGCTGGTG CCAGTTTTC TGATAGTTGA TAGGCAAGCC TGGTATGACC CGTGACGACC
     ·  F  K  I     N  A  G     I  V  R  D     L  V  K     G  I  A     E  F  C  P  ·
 541 TCTTCAAGAT CAACGCCGGC ATAGTGCGAG ACTTGGTCAA GGGTATCGCC GAGTTCTGCC
     ·  K  A  F     V  L  V     I  S  N  P     V  N  S     T  V  P     I  A  A  E  ·
 601 CCAAGGCCTT TGTTCTGGTT ATCTCAAACC CCGTTAATTC TACTGTTCCT ATTGCTGCAG
     ·  V  L  K     A  A  G     V  F  D  P     K  R  L     F  G  V     T  T  L  D  ·
 661 AGGTGCTCAA AGCCGCTGGC GTCTTTGACC CGAAGCGCCT CTTTGGTGTC ACCACACTGG
     ·  V  V  R     A  E  T     F  T  Q  E     F  S  G     Q  K  D     P  S  A  V  ·
 721 ACGTCGTTCC TGCAGAGACT TTCACCCAAC AGTTCTCCGG CCAGAACGAT CCTTCTGCTC
     ·  Q  I  P     V  V  G     H  S  G     E  T  I     V  P  L     F  S  K  T  ·
 781 TTCAAATCCC AGTTGTTGCT GGCCACTCTC GAGAGACCAT TCTCCCCCTC TTCAGCAAGA
     ·  T  P  A     I  Q  I     P  E  E  K     Y  D  A     L  I  H
 841 CTACCCCCGC AATTCAGATA CCCGAGGAGA AGTATGACGC ACTGATCCAC CGTAGGTTGT
                                                                    R  V  Q  F
 901 CCCAAAGAAT CTCATGAATA TCTTGCTGTA AGCACTAACT ATGCTTCAGG CGTCCAATTT
        G  G  D  E     V  V  Q     A  K  D     G  A  G  S     A  T  L     S  M  A
 961 GGTGGAGATG AGGTGGTCCA AGCTAAGGAC GGTGCTGGTT CCGCCACCTT GTCTATGGCC
        Y  A  C  Y
1021 TATGCCGGTT ACAGGTAGGG ATGCTGCGTA CCGTGAGAGC ACTCGCGGCT AACATGCCAT
        R  F  A  E     S  V  I     K  A  S     K  G  Q  T     G  I  V     E  P  T
1081 AGGTTCGCTG AGAGTGTAAT CAAAGCTTCA AAGGGTCAAA CGGGTATTGT CGAGCCTACC
        F  V  Y  L     P  G  I     P  G  G     D  E  I  V     K  A  T     G  V  E
1141 TTCGTCTACC TGCCTGGAAT TCCCGGCGGT GATGAGATCG TTAAGGCAAC TGGCGTGGAA
        F  F  S  T     L  V  T     L  G
1201 TTCTTCTCTA CTCTTGTAAC CTTAGGAGTA AGATTCATCT CCTCACAGAA TCTTCGTTCA
                                         T  N  G  A     E  K  A     S  N  V  L  ·
1261 TATCACGCCA GGCTAACGCT ATTAAACAGA CTAATGGCGC AGAGAAGGCT AGCAACGTTC
     ·  E  G  V     T  E  K     E  K  K  L     L  E  A     C  T  K     G  L  K  G  ·
1321 TTCACGGCGT CACCGAGAAG GAAAAGAAGC TTCTCCACGC TTGCACCAAA GGCCTTAAGC
     ·  N  I  E     K  G  I     D  F  V  K     N  P  P     P  K  *
1381 GTAATATCGA GAAAGCCATC GACTTCGTTA AGAACCCACC ACCAAAGTAA
```

Fig. 7

```
          M   A   A   P     F   R   Q     P   E   E     A   V   D   D     T   E   F     I   D   D
   1   ATGGCGGCTC CGTTTCGTCA GCCTGAGGAG GCGGTCGATG ACACCGAGTT CATCGATGAC
          H   H   E   H     L   R   D     T   V   H     H   R   L   R   A   N   S     S   I   M
  61   CACCATGAAC ACCTCCGTGA TACCGTGCAC ATCGGTTGC GCGCCAATTC CTCCATTATG
          H   F   Q   K     I   L   V     A   N   R     G   E   I   P     I   R   I     F   R   T
 121   CACTTCCAGA AGATCCTCGT CGCCAACCGT GGTGAGATCC CCATTCGTAT CTTCAGAACG
          A   H   E   L     S   I   Q     T   V   A     I   Y   S   H     E   D   R     L   S   M
 181   GCCCACGAGC TGTCCTTGCA GACGGTTGCT ATCTACTCTC ATGAGGATCG ACTGTCAATG
          H   R   Q   K     A   D   E     A   Y   M     I   G   H   R     G   Q   Y     T   P   V
 241   CACCGTCAAA AGGCCGATGA GGCCTACATG ATTGGCCACC GCGGTCAGTA CACCCCTGTC
          G   A   Y   L     A   G   D     E   I   I     K   I   A   L     E   H   G     V   Q   L
 301   GGTGCGTACC TGGCGGGCGA TGAGATCATC AAGATCGCCC TGGAGCACGG TGTCCAGCTG
          I   H   P   G     Y   G   F     L   S   E     N   A   D   F     A   R   K     V   E   N
 361   ATCCACCCGG GCTACGGTTT CTTGTCCGAG AACGCCGACT TCGCCCGCAA GGTTGAGAAC
          A   G   I   V     F   V   G     P   T   P     D   T   I   D     S   L   G     D   K   V
 421   GCCGGCATTG TCTTTGTGGG ACCCACTCCC GATACCATTG ACAGCTTGGG TGACAAGGTG
          S   A   R   R     L   A   I     K   C   E     V   P   V   V     P   G   T     E   G   P
 481   TCGGCCCGTC GGCTGGCCAT TAAGTGCGAG GTCCCTGTCG TTCCGGGTAC GGAGGGCCCC
          V   E   R   Y     E   E   V     K   A   F     T   D   T   Y     G   F   P     I   I   I
 541   GTCGAGCGCT ATGAGGAGGT CAAGGCGTTC ACAGACACCT ATGGCTTCCC CATCATCATC
          K   A   A   F     G   G   G     G   R   G     M   R   V   V     R   D   Q     A   E   L
 601   AAGGCTGCCT TTGGCGGTGG TGGCCGTGGT ATGCGTGTGG TCCGTGACCA GGCCGAGCTG
          R   D   S   F     E   R   A     T   S   E     A   R   S   A     F   G   N     G   T   V
 661   CGTCACTCGT TCGAGCGAGC CACCTCTGAG GCCCGCTCCG CCTTCGGCAA TGGTACCGTC
          F   V   E   R     F   L   D     K   P   K     H   I   E   V     Q   L   L     G   D   S
 721   TTCGTCGAGC GCTTCCTCGA CAAACCCAAG CACATTGAAG TCCAGCTTCT GGGTGACAGC
          H   G   N   V     V   H   L     F   E   R     D   C   S     V   Q   R   R     H   Q   K
 781   CACGGCAACG TTGTCCATCT GTTTGAGCGT GACTGCTCCG TGCAGCGTCG TCACCAGAAG
          V   V   E   V     A   P   A     K   D   I     P   A   D   V     R   D   R     I   L   A
 841   GTCGTTGAGG TTGCTCCGGC TAAGGACCTC CCAGCCGATG TCCGGGACCG CATCCTGGCC
          D   A   V   K     L   A   K     S   V   N     Y   R   N   A     G   T   A     E   F   L
 901   GATGCTGTGA AGCTGGCCAA GTCCGTCAAC TACCGTAACG CCGGTACAGC TGAGTTCCTG
          V   D   Q   Q     N   R   H     Y   F   I     E   I   N   P     R   I   Q     V   E   H
 961   GTGGACCAGC AGAACCGCCA CTACTTCATT GAAATCAATC CTCGTATCCA AGTCGAGCAC
          T   I   T   E     E   I   T     G   I   D     I   V   A   A     Q   I   Q     I   A   A
1021   ACCATCACCG AAGAGATTAC TGGTATCGAT ATCGTGGCTG CACAGATCCA GATTGCTGCT
          G   A   S   L     E   Q   L     G   L   T     Q   D   R   I     S   A   R     G   F   A
1081   GGTGCAAGCC TCGAGCAACT GGGCCTGACT CAGGACCGCA TCTCCGCCCG CGGATTTGCC
          I   Q   C   R     I   T   T     E   D   P     A   K   G   F     S   P   D     T   G   K
1141   ATTCAATGTC GTATCACCAC GGAAGATCCC GCCAAGGGGT TCTCTCCGGA TACTGGTAAG
          I   E   V   Y     R   S   A     G   G   N     G   V   R   L     D   G   G     N   G   F
1201   ATTGAGGTTT ATCGTTCCGC TGGTGGTAAC GGTGTCCGTC TGGATGGTGG TAACGGTTTC
          A   C   A   I     I   T   P     H   Y   D     S   M   L   V     K   C   T     C   R   G
1261   GCTGGTGCTA TCATCACCCC TCACTACGAC TCCATGCTGG TCAAGTGCAC CTGCCGTGGT
          S   T   Y   E     I   A   R     R   K   V     V   R   A   L     V   E   F     R   I   R
1321   TCGACCTATG AAATCGCTCG TCGCAAGGTT GTGCGTGCCT TGGTCGAGTT CCGTATTCGT
          G   V   K   T     N   I   P     F   L   T     S   L   L   S     H   P   T     F   V   D
1381   GGTGTGAAGA CCAACATTCC CTTCCTGACT TCGCTTCTGA GCCACCCGAC CTTCGTCGAT
          G   N   C   W     T   T   F     I   D   D     T   P   E   L     F   S   L     V   G   S
1441   GGAAACTGCT GGACCACTTT CATCGACGAC ACCCCTGAAT TGTTCTCTCT TGTCGGCAGT
          Q   N   R   A     Q   K   L     L   A   Y     L   G   D   V     A   V   N     C   S   S
1501   CAGAACCGTG CCCAGAAGCT GCTCGCATAC CTCGGCGATG TAGCTGTCAA CGGTAGTAGC
          I   K   G   Q     I   G   F     P   K   I     K   G   D   V     T   K   P     K   L   F
1561   ATCAAGGGCC AAATTGGCGA GCCCAAGCTC AAGGGTGATG TCATCAAGCC GAAGCTTTTC
          D   A   E   G   K   P   L     D   V   S     A   P   C   T     K   G   W     K   Q   I
1621   GATGCCGAGG GCAAGCCGCT TGACGTTTCC GCCCCCTGCA CCAAGGGTTG GAAGCAGATT
          L   D   R   E     G   P   A     A   F   A     K   A   V   R     A   N   K     G   C   L
1681   CTGGACCGGG AGGGTCCGGC TGCCTTTGCG AAGGCCGTGC GTGCCAACAA GGGTTGCTTG
          I   M   D   T     W   R   D     A   H   Q     S   L   L   A     T   R     V   R   T
1741   ATCATGGATA CTACCTGGCG TGACGCCCAC CAGTCTTTGC TGGCCACCCG TGTGCGTACC
          I   D   L   L     N   I   A     H   E   T     S   Y   A   Y     S   N   A     Y   S   L
```

Fig. 9A

```
1801 ATCGACTTGT TGAACATCGC CCATGAGACC AGCTACGCCT ACTCCAATGC GTACAGTTTG
      E  C  W  G    G  A  T    F  D  V    A  M  R  F    L  Y  E    D  P  W
1861 GAATGCTGGG GTGGTGCTAC CTTCGATGTG GCCATGCGTT TCCTCTATGA GGACCCCTGG
      D  R  L  R    K  M  R    K  A  V    P  N  I  P    F  Q  M    L  L  R
1921 GACCGCCTGC GCAAGATGCG TAAGGCTGTT CCTAACATCC CATTCCAGAT GTTGCTCCGT
      G  A  N  G    V  A  Y    S  S  L    P  D  N  A    I  Y  H    F  C  K
1981 GGTGCCAACG GTGTCGCCTA CTCTTCCCTC CCAGACAACG CCATCTACCA CTTCTGTAAG
      Q  A  K  K    C  G  V    D  I  F    R  V  F  D    A  L  N    D  V  D
2041 CAGGCTAAGA AGTGCGGTGT CGACATTTTC CGTGTTTTCG ACGCCCTCAA CGATGTCGAT
      Q  L  E  V    G  I  K    A  V  H    A  A  E  G    V  V  E    A  T  M
2101 CAGCTCGAGG TCGCTATCAA CGCTCTTCAT GCTGCCGAGG GTGTTGTCGA CGCCACCATG
      C  Y  S  G    D  M  L    N  P  H    K  K  Y  N    L  E  Y    Y  M  A
2161 TGCTACAGCG GTGACATGCT GAACCCCCAC AAGAAGTACA ACCTGGAGTA CTACATGGCC
      L  V  D  K    I  V  A    M  K  P    H  I  L  G    I  K  D    M  A  G
2221 TTGGTGGATA AGATTGTAGC CATGAAGCCT CACATCCTTG GTATCAAGGA TATGGCCGGT
      V  L  K  P    Q  A  A    R  L  L    V  G  S  I    R  Q  R    Y  P  D
2281 GTGCTGAAGC CCCAGGCCGC TCGCCTGTTG GTGGGCTCCA TCCGTCAGCG CTACCCTGAC
      L  P  I  H    V  H  T    H  D  S    A  G  T  G    V  A  S    M  I  A
2341 CTTCCCATCC ACGTCCACAC CCACGACTCC GCTGGTACTG GTGTAGCTTC CATGATTGCC
      C  A  Q  A    G  A  D    A  V  D    A  A  T  D    S  M  S    G  M  T
2401 TGTGCCCAGG CGGGTGCCGA CGCCGTGGAC GCCGCGACCG ACAGCATGTC CGGTATGACC
      S  Q  P  S    I  G  A    I  L  A    S  L  E  G    T  E  Q    D  P  G
2461 TCCCAGCCTA GCATTGGTGC CATTCTGGCC TCTCTTGAGG GCACTGAGCA AGACCCCGGT
      L  N  L  A    H  V  R    A  I  D    S  Y  W  A    Q  L  R    L  L  Y
2521 CTCAACCTCG CCCACGTGCG CGCTATTGAT AGCTACTGGG CACAGCTGCG CTTGCTCTAC
      S  P  F  E    A  G  L    T  G  P    D  P  E  V    Y  E  H    E  I  P
2581 TCTCCTTTCG AGGCGGGTCT CACTGGCCCC GACCCTGAGG TCTACGAGCA CGAGATCCCT
      G  G  Q  L    T  N  L    F  Q    A  S  Q  L    G  L  G    Q  Q  W
2641 GGTGGTCAGT TGACCAACCT TATCTTCCAG GCCAGTCAGC TCGGCTTGGG CCAGCAGTGG
      A  E  T  K    K  A  Y    E  A  A    N  D  L  L    G  D  I    V  K  V
2701 GCCGAAACCA AGAAGGCCTA TGAGGCGGCT AATGATTTAC TCGGCGACAT TGTAAAGGTC
      T  P  T  S    K  V  V    G  D  L    A  Q  F  M    V  S  N    K  L  T
2761 ACTCCCACCT CCAAGGTCGT CGGTGACTTG GCTCACTTCA TGGTCTCGAA CAAACTGACT
      P  E  D  V    V  E  R    A  G  F    L  D  F  P    G  S  V    L  E  F
2821 CCAGAGGATG TTGTTGAGCG TGCTGGTGAG CTGGACTTCC CTGGTTCTGT GCTCGAATTC
      L  E  G  L    M  G  Q    P  F  G    G  F  P  E    P  L  R    S  R  A
2881 CTCGAAGGTC TCATGGGACA GCCCTTCGGT GGATTCCCCG AGCCATTGCG CTCCCGCGCC
      L  R  D  R    R  K  L    E  K  R    P  G  L  Y    L  E  P    L  D  L
2941 CTGCGCGATC GCCGCAAGCT CGAGAAGCGT CCAGGTCTCT ACCTCGAGCC TTTGGATTTG
      A  K  I  K    S  Q  I    R  E  K    F  G  A  A    T  E  Y    D  V  A
3001 GCTAAGATCA AGAGCCAGAT CCGTGAGAAG TTCGGTGCTG CTACTGAGTA TGACGTGGCC
      S  Y  A  M    Y  P  K    V  F  E    D  Y  K  K    F  V  Q    K  F  G
3061 AGCTATGCCA TGTATCCCAA GGTCTTCGAG GACTACAAGA AGTTCGTCCA GAAGTTCGGT
      D  L  S  V    L  P  T    R  Y  F    L  A  K  P    E  I  G    E  E  F
3121 GATCTCTCCG TCTTGCCCAC ACGGTACTTC TTGGCCAAGC CTGAGATTGG CGAGGAGTTC
      H  V  E  L    E  K  G    K  V  L    I  L  K  L    L  A  I    G  P  L
3181 CACGTTGAGC TGGAGAAGGG TAAGGTGCTC ATCCTGAAGT TGTTGGCCAT CGGCCCTCTT
      S  E  Q  T    G  Q  R    E  V  F    Y  E  V  N    G  E  V    R  Q  V
3241 TCAGAGCAGA CTGGTCAGCG TGAGGTCTTC TACGAAGTCA ACGGTGAGGT GCGCCAGGTC
      A  V  D  D    N  K  A    S  V  D    N  T  S  R    P  K  A    D  V  G
3301 GCTGTTGATG ACAACAAGGC TTCCGTGGAC AACACTTCAC GCCCTAAGGC CGATGTGGGT
      D  S  S  Q    V  G  A    P  M  S    C  V  V  V    E  I  R    V  H  D
3361 GACAGCAGCC AGGTCGGTGC TCCTATGAGC GGTGTGGTTG TTGAAATCCG TGTCCACGAT
      G  L  E  V    K  K  G    D  P  L    A  V  L  S    A  M  K    M
3421 GGTCTGGAGG TTAAGAAGGG TGACCCACTT GCCGTCCTGA GTGCCATGAA GATGGTAAGT
                                                                        E  M ·
3481 TCATTCCGAA TCATTTTTCT CACTGGTCAA CTACAGATGC TAACAGCTTA TCCAGGAAAT
      ·  V  I  S    A  P  H  S    G  K  V    S  S  L    L  V  K  E    G  D  S·
3541 GGTTATCTCT GCTCCTCACA GTGGAAAGGT CTCCAGCTTG CTGGTCAAGG AGGGCGATTC
      ·  V  D  G    Q  D  L  V    C  K  I    V  K  A    *
3601 TGTGGATGGC CAGGATCTCG TCTGCAAGAT CGTCAAAGCG TAA
```

Fig. 9B

```
      M   F   E   N   T   A   P     P   G   S     S   R   S   D     S   G   I   L   D   H
   1  ATGTTTGAGA ACACTGCCCC TCCAGGGAGC TCCCGCTCCG ACTCTGGCAT CCTGGACCAT
      E   F   E   K     Q   P   G     S   V   G     M   R   E   R     I   R   H   F   T   W
  61  GAATTCGAGA AGCAGCCGGG TTCCGTGGGC ATGCGTGAAC GCATCCGCCA TTTTACCTGG
      A   W   Y   T     L   T   M     S   A   G     G   L   A   L     L   L   G   S   Q   P
 121  GCCTGGTATA CTCTCACAAT GAGTGCTGGT GGCTTGGCCC TCCTCCTTGG GAGCCAGCCA
      N   T   F   T     G   L   R     F   I   G     L   A   V   Y     L   N   L   L   F
 181  AACACCTTCA CCGGCCTGAG GGAGATTGGA CTCGCCGTCT ACCTGCTCAA CCTGCTCTTC
      F   A   L   V     C   S   T     M   A   G     R   F   I   L     H   G   G   L   V   D
 241  TTTGCCCTGG TCTGCTCGAC CATGGCCGGC CGGTTCATCC TGCACGGAGG GCTGGTCGAC
      S   L   R   H     E   R   E     G   I   F     F   P   T   F     W   L   S   I   A   T
 301  TCTCTCCGGC ACGAACGCGA GGGCATCTTC TTCCCAACCT TCTGGCTCTC GATCGCCACC
      I   I   T   G     L   Y   R     Y   F   G     E   D   A   G     R   P   F   V   L   A
 361  ATCATCACAG GCCTGTACCG CTACTTCGGC GAAGACGCCG GACGCCCCTT CGTGCTCGCC
      L   E   A   L     F   W   I     Y   C   A     C   T   L   L     V   A   V   I   Q   Y
 421  CTCGAAGCCC TCTTCTGGAT CTACTGCGCT TGCACCCTCC TCGTCGCCGT CATCCAATAC
      S   W   L   F     S   G   P     K   Y   R     L   Q   T   A     M   P   G   W   I   L
 481  TCCTGGCTCT TCTCCGGCCC CAAATACCGC CTCCAAACCG CCATGCCCGG CTGGATCCTC
      P   A   F   P     V   M   L     S   G   T     I   A   S   V     I   A   E   Q   Q   P
 541  CCCGCCTTCC CTGTCATGCT CTCTGGCACC ATCGCCTCCG TCATCGCCGA GCAGCAGCCG
      A   R   A   A     I   P   I     I   V   A     G   T   T   F     Q   G   L   G   F   S
 601  GCCCGCGCCG CCATCCCCAT CATCGTCGCC GGCACCACCT TCCAGGGCCT GGGCTTCTCC
      I   S   M   I     M   Y   A     H   Y   V     G   R   L   M     E   S   G   L   P   C
 661  ATCAGCATGA TCATGTACGC CCACTACGTC GGCCGCCTCA TGGAGTCCGG CCTGCCGTGC
      R   E   H   R     P   G   M     F   I   A     V   G   P   P     A   F   T   A   L   A
 721  CGCGAGCACC GCCCGGGCAT GTTCATCGCC GTCGGCCCGC CGGCTTTCAC GGCGCTGGCC
      L   V   G   M     T   K   G     L   P   H     D   F   Q   L     I   G   D   D   F   A
 781  CTCGTCGGCA TGACCAAGGG GCTCCCGCAC GACTTCCAGC TCATCGGCGA TGACTTCGCC
      F   E   D   A     R   I   L     Q   L   L     A   I   A   V     G   V   F   L   W   A
 841  TTCGAGGATG CCCGCATCCT GCAGCTGCTG GCGATCGCCG TCGGCGTGTT TCTCTGGGCG
      L   S   L   W     F   F   C     L   A   A     L   A   V   V     R   S   P   P   T   A
 901  CTGAGTCTGT GGTTCTTTTG CATTGCCGCC ATTGCCGTCG TGCGCTCCCC GCCAACGGCC
      F   H   L   S     W   W   A     M   V   F     P   N   T   G     F   T   L   A   T   I
 961  TTCCACCTGA GCTGGTGGGC CATGGTCTTC CCCAACACGG GCTTCACCCT CGCCACGATC
      N   L   G   T     A   L   K     S   E   G     I   Q   G   V     G   T   A   M   S   I
1021  AACCTGGGTA CGGCCCTCAA GAGCGAGGGT ATCCAGGGTG TGGGGACGGC CATGTCGATT
      G   I   V   S     I   F   L     F   V   F     I   S   H   V     R   A   V   I   R   K
1081  GGAATTGTGT CTATTTTCTT GTTTGTGTTT ATCAGCCATG TGCGGGCTGT CATCAGGAAA
      D   I   M   Y     P   G   K     D   E   D     V   V   E   *
1141  GACATTATGT ATCCTGGGAA AGACGAGGAT GTGGTGGAGT AA
```

Fig. 13

```
           M   G   E   L   K   E   I   L   K   Q   R   Y   H   E   L   L   D   W   N   V
CO       1 ATGGGAGAAT TGAAGGAAAT TCTCAAGCAG CGCTACCATG AATTGCTCGA CTGGAACGTC
WT       1 ATCGGTCAAC TCAACGAAAT CTTGAAACAG AGGTATCATC AGTTGCTTGA CTGGAATGTC

K   A   P   H   V   P   L   S   Q   R   L   K   H   F   T   W   S   W   F   A
CO      61 AAAGCACCCC ACGTCCCTCT CTCGCAGAGG TTGAAGCATT TCACATGGTC GTGGTTCGCG
WT      61 AAAGCCCCTC ATGTCCCTCT CAGTCAACGA CTGAAGCATT TTACATGGTC TTGGTTTGCA

C   T   M   A   T   G   G   V   G   L   I   I   G   S   F   P   F   R   F   Y
CO     121 TGTACGATGG CAACCGGTGG CGTCGGACTC ATCATCGGAT CCTTCCCTTT CCGATTCTAC
WT     121 TGTACTATGG CAACTGGTGG TGTTGGTTTG ATTATTGGTT CTTTCCCCTT TCGATTTTAT

G   L   N   T   I   G   K   I   V   Y   I   L   Q   I   F   L   F   S   L   F
CO     181 GGACTCAACA CGATCGGCAA GATTGTGTAC ATCCTCCAGA TTTTCCTCTT CTCCTTGTTC
WT     181 GGTCTTAATA CAATTGGCAA AATTGTTTAT ATTCTTCAAA TCTTTTTGTT TTCTCTCTTT

G   S   C   M   L   F   R   F   I   K   Y   P   S   T   I   K   D   S   W   N
CO     241 GGCTCGTGTA TGCTCTTCAC GTTCATCAAG TATCCGTCCA CAATCAAGGA CTCCTGGAAC
WT     241 GGATCATGCA TGCTTTTTCG CTTTATTAAA TATCCTTCAA CTATCAAGGA TTCCTGGAAC

H   H   L   E   K   L   F   I   A   T   C   L   L   S   I   S   T   F   I   D
CO     301 CATCATCTCG AGAAACTCTT CATTGCGACT TGTCCTCCTCT CGATTTCGAC ATTCATCGAT
WT     301 CATCATTTGG AAAACCTTTT CATTGCTACT TGTCTTCTTT CAATATCCAC CTTCATCGAC

M   L   A   I   Y   A   Y   P   D   T   G   E   W   M   V   W   V   I   R   I
CO     361 ATGTTGGCGA TCTACGCCTA CCCCGACACA GGCGAGTGGA TGGTGTGGGT CATCCGAATC
WT     361 ATGCTTGCCA TATACGCCTA TCCTGATACC GGCGAGTGGA TGGTGTGGGT CATTCGAATC

L   Y   Y   I   Y   V   A   V   S   F   I   Y   C   V   M   A   F   F   T   I
CO     421 CTCTACTACA TCTACGTCGC GGTCTCCTTC ATTTACTGTG TGATGGCGTT CTTCACGATC
WT     421 CTTTATTACA TTTACGTTGC AGTATCCTTT ATATACTGCG TAATGGCTTT TTTTACAATT

F   N   N   H   V   Y   T   I   E   T   A   S   P   A   W   I   L   P   I   F
CO     481 TTCAACAACC ACGTCTATAC CATTGAAACC GCCTCGCCTG CATGGATCCT CCCTATCTTC
WT     481 TTCAACAACC ATGTATATAC CATTGAAACC GCATCTCCTG CTTGGATTCT TCCTATTTTC

P   P   M   I   C   G   V   I   A   G   A   V   N   S   T   Q   P   A   H   Q
CO     541 CCTCCGATGA TCTGTGGTGT CATTGCCGGT GCGGTGAACT CCACCCAGCC TGCGCACCAG
WT     541 CCTCCTATGA TTTGTGGTGT CATTGCTGGC GCCGTCAATT CTACACAACC CGCTCATCAA

L   K   N   M   V   I   F   G   I   L   F   Q   G   L   G   F   W   V   Y   L
CO     601 CTCAAAAACA TGGTGATTTT CGGAATCCTC TTCCAGGGAT TGGGTTTCTG GGTCTACTTG
WT     601 TTAAAAAATA TGGTTATCTT TGGTATCCTC TTTCAAGGAC TTGGTTTTTG GGTTTATCTT

L   L   F   A   V   N   V   L   R   F   F   T   V   G   L   A   K   P   Q   D
CO     661 CTCTTGTTCG CAGTCAACGT GCTCCGGTTC TTCACGGTCG GCTTGGCAAA GCCCCAGGAC
WT     661 TTACTGTTTG CCGTCAATGT CTTACGGTTT TTTACTGTAG GCCTGGCAAA ACCCCAAGAT

R   P   G   M   F   M   F   V   G   P   P   A   F   S   G   L   A   L   I   N
CO     721 CGACCTGGCA TGTTCATGTT CGTGGGACCT CCTGCGTTCT CCGGCTTGGC ACTCATCAAC
WT     721 CGACCTGGTA TGTTTATGTT TGTCGGTCCA CCAGCTTTCT CAGGTTTGGC CTTAATTAAT

I   A   R   G   A   M   G   S   R   P   Y   I   F   V   G   A   N   S   S   E
CO     781 ATCGCGAGGG GTGCCATGGG CTCGAGGCCG TACATCTTCG TGGGAGCAAA CTCCTCGGAA
WT     781 ATTGCGCGTG GTGCTATGGG CAGTCGCCCT TATATTTTTG TTGGCGCCAA CTCATCCGAG

Y   L   G   F   V   S   T   F   M   A   I   F   I   W   G   L   A   A   W   C
CO     841 TACTTGGGTT TCGTCTCGAC GTTCATGGCG ATTTTCATCT GGGGCTTGGC AGCATGGTGT
WT     841 TATCTTGGTT TTGTTTCTAC CTTTATGGCT ATTTTTATT GGGGTCTTGC TGCTTGGTGT
```

Fig. 16A

```
           Y  C  L  A  M  V  S     F  L  A     G  F  F  T  R  A  P     L  K  F
CO   901 TATTGTCTCG CCATGGTGTC CTTCCTCGCA GGCTTCTTCA CACGCGCACC TTTGAAGTTC
WT   901 TACTGTCTCG CCATGGTTAG CTTTTTAGCG GGCTTTTTCA CTCGAGCCCC TCTCAAGTTT

A  C  G  W     F  A  F     I  F  P     N  V  G  F     V  N  C     T  I  E
CO   961 GCGTGTGGTT GGTTCGCATT CATCTTCCCC AACGTGGGCT TCGTGAACTG TACGATTGAG
WT   961 GCTTGTGGAT GGTTTGCATT CATTTTCCCC AACGTGGGTT TTGTTAATTG TACCATTGAG

I  G  K  M     I  D  S     K  A  F     Q  M  F  G     H  I  I     G  V  I
CO  1021 ATCGGCAAGA TGATCGACTC CAAAGCCTTC CAGATGTTCG GCCACATTAT CGGTGTCATC
WT  1021 ATAGGTAAAA TGATAGATTC CAAAGCTTTC CAAATGTTTG GACATATCAT TGGGGTCATT

I  C  I  Q     W  I  L     M  Y     L  M  V  R     A  F  L     V  N  D
CO  1081 CTCTGTATCC AGTGGATTTT GCTCATGTAT TTGATGGTGC GTGCGTTCTT GGTCAACGAC
WT  1081 CTTTGTATTC AGTGGATCCT CCTAATGTAT TTAATGGTCC GTGCGTTTCT CGTCAATGAT

L  C  Y  P     G  K  D     E  D  A     H  P  P     P  K  P  N     T  G  V
CO  1141 TTGTGTTATC CCGGTAAAGA CGAGGACGCC CATCCCCCTC CAAAACCCAA CACAGGCGTC
WT  1141 CTTTGCTATC CTGGCAAAGA CGAAGATGCC CATCCTCCAC CAAAACCAAA TACAGGTGTC

L  N  P  T     F  P  P     E  K  A     P  A  S  L     E  K  V     D  T  H
CO  1201 CTCAACCCCA CCTTCCCTCC CGAAAAAGCA CCTGCCTCCC TCGAAAAAGT CGATACACAT
WT  1201 CTTAACCCTA CCTTCCCACC TGAAAAAGCA CCTGCATCTT TGGAAAAAGT CGATACACAT

V  T  S  T     G  G  E     S  D  P     P  S  S  E     H  E  S     V  *
CO  1261 GTCACTTCCA CTGGCGGAGA GTCGGATCCT CCGTCCTCCG AACACGAGTC GGTCTAA
WT  1261 GTCACATCTA CTGGTGGTGA ATCGGATCCT CCTAGTAGTG AACATCAAAG CCTTTAA
```

Fig. 16B

```
                         SEQUENCE LISTING

<160> NUMBER OF SEQ ID NOS: 41

<210> SEQ ID NO 1
<211> LENGTH: 40
<212> TYPE: DNA
<213> ORGANISM: Aspergillus oryzae

<400> SEQUENCE: 1
gtgatagaac atcgtccata atgctgacac ctcccaagtt                         40

<210> SEQ ID NO 2
<211> LENGTH: 43
<212> TYPE: DNA
<213> ORGANISM: Aspergillus oryzae

<400> SEQUENCE: 2
agtcacctct agttaattaa ttactaatca gatacatcct cat                     43

<210> SEQ ID NO 3
<211> LENGTH: 25
<212> TYPE: DNA
<213> ORGANISM: Aspergillus oryzae

<400> SEQUENCE: 3
ctatagcgaa atggattgat tgtct                                         25

<210> SEQ ID NO 4
<211> LENGTH: 20
<212> TYPE: DNA
<213> ORGANISM: Aspergillus oryzae

<400> SEQUENCE: 4
tgaccttcca cgctgaccac                                               20

<210> SEQ ID NO 5
<211> LENGTH: 19
<212> TYPE: DNA
<213> ORGANISM: Aspergillus oryzae

<400> SEQUENCE: 5
ctaatcagat acatcctca                                                19

<210> SEQ ID NO 6
<211> LENGTH: 19
<212> TYPE: DNA
<213> ORGANISM: Aspergillus oryzae

<400> SEQUENCE: 6
atgctgacac ctcccaagt                                                19
```

<210> SEQ ID NO 7
<211> LENGTH: 1143
<212> TYPE: DNA
<213> ORGANISM: Aspergillus oryzae

<400> SEQUENCE: 7

| | | | | | |
|---|---|---|---|---|---|
| atgctgacac | ctcccaagtt | tgaggatgag | aagcagctgg | ccccgtgggg | tatccgggag | 60 |
| aggcttcgcc | atttcacttg | gcctggtac | acattaacga | tgagtggagg | agggctggcc | 120 |
| gtcctcatca | tcagccagcc | ctttgggttc | cgcggattga | gagagatcgg | catcgctgtc | 180 |
| tatatcctca | acctgatcct | cttcgcccctt | gtctgctcta | ccatggctat | aaggttcatc | 240 |
| ctgcacggca | accttctgga | gtccctccgt | catgaccgcg | agggtctctt | cttcccgacc | 300 |
| ttctggctct | ccgtcgcaac | catcatctgc | ggcttgtctc | gctacttcgg | tgaagaatcg | 360 |
| aatgagtcct | tccaactagc | cctcgaagcc | ctcttctgga | tctactgcgt | ctgcacctta | 420 |
| ctcgtcgcaa | tcatccaata | ctcgttcgtc | ttctcatccc | acaagtacgg | ccttcaaacc | 480 |
| atgatgcctt | catggatcct | tccagccttc | cccatcatgc | tcagcggcac | catcgcctcc | 540 |
| gtcatcggtg | aacaacaacc | cgctcgcgca | gccctcccca | tcatcggcgc | cggcgtcacc | 600 |
| ttccagggcc | tcggcttctc | catcagcttc | atgatgtacg | cccactacat | cggccgactg | 660 |
| atggagtccg | gcctccccca | cagcgaccac | agaccaggca | tgttcatctg | cgtcggaccc | 720 |
| cccgccttca | cagccctcgc | cctcgtcggc | atgagcaaag | gcctccccga | agacttcaag | 780 |
| ctgctccacg | acgccacgc | cctggaagat | ggccgcatca | tcgagctgct | ggccatctcc | 840 |
| gccggcgtct | tcctctgggc | cctgagtctc | tggttcttct | gcatcgccat | tgtcgccgtc | 900 |
| atccgctcgc | ccccccgaggc | cttccacctc | aactggtggg | ccatggtctt | ccccaacacc | 960 |
| ggcttcaccc | tggccaccat | caccctgggc | aaggctctca | acagtaacgg | tgtgaagggc | 1020 |
| gtcggttccg | ccatgtctat | ctgcatcgtg | tgcatgtata | tcttcgtctt | cgtcaacaat | 1080 |
| gtccgcgccg | ttatccggaa | ggatatcatg | tacccgggta | agatgagga | tgtatctgat | 1140 |
| tag | | | | | | 1143 |

<210> SEQ ID NO 8
<211> LENGTH: 380
<212> TYPE: PRT
<213> ORGANISM: Aspergillus oryzae

<400> SEQUENCE: 8

```
Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125
```

```
Glu Ala Leu Phe Trp Ile Tyr Cys Val Cys Thr Leu Leu Val Ala Ile
        130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Pro Ala Arg Ala Ala Leu
        180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
        210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
                260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
                340                 345                 350

Tyr Ile Phe Val Phe Val Asn Asn Val Arg Ala Val Ile Arg Lys Asp
                355                 360                 365

Ile Met Tyr Pro Gly Lys Asp Glu Asp Val Ser Asp
        370                 375                 380

<210> SEQ ID NO 9
<211> LENGTH: 49
<212> TYPE: DNA
<213> ORGANISM: Aspergillus oryzae

<400> SEQUENCE: 9
acacaactgg ccatgttcgc tgctcgccag tctttcaacc tcctccaga         49

<210> SEQ ID NO 10
<211> LENGTH: 60
<212> TYPE: DNA
<213> ORGANISM: Aspergillus oryzae

<400> SEQUENCE: 10
agtcacctct agttaattaa ttattaaggg ttggccttga cgaagtcaat acccttctga    60

<210> SEQ ID NO 11
<211> LENGTH: 49
<212> TYPE: DNA
<213> ORGANISM: Aspergillus oryzae

<400> SEQUENCE: 11
acacaactgg ccatggtcaa agctggtgag ttagcaatcc ttaacagat          49

<210> SEQ ID NO 12
```

```
<211> LENGTH: 60
<212> TYPE: DNA
<213> ORGANISM: Aspergillus oryzae

<400> SEQUENCE: 12
agtcacctct agttaattaa ttattacttt ggtggtgggt tcttaacgaa gtcgatgcct    60

<210> SEQ ID NO 13
<211> LENGTH: 20
<212> TYPE: DNA
<213> ORGANISM: Aspergillus oryzae

<400> SEQUENCE: 13
ctttggtgtc accacactgg                                                20

<210> SEQ ID NO 14
<211> LENGTH: 20
<212> TYPE: DNA
<213> ORGANISM: Aspergillus oryzae

<400> SEQUENCE: 14
gggatttgaa cagcagaagg                                                20

<210> SEQ ID NO 15
<211> LENGTH: 23
<212> TYPE: DNA
<213> ORGANISM: Aspergillus oryzae

<400> SEQUENCE: 15
cttagcaagg tcgcggacaa tgg                                            23

<210> SEQ ID NO 16
<211> LENGTH: 19
<212> TYPE: DNA
<213> ORGANISM: Aspergillus oryzae

<400> SEQUENCE: 16
ggcactggga attgaatac                                                 19

<210> SEQ ID NO 17
<211> LENGTH: 1294
<212> TYPE: DNA
<213> ORGANISM: Aspergillus oryzae

<400> SEQUENCE: 17
atgttcgctg ctcgccagtc tttcaacctc ctccagaagc gcgccttctc cgcctctgcc    60
agccaggtgt gtgattgaat ggatccattg gacctcggag ctagctctgc aacatcaaca   120
aaactaacat actaacttat cttcttcata ggcttccaag gttgccgttc ttggtgccgc   180
tggtggcatt ggccagcctc tctcccttct cctcaagctc aaccccgtg tttctgagct    240 tgccctctac gatatccgcg gtggccctgg tatgttttttg cacagcttgc aacatctccg   300
acttcggtga ttcaagacag gctaacata aggatacaat aggtgttgcc gctgacctga    360
gccacatcaa caccaacagc accgtctctg gctacgaggc tacccctct ggcctccgtg    420 atgctctcaa gggctccgag atcgtcctca tccctgccgg tgttcctcgc aagcccggca   480
tgacccgtga cggtatgaac cgttaacttg tcaatggcac tgggaattga atactaatta   540
taatatcgcc agacctgttc aacaccaacg cctccattgt ccgcgacctt gctaaggccg   600
ccgccgaggc ttcccccgag gccaacatcc tcgtcatctc caaccctgta tgacgctttc    660
cacccactgc taccagttat ctcgcgctaa ttgcaatcag gtcaactcca ccgtcccat    720
```

-continued

```
cgtctctgag gtcttcaagt ccaagggtgt ctacaacccc aagcgtctct tcggtgtcac    780 taccccttgac gttgtccgtg cctctcgctt catctcccag gtccagaaga ccgacccctc   840
caacgaggcc gtcactgtcg tcggtggtca ctccggtgtg accattgtcc ctcttctctc   900
ccagtccagc cacccagca ttgagggtaa gacccgcgat gagctcgtca accgcatcca   960
gttcggtggt gatgaggttg tcaaggccaa ggatggtgct ggctctgcca ccctctccat   1020
ggccatggct ggtgctcgca tggctgagtc cctcctgaag gccgcccagg gtgagaaggg   1080
tgtcgttgag cccactttcg tcgacagccc tctctacaag gaccagggtg ttgacttctt   1140
cgcctccaag gtcgagctcg gccccaacgg tgttgagaag atcctccccg ttggccaggt   1200
caacgcctac gaggagaagc tcctcgaggc ctgccttggt gacctcaaga gaacatcca   1260 gaagggtatt gacttcgtca aggccaaccc ttaa   1294
```

<210> SEQ ID NO 18
<211> LENGTH: 340
<212> TYPE: PRT
<213> ORGANISM: Aspergillus oryzae

<400> SEQUENCE: 18

```
Met Phe Ala Ala Arg Gln Ser Phe Asn Leu Gln Lys Arg Ala Phe
1               5                   10                  15

Ser Ala Ser Ala Ser Gln Ala Ser Lys Val Ala Val Leu Gly Ala Ala
            20                  25                  30

Gly Gly Ile Gly Gln Pro Leu Ser Leu Leu Lys Leu Asn Pro Arg
        35                  40                  45

Val Ser Glu Leu Ala Leu Tyr Asp Ile Arg Gly Gly Pro Gly Val Ala
    50                  55                  60

Ala Asp Leu Ser His Ile Asn Thr Asn Ser Thr Val Ser Gly Tyr Glu
65                  70                  75                  80

Ala Thr Pro Ser Gly Leu Arg Asp Ala Leu Lys Gly Ser Glu Ile Val
                85                  90                  95

Leu Ile Pro Ala Gly Val Pro Arg Lys Pro Gly Met Thr Arg Asp Asp
            100                 105                 110

Leu Phe Asn Thr Asn Ala Ser Ile Val Arg Asp Leu Ala Lys Ala Ala
        115                 120                 125

Ala Glu Ala Ser Pro Glu Ala Asn Ile Leu Val Ile Ser Asn Pro Val
    130                 135                 140

Asn Ser Thr Val Pro Ile Val Ser Glu Val Phe Lys Ser Lys Gly Val
145                 150                 155                 160

Tyr Asn Pro Lys Arg Leu Phe Gly Val Thr Thr Leu Asp Val Val Arg
                165                 170                 175

Ala Ser Arg Phe Ile Ser Gln Val Gln Lys Thr Asp Pro Ser Asn Glu
            180                 185                 190

Ala Val Thr Val Val Gly Gly His Ser Gly Val Thr Ile Val Pro Leu
        195                 200                 205

Leu Ser Gln Ser Ser His Pro Ser Ile Glu Gly Lys Thr Arg Asp Glu
    210                 215                 220

Leu Val Asn Arg Ile Gln Phe Gly Gly Asp Glu Val Val Lys Ala Lys
225                 230                 235                 240

Asp Gly Ala Gly Ser Ala Thr Leu Ser Met Met Ala Gly Ala Arg
                245                 250                 255

Met Ala Glu Ser Leu Leu Lys Ala Ala Gln Gly Glu Lys Gly Val Val
            260                 265                 270

Glu Pro Thr Phe Val Asp Ser Pro Leu Tyr Lys Asp Gln Gly Val Asp
```

275                 280                 285
Phe Phe Ala Ser Lys Val Glu Leu Gly Pro Asn Gly Val Glu Lys Ile
        290                 295                 300

Leu Pro Val Gly Gln Val Asn Ala Tyr Glu Glu Lys Leu Leu Glu Ala
305                 310                 315                 320

Cys Leu Gly Asp Leu Lys Lys Asn Ile Gln Lys Gly Ile Asp Phe Val
                325                 330                 335

Lys Ala Asn Pro
            340

<210> SEQ ID NO 19
<211> LENGTH: 1430
<212> TYPE: DNA
<213> ORGANISM: Aspergillus oryzae

<400> SEQUENCE: 19
atggtcaaag ctggtgagtt agcaatcctt aacagatgac actctcatag gtactaactc        60
gaaacgttag cggtacttgg agcttctggt ggcattggcc aggtatggat atccccacgc       120
cttacaaccc tggtcacaat atgaccttgt tcgatactga ctatctccca agccactgtc       180
tctcctgttg aagacctgtc ccttagttga agagcttgct ctctacgatg ttgtgaacac       240
ccctggtgtt gctgctgatc tatcccacat ctcgtctatc gctgtacgtt actgccacaa       300
tgcgaattgc ccgatggaag aggcgaaaaa tggtatcttg cttacctggg cgattagaaa       360
atctctggtt ttctgcccaa agatgatggg ctgaagcagg cccttactgg tgctaatatt       420
gttgtcatcc cggctggtat tccccgtaag tccctaccct ttcgcattgc tcctcgtatg       480
ttcgctggtg ccagttttc tgatagttga taggcaagcc tggtatgacc cgtgacgacc        540
tcttcaagat caacgccggc atagtgcgag acttggtcaa gggtatcgcc gagttctgcc       600
ccaaggcctt tgttctggtt atctcaaacc ccgttaattc tactgttcct attgctgcag       660
aggtgctcaa agccgctggc gtctttgacc cgaagcgcct ctttggtgtc accacactgg       720
acgtcgttcg tgcagagact ttcacccaag agttctcggg ccagaaggat ccttctgctg       780
ttcaaatccc agttgttggt ggccactctg agagaccatg tgtcccctc ttcagcaaga        840 ctaccccgc aattcagata cccgaggaga gtatgacgc actgatccac cgtaggttgt         900
cccaaagaat ctcatgaata tcttgctgta agcactaact atgcttcagg cgtccaattt       960
ggtggagatg aggtggtcca agctaaggac ggtgctggtt ccgccacctt gtctatggcc      1020
tatgccggtt acaggtaggg atgctgcgta ccgtgagagc actcgcggct aacatgccat      1080
aggttcgctg agagtgtaat caaagcttca aagggtcaaa cgggtattgt cgagcctacc      1140
ttcgtctacc tgcctggaat tcccggcggt gatgagatcg ttaaggcaac tggcgtggaa      1200
ttcttctcta ctcttgtaac cttaggagta agattcatct cctcacagaa tcttcgttca      1260
tatcacgcca ggctaacgct attaaacaga ctaatggcgc agagaaggct agcaacgttc      1320
ttgagggcgt gaccgagaag gaaaagaagc ttctcgaggc ttgcacgaaa ggccttaagg      1380
gtaatatcga aaaggcatc gacttcgtta agaacccacc accaaagtaa              1430

<210> SEQ ID NO 20
<211> LENGTH: 330
<212> TYPE: PRT
<213> ORGANISM: Aspergillus oryzae

<400> SEQUENCE: 20

Met Val Lys Ala Ala Val Leu Gly Ala Ser Gly Gly Ile Gly Gln Pro
1               5                   10                  15

```
Leu Ser Leu Leu Leu Lys Thr Cys Pro Leu Val Glu Glu Leu Ala Leu
             20                  25                  30

Tyr Asp Val Val Asn Thr Pro Gly Val Ala Ala Asp Leu Ser His Ile
             35                  40                  45

Ser Ser Ile Ala Lys Ile Ser Gly Phe Leu Pro Lys Asp Asp Gly Leu
 50                  55                  60

Lys Gln Ala Leu Thr Gly Ala Asn Ile Val Ile Pro Ala Gly Ile
 65                  70                  75                  80

Pro Arg Lys Pro Gly Met Thr Arg Asp Asp Leu Phe Lys Ile Asn Ala
                 85                  90                  95

Gly Ile Val Arg Asp Leu Val Lys Gly Ile Ala Glu Phe Cys Pro Lys
                100                 105                 110

Ala Phe Val Leu Val Ile Ser Asn Pro Val Asn Ser Thr Val Pro Ile
                115                 120                 125

Ala Ala Glu Val Leu Lys Ala Ala Gly Val Phe Asp Pro Lys Arg Leu
130                 135                 140

Phe Gly Val Thr Thr Leu Asp Val Val Arg Ala Glu Thr Phe Thr Gln
145                 150                 155                 160

Glu Phe Ser Gly Gln Lys Asp Pro Ser Ala Val Gln Ile Pro Val Val
                165                 170                 175

Gly Gly His Ser Gly Glu Thr Ile Val Pro Leu Phe Ser Lys Thr Thr
                180                 185                 190

Pro Ala Ile Gln Ile Pro Glu Glu Lys Tyr Asp Ala Leu Ile His Arg
                195                 200                 205

Val Gln Phe Gly Gly Asp Glu Val Val Gln Ala Lys Asp Gly Ala Gly
210                 215                 220

Ser Ala Thr Leu Ser Met Ala Tyr Ala Gly Tyr Arg Phe Ala Glu Ser
225                 230                 235                 240

Val Ile Lys Ala Ser Lys Gly Gln Thr Gly Ile Val Glu Pro Thr Phe
                245                 250                 255

Val Tyr Leu Pro Gly Ile Pro Gly Gly Asp Glu Ile Val Lys Ala Thr
                260                 265                 270

Gly Val Glu Phe Phe Ser Thr Leu Val Thr Leu Gly Thr Asn Gly Ala
                275                 280                 285

Glu Lys Ala Ser Asn Val Leu Glu Gly Val Thr Glu Lys Glu Lys Lys
290                 295                 300

Leu Leu Glu Ala Cys Thr Lys Gly Leu Lys Gly Asn Ile Glu Lys Gly
305                 310                 315                 320

Ile Asp Phe Val Lys Asn Pro Pro Lys
                325                 330

<210> SEQ ID NO 21
<211> LENGTH: 35
<212> TYPE: DNA
<213> ORGANISM: Aspergillus oryzae

<400> SEQUENCE: 21
acacaactgg ccatggcctc tgccagccag gtgtg                        35

<210> SEQ ID NO 22
<211> LENGTH: 40
<212> TYPE: DNA
<213> ORGANISM: Aspergillus oryzae

<400> SEQUENCE: 22
cctcaagctc aacccctacg tttctgagct tgccctctac                   40
```

<210> SEQ ID NO 23
<211> LENGTH: 40
<212> TYPE: DNA
<213> ORGANISM: Aspergillus oryzae

<400> SEQUENCE: 23
gtagagggca agctcagaaa cgtaggggtt gagcttgagg    40

<210> SEQ ID NO 24
<211> LENGTH: 32
<212> TYPE: DNA
<213> ORGANISM: Aspergillus oryzae

<400> SEQUENCE: 24
acacaactgg ccatggcggc tccgtttcgt ca    32

<210> SEQ ID NO 25
<211> LENGTH: 45
<212> TYPE: DNA
<213> ORGANISM: Aspergillus oryzae

<400> SEQUENCE: 25
agtcacctct agttaattaa ttattacgct ttgacgatct tgcag    45

<210> SEQ ID NO 26
<211> LENGTH: 3643
<212> TYPE: DNA
<213> ORGANISM: Aspergillus oryzae

<400> SEQUENCE: 26
atggcggctc cgtttcgtca gcctgaggag gcggtcgatg acaccgagtt catcgatgac    60
caccatgaac acctccgtga taccgtgcac catcggttgc gcgccaattc ctccattatg    120
cacttccaga gatcctcgt cgccaaccgt ggtgagatcc ccattcgtat cttcagaacg    180
gcccacgagc tgtccttgca gacggttgct atctactctc atgaggatcg actgtcaatg    240
caccgtcaaa aggccgatga ggcctacatg attggccacc gcggtcagta cacccctgtc    300
ggtgcgtacc tggcgggcga tgagatcatc aagatcgccc tggagcacgg tgtccagctg    360
atccacccgg ctacggtttt cttgtccgag aacgccgact cgcccgcaa ggttgagaac    420
gccggcattg tctttgtggg acccactccc gataccattg acagcttggg tgacaaggtg    480
tcggcccgtc ggctggccat taagtgcgag gtccctgtcg ttcgggtac ggagggcccc    540
gtcgagcgct atgaggaggt caaggcgttc acagacacct atggcttccc catcatcatc    600
aaggctgcct ttggcggtgg tgccgtggt atgcgtgtgg tccgtgacca ggccgagctg    660
cgtgactcgt tcgagcgagc cacctctgag gcccgctccg ccttcggcaa tggtaccgtc    720
ttcgtcgagc gcttcctcga caaacccaag cacattgaag tccagcttct gggtgacagc    780
cacggcaacg ttgtccatct gttttgagcgt gactgctccg tgcagcgtcg tcaccagaag    840
gtcgttgagg ttgctccggc taaggacctg ccagccgatg tccgggaccg catcctggcc    900
gatgctgtga agctggccaa gtccgtcaac taccgtaacg ccggtacagc tgagttcctg    960
gtggaccagc agaaccgcca ctacttcatt gaaatcaatc ctcgtatcca agtcgagcac    1020
accatcaccg aagagattac tggtatcgat atcgtggctg cacagatcca gattgctgct    1080
ggtgcaagcc tcgagcaact gggcctgact caggaccgca tctccgcccg cggatttgcc    1140
attcaatgtc gtatcaccac ggaagatccc gccaagggt tctctccgga tactggtaag    1200
attgaggttt atcgttccgc tggtggtaac ggtgtccgtc tggatggtgg taacggtttc    1260

```
gctggtgcta tcatcacccc tcactacgac tccatgctgg tcaagtgcac ctgccgtggt    1320
tcgacctatg aaatcgctcg tcgcaaggtt gtgcgtgcct tggtcgagtt ccgtattcgt    1380
ggtgtgaaga ccaacattcc cttcctgact tcgcttctga ccacccgac cttcgtcgat    1440 ggaaactgct ggaccacttt catcgacgac accctgaat tgttctctct tgtcggcagt    1500
cagaaccgtg cccagaagct gctcgcatac ctcggcgatg tagctgtcaa cggtagtagc    1560
atcaagggcc aaattggcga gcccaagctc aaggtgatg tcatcaagcc gaagcttttc    1620
gatgccgagg gcaagccgct tgacgttttc ccccctgca ccaagggttg gaagcagatt    1680
ctggaccggg agggtccggc tgcctttgcg aaggccgtgc gtgccaacaa gggttgcttg    1740
atcatggata ctacctggcg tgacgcccac cagtctttgc tggccacccg tgtgcgtacc    1800
atcgacttgt tgaacatcgc ccatgagacc agctacgcct actccaatgc gtacagtttg    1860
gaatgctggg gtggtgctac cttcgatgtg gccatgcgtt tcctctatga ggaccctgg    1920 gaccgcctgc gcaagatgcg taaggctgtt cctaacatcc cattccagat gttgctccgt    1980
ggtgccaacg tgtcgcctct ctcttccctc ccagacaacg ccatctacca cttctgtaag    2040
caggctaaga agtgcggtgt cgacattttc cgtgttttcg acgccctcaa cgatgtcgat    2100
cagctcgagg tcggtatcaa ggctgttcat gctgccgagg gtgttgtcga ggccaccatg    2160
tgctacagcg gtgacatgct gaaccccac aagaagtaca acctggagta ctacatggcc    2220
ttggtggata agattgtagc catgaagcct cacatccttg gtatcaagga tatggccggt    2280
gtgctgaagc ccaggccgc tcgcctgttg gtgggctcca tccgtcagcg ctaccctgac    2340
cttcccatcc acgtccacac ccacgactcc gctggtactg gtgtagcttc catgattgcc    2400
tgtgcccagg cgggtgccga cgccgtggac gccgcgaccg acagcatgtc cggtatgacc    2460
tcccagccta gcattggtgc cattctggcc tctcttgagg gcactgagca agaccccggt    2520
ctcaacctcg cccacgtgcg cgctattgat agctactggg cacagctgcg cttgctctac    2580
tctcctttcg aggcgggtct cactggcccc gaccctgagg tctacgagca cgagatccct    2640
ggtggtcagt tgaccaacct tatcttccag gccagtcagc tcggcttggg ccagcagtgg    2700
gccgaaacca agaaggccta tgaggcggct aatgatttac tcggcgacat tgtaaaggtc    2760
actcccacct ccaaggtggt cggtgacttg gctcagttca tggtctcgaa caaactgact    2820
ccagaggatg ttgttgagcg tgctggtgag ctggacttcc ctggttctgt gctcgaattc    2880
ctcgaaggtc tcatgggaca gcccttcggt ggattcccg agccattgcg ctcccgcgcc    2940
ctgcgcgatc gccgcaagct cgagaagcgt ccaggtctct acctcgagcc tttggatttg    3000
gctaagatca agagccagat ccgtgagaag ttcggtgctg ctactgagta tgacgtggcc    3060
agctatgcca tgtatcccaa ggtcttcgag gactacaaga agttcgtcca gaagttcggt    3120
gatctctccg tcttgcccac acggtacttc ttggccaagc ctgagattgg cgaggagttc    3180
cacgttgagc tggagaaggg taaggtgctc atcctgaagt tgttggccat cggccctctt    3240
tcagagcaga ctggtcagcg tgaggtcttc tacgaagtca acggtgaggt gcgccaggtc    3300
gctgttgatg acaacaaggc ttccgtggac aacacttcac gccctaaggc cgatgtgggt    3360
gacagcagcc aggtcggtgc tcctatgagc ggtgtggttg ttgaaatccg tgtccacgat    3420
ggtctggagg ttaagaaggg tgacccactt gccgtcctga gtgccatgaa gatggtaagt    3480
tcattccgaa tcattttct cactggtcaa ctacagatgc taacagctta tccaggaaat    3540
ggttatctct gctcctcaca gtggaaaggt ctccagcttg ctggtcaagg agggcgattc    3600
tgtggatggc caggatctcg tctgcaagat cgtcaaagcg taa                      3643
```

```
<210> SEQ ID NO 27
<211> LENGTH: 1193
<212> TYPE: PRT
<213> ORGANISM: Aspergillus oryzae

<400> SEQUENCE: 27
```

| | | | | | | | | | | | | | | |
|---|---|---|---|---|---|---|---|---|---|---|---|---|---|---|
| Met | Ala | Ala | Pro | Phe | Arg | Gln | Pro | Glu | Glu | Ala | Val | Asp | Asp | Thr | Glu |
| 1 | | | | 5 | | | | | 10 | | | | | 15 | |
| Phe | Ile | Asp | Asp | His | His | Glu | His | Leu | Arg | Asp | Thr | Val | His | His | Arg |
| | | | 20 | | | | | 25 | | | | | 30 | | |
| Leu | Arg | Ala | Asn | Ser | Ser | Ile | Met | His | Phe | Gln | Lys | Ile | Leu | Val | Ala |
| | | 35 | | | | | 40 | | | | | 45 | | | |
| Asn | Arg | Gly | Glu | Ile | Pro | Ile | Arg | Ile | Phe | Arg | Thr | Ala | His | Glu | Leu |
| | 50 | | | | | 55 | | | | | 60 | | | | |
| Ser | Leu | Gln | Thr | Val | Ala | Ile | Tyr | Ser | His | Glu | Asp | Arg | Leu | Ser | Met |
| 65 | | | | | 70 | | | | | 75 | | | | | 80 |
| His | Arg | Gln | Lys | Ala | Asp | Glu | Ala | Tyr | Met | Ile | Gly | His | Arg | Gly | Gln |
| | | | | 85 | | | | | 90 | | | | | 95 | |
| Tyr | Thr | Pro | Val | Gly | Ala | Tyr | Leu | Ala | Gly | Asp | Glu | Ile | Ile | Lys | Ile |
| | | | 100 | | | | | 105 | | | | | 110 | | |
| Ala | Leu | Glu | His | Gly | Val | Gln | Leu | Ile | His | Pro | Gly | Tyr | Gly | Phe | Leu |
| | | 115 | | | | | 120 | | | | | 125 | | | |
| Ser | Glu | Asn | Ala | Asp | Phe | Ala | Arg | Lys | Val | Glu | Asn | Ala | Gly | Ile | Val |
| | 130 | | | | | 135 | | | | | 140 | | | | |
| Phe | Val | Gly | Pro | Thr | Pro | Asp | Thr | Ile | Asp | Ser | Leu | Gly | Asp | Lys | Val |
| 145 | | | | | 150 | | | | | 155 | | | | | 160 |
| Ser | Ala | Arg | Arg | Leu | Ala | Ile | Lys | Cys | Glu | Val | Pro | Val | Val | Pro | Gly |
| | | | | 165 | | | | | 170 | | | | | 175 | |
| Thr | Glu | Gly | Pro | Val | Glu | Arg | Tyr | Glu | Glu | Val | Lys | Ala | Phe | Thr | Asp |
| | | | 180 | | | | | 185 | | | | | 190 | | |
| Thr | Tyr | Gly | Phe | Pro | Ile | Ile | Ile | Lys | Ala | Ala | Phe | Gly | Gly | Gly | Gly |
| | | 195 | | | | | 200 | | | | | 205 | | | |
| Arg | Gly | Met | Arg | Val | Val | Arg | Asp | Gln | Ala | Glu | Leu | Arg | Asp | Ser | Phe |
| | 210 | | | | | 215 | | | | | 220 | | | | |
| Glu | Arg | Ala | Thr | Ser | Glu | Ala | Arg | Ser | Ala | Phe | Gly | Asn | Gly | Thr | Val |
| 225 | | | | | 230 | | | | | 235 | | | | | 240 |
| Phe | Val | Glu | Arg | Phe | Leu | Asp | Lys | Pro | Lys | His | Ile | Glu | Val | Gln | Leu |
| | | | | 245 | | | | | 250 | | | | | 255 | |
| Leu | Gly | Asp | Ser | His | Gly | Asn | Val | Val | His | Leu | Phe | Glu | Arg | Asp | Cys |
| | | | 260 | | | | | 265 | | | | | 270 | | |
| Ser | Val | Gln | Arg | Arg | His | Gln | Lys | Val | Val | Glu | Val | Ala | Pro | Ala | Lys |
| | | 275 | | | | | 280 | | | | | 285 | | | |
| Asp | Leu | Pro | Ala | Asp | Val | Arg | Asp | Arg | Ile | Leu | Ala | Asp | Ala | Val | Lys |
| | 290 | | | | | 295 | | | | | 300 | | | | |
| Leu | Ala | Lys | Ser | Val | Asn | Tyr | Arg | Asn | Ala | Gly | Thr | Ala | Glu | Phe | Leu |
| 305 | | | | | 310 | | | | | 315 | | | | | 320 |
| Val | Asp | Gln | Gln | Asn | Arg | His | Tyr | Phe | Ile | Glu | Ile | Asn | Pro | Arg | Ile |
| | | | | 325 | | | | | 330 | | | | | 335 | |
| Gln | Val | Glu | His | Thr | Ile | Thr | Glu | Glu | Ile | Thr | Gly | Ile | Asp | Ile | Val |
| | | | 340 | | | | | 345 | | | | | 350 | | |
| Ala | Ala | Gln | Ile | Gln | Ile | Ala | Ala | Gly | Ala | Ser | Leu | Glu | Gln | Leu | Gly |
| | | 355 | | | | | 360 | | | | | 365 | | | |
| Leu | Thr | Gln | Asp | Arg | Ile | Ser | Ala | Arg | Gly | Phe | Ala | Ile | Gln | Cys | Arg |
| | 370 | | | | | 375 | | | | | 380 | | | | |

```
Ile Thr Thr Glu Asp Pro Ala Lys Gly Phe Ser Pro Asp Thr Gly Lys
385                 390                 395                 400

Ile Glu Val Tyr Arg Ser Ala Gly Gly Asn Gly Val Arg Leu Asp Gly
            405                 410                 415

Gly Asn Gly Phe Ala Gly Ala Ile Ile Thr Pro His Tyr Asp Ser Met
        420                 425                 430

Leu Val Lys Cys Thr Cys Arg Gly Ser Thr Tyr Glu Ile Ala Arg Arg
    435                 440                 445

Lys Val Val Arg Ala Leu Val Glu Phe Arg Ile Arg Gly Val Lys Thr
    450                 455                 460

Asn Ile Pro Phe Leu Thr Ser Leu Leu Ser His Pro Thr Phe Val Asp
465                 470                 475                 480

Gly Asn Cys Trp Thr Thr Phe Ile Asp Asp Thr Pro Glu Leu Phe Ser
                485                 490                 495

Leu Val Gly Ser Gln Asn Arg Ala Gln Lys Leu Leu Ala Tyr Leu Gly
            500                 505                 510

Asp Val Ala Val Asn Gly Ser Ser Ile Lys Gly Gln Ile Gly Glu Pro
        515                 520                 525

Lys Leu Lys Gly Asp Val Ile Lys Pro Lys Leu Phe Asp Ala Glu Gly
    530                 535                 540

Lys Pro Leu Asp Val Ser Ala Pro Cys Thr Lys Gly Trp Lys Gln Ile
545                 550                 555                 560

Leu Asp Arg Glu Gly Pro Ala Ala Phe Ala Lys Ala Val Arg Ala Asn
                565                 570                 575

Lys Gly Cys Leu Ile Met Asp Thr Thr Trp Arg Asp Ala His Gln Ser
            580                 585                 590

Leu Leu Ala Thr Arg Val Arg Thr Ile Asp Leu Leu Asn Ile Ala His
        595                 600                 605

Glu Thr Ser Tyr Ala Tyr Ser Asn Ala Tyr Ser Leu Glu Cys Trp Gly
    610                 615                 620

Gly Ala Thr Phe Asp Val Ala Met Arg Phe Leu Tyr Glu Asp Pro Trp
625                 630                 635                 640

Asp Arg Leu Arg Lys Met Arg Lys Ala Val Pro Asn Ile Pro Phe Gln
                645                 650                 655

Met Leu Leu Arg Gly Ala Asn Gly Val Ala Tyr Ser Ser Leu Pro Asp
            660                 665                 670

Asn Ala Ile Tyr His Phe Cys Lys Gln Ala Lys Lys Cys Gly Val Asp
        675                 680                 685

Ile Phe Arg Val Phe Asp Ala Leu Asn Asp Val Asp Gln Leu Glu Val
    690                 695                 700

Gly Ile Lys Ala Val His Ala Ala Glu Gly Val Val Glu Ala Thr Met
705                 710                 715                 720

Cys Tyr Ser Gly Asp Met Leu Asn Pro His Lys Lys Tyr Asn Leu Glu
                725                 730                 735

Tyr Tyr Met Ala Leu Val Asp Lys Ile Val Ala Met Lys Pro His Ile
            740                 745                 750

Leu Gly Ile Lys Asp Met Ala Gly Val Leu Lys Pro Gln Ala Ala Arg
        755                 760                 765

Leu Leu Val Gly Ser Ile Arg Gln Arg Tyr Pro Asp Leu Pro Ile His
    770                 775                 780

Val His Thr His Asp Ser Ala Gly Thr Gly Val Ala Ser Met Ile Ala
785                 790                 795                 800

Cys Ala Gln Ala Gly Ala Asp Ala Val Asp Ala Ala Thr Asp Ser Met
```

```
                      805                 810                 815
Ser Gly Met Thr Ser Gln Pro Ser Ile Gly Ala Ile Leu Ala Ser Leu
            820                 825                 830

Glu Gly Thr Glu Gln Asp Pro Gly Leu Asn Leu Ala His Val Arg Ala
            835                 840                 845

Ile Asp Ser Tyr Trp Ala Gln Leu Arg Leu Leu Tyr Ser Pro Phe Glu
            850                 855                 860

Ala Gly Leu Thr Gly Pro Asp Pro Glu Val Tyr Glu His Glu Ile Pro
865                 870                 875                 880

Gly Gly Gln Leu Thr Asn Leu Ile Phe Gln Ala Ser Gln Leu Gly Leu
                885                 890                 895

Gly Gln Gln Trp Ala Glu Thr Lys Lys Ala Tyr Glu Ala Ala Asn Asp
                900                 905                 910

Leu Leu Gly Asp Ile Val Lys Val Thr Pro Thr Ser Lys Val Val Gly
                915                 920                 925

Asp Leu Ala Gln Phe Met Val Ser Asn Lys Leu Thr Pro Glu Asp Val
            930                 935                 940

Val Glu Arg Ala Gly Glu Leu Asp Phe Pro Gly Ser Val Leu Glu Phe
945                 950                 955                 960

Leu Glu Gly Leu Met Gly Gln Pro Phe Gly Gly Phe Pro Glu Pro Leu
                965                 970                 975

Arg Ser Arg Ala Leu Arg Asp Arg Arg Lys Leu Glu Lys Arg Pro Gly
                980                 985                 990

Leu Tyr Leu Glu Pro Leu Asp Leu Ala Lys Ile Lys Ser Gln Ile Arg
                995                1000                1005

Glu Lys Phe Gly Ala Ala Thr Glu Tyr Asp Val Ala Ser Tyr Ala
           1010                1015                1020

Met Tyr Pro Lys Val Phe Glu Asp Tyr Lys Lys Phe Val Gln Lys
           1025                1030                1035

Phe Gly Asp Leu Ser Val Leu Pro Thr Arg Tyr Phe Leu Ala Lys
           1040                1045                1050

Pro Glu Ile Gly Glu Glu Phe His Val Glu Leu Glu Lys Gly Lys
           1055                1060                1065

Val Leu Ile Leu Lys Leu Leu Ala Ile Gly Pro Leu Ser Glu Gln
           1070                1075                1080

Thr Gly Gln Arg Glu Val Phe Tyr Glu Val Asn Gly Glu Val Arg
           1085                1090                1095

Gln Val Ala Val Asp Asp Asn Lys Ala Ser Val Asp Asn Thr Ser
           1100                1105                1110

Arg Pro Lys Ala Asp Val Gly Asp Ser Ser Gln Val Gly Ala Pro
           1115                1120                1125

Met Ser Gly Val Val Glu Ile Arg Val His Asp Gly Leu Glu
           1130                1135                1140

Val Lys Lys Gly Asp Pro Leu Ala Val Leu Ser Ala Met Lys Met
           1145                1150                1155

Glu Met Val Ile Ser Ala Pro His Ser Gly Lys Val Ser Ser Leu
           1160                1165                1170

Leu Val Lys Glu Gly Asp Ser Val Asp Gly Gln Asp Leu Val Cys
           1175                1180                1185

Lys Ile Val Lys Ala
           1190

<210> SEQ ID NO 28
<211> LENGTH: 36
```

```
<212> TYPE: DNA
<213> ORGANISM: Aspergillus oryzae

<400> SEQUENCE: 28
agaacatcgt ccataatggt caaagctggt gagtta                                36

<210> SEQ ID NO 29
<211> LENGTH: 40
<212> TYPE: DNA
<213> ORGANISM: Aspergillus oryzae

<400> SEQUENCE: 29
gtgtcagtca cctctagtta ttactttggt ggtgggttct                            40

<210> SEQ ID NO 30
<211> LENGTH: 36
<212> TYPE: DNA
<213> ORGANISM: Aspergillus oryzae

<400> SEQUENCE: 30
tagaacatcg tccataatgg cggctccgtt tcgtca                                36

<210> SEQ ID NO 31
<211> LENGTH: 40
<212> TYPE: DNA
<213> ORGANISM: Aspergillus oryzae

<400> SEQUENCE: 31
gtgtcagtca cctctagtta ttattacgct ttgacgatct                            40

<210> SEQ ID NO 32
<211> LENGTH: 20
<212> TYPE: DNA
<213> ORGANISM: Aspergillus oryzae

<400> SEQUENCE: 32
ggaaacgtca agcggcttgc                                                  20

<210> SEQ ID NO 33
<211> LENGTH: 1182
<212> TYPE: DNA
<213> ORGANISM: Aspergillus terreus

<400> SEQUENCE: 33
atgtttgaga acactgcccc tccagggagc tcccgctccg actctggcat cctggaccat      60
gaattcgaga agcagccggg ttccgtgggc atgcgtgaac gcatccgcca ttttacctgg     120
gcctggtata ctctcacaat gagtgctggt ggcttggccc tcctccttgg gagccagcca     180
aacaccttca ccggcctgag ggagattgga ctcgccgtgt acctgctcaa cctgctcttc     240
tttgccctgg tctgctcgac catggccggc cggttcatcc tgcacggagg ctggtcgac      300 tctctccggc acgaacgcga gggcatcttc ttcccaacct ctggctctc gatcgccacc      360 atcatcacag gcctgtaccg ctacttcggc gaagacgccg acgcccctt cgtgctcgcc      420 ctcgaagccc tcttctggat ctactgcgct tgcaccctcc tcgtcgccgt catccaatac     480
tcctggctct tctccggccc caaataccgc ctccaaaccg ccatgccgg ctggatcctc      540 cccgccttcc ctgtcatgct ctctggcacc atcgcctccg tcatcgccga gcagcagcca     600
gcccgcgccg ccatccccat catcgtcggc ggcaccacct tccagggcct gggcttctcc     660
atcagcatga tcatgtacgc ccactacgtc ggccgcctca tggagtccgg cctgccgtgc     720
cgcgagcacc gcccgggcat gttcatcgcc gtcgccgcgc cggctttcac ggcgctggcc     780
```

-continued

```
ctcgtcggca tgaccaaggg gctcccgcac gacttccagc tcatcggcga tgacttcgcc    840
ttcgaggatg cccgcatcct gcagctgctg gcgatcgccg tcggcgtgtt tctctgggcg    900
ctgagtctgt ggttcttttg cattgcggcc attgccgtcg tgcgctcccc gccaacggcc    960
ttccacctga gctggtgggc catggtcttc cccaacacgg gcttcaccct cgccacgatc   1020
aacctgggta cggccctcaa gagcgagggt atccagggtg tggggacggc catgtcgatt   1080
ggaattgtgt ctatttctt gtttgtgttt atcagccatg tgcgggctgt catcaggaaa   1140
gacattatgt atcctgggaa agacgaggat gtggtggagt aa                      1182
```

<210> SEQ ID NO 34
<211> LENGTH: 393
<212> TYPE: PRT
<213> ORGANISM: Aspergillus terreus

<400> SEQUENCE: 34

```
Met Phe Glu Asn Thr Ala Pro Pro Gly Ser Ser Arg Ser Asp Ser Gly
  1               5                  10                  15

Ile Leu Asp His Glu Phe Glu Lys Gln Pro Gly Ser Val Gly Met Arg
             20                  25                  30

Glu Arg Ile Arg His Phe Thr Trp Ala Trp Tyr Thr Leu Thr Met Ser
         35                  40                  45

Ala Gly Gly Leu Ala Leu Leu Gly Ser Gln Pro Asn Thr Phe Thr
     50                  55                  60

Gly Leu Arg Glu Ile Gly Leu Ala Val Tyr Leu Leu Asn Leu Phe
 65                  70                  75                  80

Phe Ala Leu Val Cys Ser Thr Met Ala Gly Arg Phe Ile Leu His Gly
                 85                  90                  95

Gly Leu Val Asp Ser Leu Arg His Glu Arg Glu Gly Ile Phe Phe Pro
            100                 105                 110

Thr Phe Trp Leu Ser Ile Ala Thr Ile Thr Gly Leu Tyr Arg Tyr
        115                 120                 125

Phe Gly Glu Asp Ala Gly Arg Pro Phe Val Leu Ala Leu Glu Ala Leu
    130                 135                 140

Phe Trp Ile Tyr Cys Ala Cys Thr Leu Leu Val Ala Val Ile Gln Tyr
145                 150                 155                 160

Ser Trp Leu Phe Ser Gly Pro Lys Tyr Arg Leu Gln Thr Ala Met Pro
                165                 170                 175

Gly Trp Ile Leu Pro Ala Phe Pro Val Met Leu Ser Gly Thr Ile Ala
            180                 185                 190

Ser Val Ile Ala Glu Gln Gln Pro Ala Arg Ala Ala Ile Pro Ile Ile
        195                 200                 205

Val Ala Gly Thr Thr Phe Gln Gly Leu Gly Phe Ser Ile Ser Met Ile
    210                 215                 220

Met Tyr Ala His Tyr Val Gly Arg Leu Met Glu Ser Gly Leu Pro Cys
225                 230                 235                 240

Arg Glu His Arg Pro Gly Met Phe Ile Ala Val Gly Pro Pro Ala Phe
                245                 250                 255

Thr Ala Leu Ala Leu Val Gly Met Thr Lys Gly Leu Pro His Asp Phe
            260                 265                 270

Gln Leu Ile Gly Asp Asp Phe Ala Phe Glu Asp Ala Arg Ile Leu Gln
        275                 280                 285

Leu Leu Ala Ile Ala Val Gly Val Phe Leu Trp Ala Leu Ser Leu Trp
    290                 295                 300
```

```
Phe Phe Cys Ile Ala Ala Ile Ala Val Val Arg Ser Pro Pro Thr Ala
305                 310                 315                 320

Phe His Leu Ser Trp Trp Ala Met Val Phe Pro Asn Thr Gly Phe Thr
            325                 330                 335

Leu Ala Thr Ile Asn Leu Gly Thr Ala Leu Lys Ser Glu Gly Ile Gln
                340                 345                 350

Gly Val Gly Thr Ala Met Ser Ile Gly Ile Val Ser Ile Phe Leu Phe
            355                 360                 365

Val Phe Ile Ser His Val Arg Ala Val Ile Arg Lys Asp Ile Met Tyr
370                 375                 380

Pro Gly Lys Asp Glu Asp Val Val Glu
385                 390

<210> SEQ ID NO 35
<211> LENGTH: 1317
<212> TYPE: DNA
<213> ORGANISM: Schizosaccharomyces pombe

<400> SEQUENCE: 35
atgggagaat tgaaggaaat tctcaagcag cgctaccatg aattgctcga ctggaacgtc      60
aaagcacccc acgtccctct ctcgcagagg ttgaagcatt tcacatggtc gtggttcgcg     120
tgtacgatgg caaccggtgg cgtcggactc atcatcggat ccttcccttt ccgattctac     180
ggactcaaca cgatcggcaa gattgtgtac atcctccaga ttttcctctt ctccttgttc     240
ggctcgtgta tgctcttcag gttcatcaag tatccgtcca caatcaagga ctcctggaac     300
catcatctcg agaaactctt cattgcgact tgtctcctct cgatttcgac attcatcgat     360
atgttggcga tctacgccta ccccgacaca ggcgagtgga tggtgtgggt catccgaatc     420
ctctactaca tctacgtcgc ggtctccttc atttactgtg tgatggcgtt cttcacgatc     480
ttcaacaacc acgtctatac cattgaaacc gcctcgcctg catggatcct ccctatcttc     540
cctccgatga tctgtggtgt cattgccggt gcggtgaact ccacccagcc tgcgcaccag     600
ctcaaaaaca tggtgatttt cggaatcctc ttccagggat tgggtttctg ggtctacttg     660
ctcttgttcg cagtcaacgt gctccggttc ttcacggtcg gcttggcaaa gcccaggac     720
cgacctggca tgttcatgtt cgtgggacct cctgcgttct ccggcttggc actcatcaac     780
atcgcgaggg tgccatgggc tcgaggccg tacatcttcg tgggagcaaa ctcctcggaa     840
tacttgggtt tcgtgtcgac gttcatggcg attttcatct ggggcttggc agcatggtgt     900
tattgtctcg ccatggtgtc cttcctcgca ggcttcttca cacgcgcacc tttgaagttc     960
gcgtgtggtt ggttcgcatt catcttcccc aacgtgggct tcgtgaactg tacgattgag    1020
atcggcaaga tgatcgactc caaagccttc cagatgttcg ccacattat cggtgtcatc    1080
ctctgtatcc agtggatttt gctcatgtat ttgatggtgc gtgcgttctt ggtcaacgac    1140
ttgtgttatc ccgtaaaga cgaggacgcc atccgcctc ccaaacccaa cacaggcgtc    1200
ctcaaccca ccttccctcc cgaaaaagca cctgcctccc tcgaaaaagt cgatacacat    1260
gtcacttcca ctggcggaga gtcggatcct ccgtcctccg aacacgagtc ggtctaa       1317

<210> SEQ ID NO 36
<211> LENGTH: 438
<212> TYPE: PRT
<213> ORGANISM: Schizosaccharomyces pombe

<400> SEQUENCE: 36

Met Gly Glu Leu Lys Glu Ile Leu Lys Gln Arg Tyr His Glu Leu Leu
1               5                   10                  15
```

```
Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
                100                 105                 110

Leu Ser Ile Ser Thr Phe Ile Asp Met Leu Ala Ile Tyr Ala Tyr Pro
                115                 120                 125

Asp Thr Gly Glu Trp Met Val Trp Val Ile Arg Ile Leu Tyr Tyr Ile
130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
                180                 185                 190

Asn Ser Thr Gln Pro Ala His Gln Leu Lys Asn Met Val Ile Phe Gly
                195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
                260                 265                 270

Phe Val Gly Ala Asn Ser Ser Glu Tyr Leu Gly Phe Val Ser Thr Phe
                275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
                340                 345                 350

Phe Gly His Ile Ile Gly Val Ile Leu Cys Ile Gln Trp Ile Leu Leu
                355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
                420                 425                 430

Ser Glu His Glu Ser Val
```

-continued

```
<210> SEQ ID NO 37
<211> LENGTH: 1317
<212> TYPE: DNA
<213> ORGANISM: Schizosaccharomyces pombe

<400> SEQUENCE: 37
atgggtgaac tcaaggaaat cttgaaacag aggtatcatg agttgcttga ctggaatgtc      60
aaagcccctc atgtccctct cagtcaacga ctgaagcatt ttacatggtc ttggtttgca     120
tgtactatgg caactggtgg tgttggtttg attattggtt ctttcccctt tcgattttat     180
ggtcttaata caattggcaa aattgtttat attcttcaaa tcttttttgtt ttctctcttt    240 ggatcatgca tgcttttttcg ctttattaaa tatccttcaa ctatcaagga ttcctggaac    300
catcatttgg aaaagctttt cattgctact tgtcttcttt caatatccac gttcatcgac    360
atgcttgcca tatacgccta tcctgatacc ggcgagtgga tggtgtgggt cattcgaatc    420
ctttattaca tttacgttgc agtatccttt atatactgcg taatggcttt ttttacaatt    480
ttcaacaacc atgtatatac cattgaaacc gcatctcctg cttggattct tcctattttc    540
cctcctatga tttgtggtgt cattgctggc gccgtcaatt ctacacaacc cgctcatcaa    600
ttaaaaaata tggttatctt tggtatcctc tttcaaggac ttggtttttg ggtttatctt    660
ttactgtttg ccgtcaatgt cttacggttt tttactgtag gcctggcaaa accccaagat    720
cgacctggta tgtttatgtt tgtcggtcca ccagctttct caggtttggc cttaattaat    780
attgcgcgtg gtgctatggg cagtcgccct tatattttg ttggcgccaa ctcatccgag    840
tatcttggtt ttgttctac ctttatggct atttttattt ggggtcttgc tgcttggtgt    900
tactgtctcg ccatggttag cttttttagcg ggcttttttca ctcgagcccc tctcaagttt    960
gcttgtggat ggtttgcatt cattttcccc aacgtgggtt ttgttaattg taccattgag   1020
ataggtaaaa tgatagattc caaagctttc caaatgtttg acatatcat tggggtcatt   1080 ctttgtattc agtggatcct cctaatgtat ttaatggtcc gtgcgtttct cgtcaatgat   1140 cttttgctatc ctggcaaaga cgaagatgcc atcctccac caaaaccaaa tacaggtgtc   1200
cttaacccta ccttcccacc tgaaaaagca cctgcatctt tggaaaaagt cgatacacat   1260
gtcacatcta ctggtggtga atcggatcct cctagtagtg aacatgaaag cgtttaa       1317

<210> SEQ ID NO 38
<211> LENGTH: 42
<212> TYPE: DNA
<213> ORGANISM: Aspergillus terreus

<400> SEQUENCE: 38
gtgtgataga acatcgtcca taatgtttga gaacactgcc cc                           42

<210> SEQ ID NO 39
<211> LENGTH: 44
<212> TYPE: DNA
<213> ORGANISM: Aspergillus terreus

<400> SEQUENCE: 39
gtcagtcacc tctagttaat taattactcc accacatcct cgtc                         44

<210> SEQ ID NO 40
<211> LENGTH: 36
<212> TYPE: DNA
<213> ORGANISM: Schizosaccharomyces pombe
```

```
<400> SEQUENCE: 40
gaacatcgtc cataatggga gaattgaagg aaattc                                36

<210> SEQ ID NO 41
<211> LENGTH: 40
<212> TYPE: DNA
<213> ORGANISM: Schizosaccharomyces pombe

<400> SEQUENCE: 41
ggtgtcagtc acctctagtt attattagac cgactcgtgt                            40
```

METHODS FOR IMPROVING MALIC ACID PRODUCTION IN FILAMENTOUS FUNGI

CROSS REFERENCE TO RELATED APPLICATIONS

This application claims priority benefit of U.S. Provisional Application No. 61/238,962, filed Sep. 1, 2009; U.S. Provisional Application No. 61/327,224, filed Apr. 23, 2010; and U.S. Application No. 61/356,971, filed Jun. 21, 2010. The entire contents of those applications are hereby incorporated by reference herein.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods for improving C4 dicarboxylic acid production in filamentous fungi.

2. Description of the Related Art

Organic acids have a long history of commercial use in a variety of industries. For example, organic acids are used in the food and feed industries (citric acid, ascorbic acid, lactic acid, acetic acid, and gluconic acid) as monomers for the production of various polymers (adipic acid, lactic acid, acrylic acid, and itaconic acid), as metal chelators (gluconic acid), and as "green" solvents (acetic acid) (Sauer et al., 2008, *Trends in Biotechnology* 26: 100-108). Organic acids may themselves be commercial products or they may be chemical building blocks used in the manufacture of other chemicals. In addition to specialty applications, it has long been recognized that C4 dicarboxylic acids can also serve as building block compounds for the production of large volume industrial chemicals, such as 1,4-butanediol, tetrahydrofuran, and gamma-butyrolactone. The cost of producing these large volume industrial chemicals by traditional petrochemical routes has increased significantly due to the high cost of petroleum derived building blocks.

Organic acids are produced commercially either by chemical synthesis from petroleum derived feedstocks (e.g., fumaric acid, malic acid, acrylic acid, and adipic acid) or by microbial fermentation (e.g., citric acid, lactic acid, gluconic acid, and itaconic acid). Some organic acids such as fumaric acid and malic acid can also be produced by microbial fermentation, but are currently produced commercially by chemical synthesis from petrochemical feedstocks due to lower production costs. However, the rising cost of petroleum derived building block chemicals, the geopolitical instability affecting crude oil prices, and the desire to implement manufacturing processes that utilize feedstocks derived from renewable resources have stimulated a renewed interest in producing organic acids and other chemicals by microbial fermentation.

While malic acid is produced commercially today by chemical synthesis from petrochemical feedstocks, it can also be produced by microbial fermentation. Malic acid has been produced at high levels in genetically engineered yeast (*Saccharomyces cerevisiae*) (Zelle et al., 2008, *Appl. Environ. Microbiol.* 74: 2766-2777) and naturally occurring filamentous fungi such as *Aspergillus* spp. (U.S. Pat. No. 3,063,910; Bercovitz et al., 1990, *Appl. Environ. Microbiol.* 56: 1594-1597). Abe et al. (U.S. Pat. No. 3,063,910) and Bercovitz et al. (1990, *Appl. Environ. Microbiol.* 56: 1594-1597) reported high levels of malic acid production in several species of *Aspergillus*. Moreover, Battat et al. (1991, *Biotechnol. Bioengineering* 37: 1108-1116) reported malic acid production as high as 113 g/L by *Aspergillus flavus* in a stirred fermentor under optimized conditions. Dicarboxylic acid production by microbial fermentation in yeast is described in WO 2010/003728. Malic acid production by microbial fermentation is also described in WO 2009/011974 and WO 2009/155382. Improvement of malic acid production by genetic engineering of *Aspergillus* will enable economical commercial malic acid production by fermentation.

Malic acid overproduction in *Aspergillus* spp. occurs under specific culture conditions (aerobic conditions and high C:N ratio; calcium carbonate is also added as a neutralizing agent and as source of $CO_2$ for malic acid biosynthesis). Under these conditions, overflow metabolism via the cytosolic, reductive tricarboxylic acid (TCA) cycle results in increased malic acid biosynthesis and secretion into the culture medium. Increased malic acid production has been reported in *Saccharomyces cerevisiae* by increasing the level of pyruvate carboxylase (Bauer et al., 1999, *FEMS Microbiol Lett.* 179: 107-113) or malate dehydrogenase (Pines et al., 1997, *Appl. Microbiol. Biotechnol.* 48: 248-255) using genetic engineering and increasing expression of a malic acid transporter (Zelle et al., 2008, supra. It has been suggested, based on biochemical evidence, that malate dehydrogenase activity is limiting malic acid production in *Aspergillus flavus* strain ATCC 13697 (Peleg et al., 1988, *Appl. Microbiol. Biotechnol.* 28: 69-75). However, no direct improvement in malic acid production has been shown in *Aspergillus* as a result of genetic engineering using recombinant DNA techniques.

The present invention relates to methods for improving C4 dicarboxylic acid production, such as malic acid production, in filamentous fungi.

SUMMARY OF THE INVENTION

The present invention relates to methods of producing a C4 dicarboxylic acid (e.g., malic acid), comprising: (a) cultivating a filamentous fungal host cell comprising one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase; wherein the filamentous fungal host cell secretes (or is capable of secreting) increased levels of the C4 dicarboxylic acid compared to the filamentous fungal host cell without the one or more (several) heterologous polynucleotides encoding the C4 dicarboxylic acid transporter, the malate dehydrogenase, and the pyruvate carboxylase when cultivated under the same conditions; and (b) recovering the C4 dicarboxylic acid.

The present invention also relates to methods for increasing C4 dicarboxylic acid production (e.g., malic acid production) relative to a parent host cell, comprising: (a) transforming into a filamentous fungal host cell one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase, wherein the filamentous fungal host cell secretes (or is capable of secreting) increased levels of the C4 dicarboxylic acid compared to the filamentous fungal host cell without the one or more (several) heterologous polynucleotides encoding the C4 dicarboxylic acid transporter, the malate dehydrogenase, and the pyruvate carboxylase when cultivated under the same conditions; (b) cultivating the transformed filamentous fungal host cell in a medium; and (c) recovering the C4 dicarboxylic acid.

The present invention also relates to filamentous fungal host cells, comprising one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase, wherein the filamentous fungal host cells secrete increased levels of a C4 dicarboxylic acid (e.g., malic acid) compared to the filamentous fungal host cells without the one or more (several) heterologous polynucleotides encoding the C4 dicarboxylic acid transporter, the malate dehydrogenase, and the pyruvate carboxylase when cultivated under the same conditions.

In one aspect, the heterologous second polynucleotide encodes a variant of a parent malate dehydrogenase comprising (i) a deletion at positions equivalent to positions 2 to 17 or a portion thereof of SEQ ID NO: 18, and (ii) a substitution at a position equivalent to position 48 of SEQ ID NO: 18; wherein the deletion and the substitution reduce mitochondrial import in vivo of the malate dehydrogenase variant thereby increasing the level of the malate dehydrogenase variant in the cytosol, and wherein the filamentous fungal host cell secretes (or is capable of secreting) increased levels of the malic acid compared to the filamentous fungal host cell without the polynucleotide encoding the malate dehydrogenase variant when cultivated under the same conditions.

The present invention also relates to variants of a parent malate dehydrogenase comprising (i) a deletion at positions equivalent to positions 2 to 17 or a portion thereof of SEQ ID NO: 18, and (ii) a substitution at a position equivalent to position 48 of SEQ ID NO: 18, wherein the variant has malate dehydrogenase activity.

The present invention also relates to isolated polynucleotides encoding the malate dehydrogenase variants, and nucleic acid constructs, vectors, and host cells comprising the polynucleotides.

BRIEF DESCRIPTION OF THE FIGURES

FIG. 3 shows the genomic DNA sequence and the deduced amino acid sequence of an *Aspergillus oryzae* NRRL 3488 C4 dicarboxylic acid transporter gene (mae3) (SEQ ID NOs: 7 and 8, respectively).
FIG. 5 shows the genomic DNA sequence and the deduced amino acid sequence of an *Aspergillus oryzae* NRRL 3488 malate dehydrogenase 1 gene (mdh1) (SEQ ID NOs: 17 and 18, respectively).
FIG. 7 shows the genomic DNA sequence and the deduced amino acid sequence of an *Aspergillus oryzae* NRRL 3488 malate dehydrogenase 3 gene (mdh3) (SEQ ID NOs: 19 and 20, respectively).
FIGS. 9A and 9B show the genomic DNA sequence and the deduced amino acid sequence of an *Aspergillus oryzae* NRRL 3488 pyruvate carboxylase gene (pyc) (SEQ ID NOs: 26 and 27, respectively).

FIG. 13 shows the genomic DNA sequence and the deduced amino acid sequence of an *Aspergillus terreus* C4 dicarboxylic acid transporter gene (atc4t) (SEQ ID NOs: 33 and 34, respectively).
FIGS. 16A and 16B show the genomic codon-optimized DNA sequence (CO), the deduced amino acid sequence, and the genomic wild-type DNA sequence (WT) of a *Schizosaccharomyces pombe* C4 dicarboxylic acid transporter gene (mae1) (SEQ ID NOs: 35, 36, and 37, respectively).

DEFINITIONS

Figure 1:
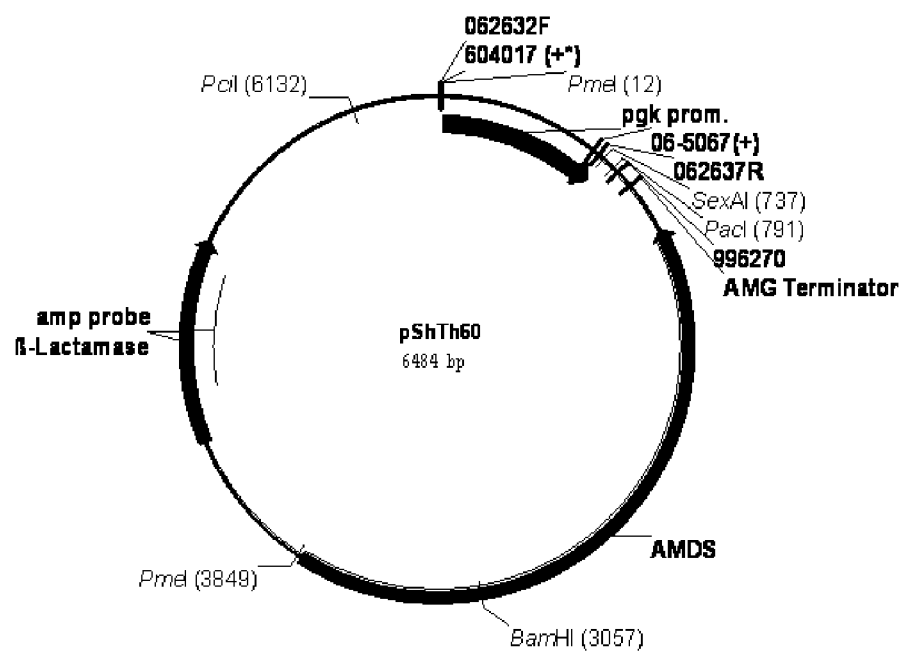
FIG. 1 shows a restriction map of pShTh60.

C4 dicarboxylic acid transporter: The term "C4 dicarboxylic acid transporter" is defined herein as a dicarboxylic acid permease that can transport malic acid, succinic acid, oxaloacetic acid, malonic acid, and/or fumaric acid outside a cell (Grobler et al., 1995, *Yeast* 11: 1485-1491; Camarasa et al., 2001, *Applied and Environmental Microbiology* 67: 4144-4151). A computational method to predict mitochondrially imported proteins and their targeting sequences is described by Claros and Vincens, 1996, *Eur. J. Biochem.* 241: 779-786.

The C4 dicarboxylic acid transporters have at least 20%, e.g., at least 40%, at least 50%, at least 60%, at least 70%, at least 80%, at least 90%, at least 95%, at least 96%, at least 97%, at least 98%, at least 99%, or 100% of the malic acid transporter activity of SEQ ID NO: 8, SEQ ID NO: 34, and/or SEQ ID NO: 36.

Malate dehydrogenase: The term "malate dehydrogenase" is defined herein as a malate:NAD$^+$ oxidoreductase (EC 1.1.1.37) that catalyzes the reduction of oxaloacetate in the presence of NADH+H$^+$ to malate and NAD$^+$. For purposes of the present invention, malate dehydrogenase activity is determined according to the following procedure. The assay solution consists of 1 mM oxaloacetic acid, 100 mM Tris pH 8.0, 10 mM NaHCO$_3$, 5 mM MgCl$_2$, and 0.1 mM NADH (Sigma Chemical Co., St. Louis, Mo., USA). The assay solution without oxaloacetic acid as substrate is run as a control to measure background NADH degradation rates. Dilutions of 1/100, 1/500, 1/2500, and 1/12500 of each supernatant are prepared with double-distilled water. Aliquots of 270 µl of the assay solution are dispensed into 96 well polystyrene flat bottom plates. A 30 µl sample of each diluted supernatant is added to initiate the assay. The reactions are monitored using a SPECTRAMAX® 340PC plate reader (Molecular Devices, Sunnyvale, Calif., USA) with the following settings: 340 nm, kinetic reading. A concentration series of NADH is used to construct a standard curve and a dilution series of purified malate dehydrogenase (Sigma Chemical Co., St. Louis, Mo., USA) is used as a positive control. One unit of malate dehydrogenase activity equals the amount of enzyme capable of converting 1 µmole of oxaloacetate and NADH+H$^+$ to malate and NAD$^+$ per minute at pH 8.0, 25° C.

The malate dehydrogenases have at least 20%, e.g., at least 40%, at least 50%, at least 60%, at least 70%, at least 80%, at least 90%, at least 95%, at least 96%, at least 97%, at least 98%, at least 99%, or 100% of the malate dehydrogenase activity of SEQ ID NO: 18 or SEQ ID NO: 20.

Pyruvate carboxylase: The term "pyruvate carboxylase" is defined herein as a pyruvate:carbon-dioxide ligase (ADP-forming) (EC 6.4.1.1) that catalyzes the carboxylation of pyruvate in the presence of ATP and HCO$_3^-$ to oxaloacetate, ADP, and phosphate. For purposes of the present invention, pyruvate carboxylase activity is determined according to the procedure of the SIGMA® Quality Control Test procedure for pyruvate carboxylase (Sigma Chemical Co., St. Louis, Mo., USA) except the assay uses Tris buffer at pH 8.0. One unit of pyruvate carboxylase activity equals the amount of enzyme capable of converting 1 µmole of pyruvate and $CO_2$ to oxaloacetate per minute at pH 7.8, 30° C.

The pyruvate carboxylases have at least 20%, e.g., at least 40%, at least 50%, at least 60%, at least 70%, at least 80%, at least 90%, at least 95%, at least 96%, at least 97%, at least 98%, at least 99%, or 100% of the pyruvate carboxylase activity of SEQ ID NO: 27.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide whose expression is quantitatively altered by the introduction of one or more (several) extra copies of the polynucleotide into the host cell.

Isolated polypeptide: The term "isolated polypeptide" as used herein refers to a polypeptide that is isolated from a source. In a preferred aspect, the polypeptide is at least 1% pure, e.g., at least 5% pure, at least 10% pure, at least 20% pure, at least 40% pure, at least 60% pure, at least 80% pure, at least 90% pure, at least 95% pure, at least 96% pure, at least 97% pure, at least 98% pure, at least 99% pure, at least 99.5% pure, or 100% pure as determined by SDS-PAGE.

Substantially pure polypeptide: The term "substantially pure polypeptide" denotes herein a polypeptide preparation that contains at most 10%, e.g., at most 8%, at most 6%, at most 5%, at most 4%, at most 3%, at most 2%, at most 1%, or at most 0.5% by weight of other polypeptide material with which it is natively or recombinantly associated. It is, therefore, preferred that the substantially pure polypeptide is at least 92% pure, e.g., at least 94% pure, at least 95% pure, at least 96% pure, at least 97% pure, at least 98% pure, at least 99% pure, at least 99.5% pure, or 100% pure by weight of the total polypeptide material present in the preparation. The polypeptides are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Aspergillus oryzae* C4 dicarboxylic acid transporter of SEQ ID NO: 8, SEQ ID NO: 34, or SEQ ID NO: 36, the *Aspergillus oryzae* malate dehydrogenase of SEQ ID NO. 18 or SEQ ID NO: 20, or the *Aspergillus oryzae* pyruvate carboxylase of SEQ ID NO. 27.

Polypeptide fragment: The term "polypeptide fragment" is defined herein as a polypeptide having one or more (several) amino acids deleted from the amino and/or carboxyl terminus of SEQ ID NO: 8, SEQ ID NO: 18, SEQ ID NO: 20, SEQ ID NO: 27, SEQ ID NO: 34, or SEQ ID NO: 36; or a homologous sequence thereof; wherein the fragment has C4 dicarboxylic acid transporter activity (for a fragment of SEQ ID NO: 8, SEQ ID NO: 34, or SEQ ID NO: 36), malate dehydrogenase activity (for a fragment of SEQ ID NO: 18 or SEQ ID NO: 20), or pyruvate carboxylase activity (for a fragment of SEQ ID NO: 27).

Subsequence: The term "subsequence" is defined herein as a nucleotide sequence having one or more (several) nucleotides deleted from the 5' and/or 3' end of SEQ ID NO: 7, SEQ ID NO: 17, SEQ ID NO: 19, SEQ ID NO: 26, SEQ ID NO: 33, SEQ ID NO: 35, or SEQ ID NO: 37; or a homologous sequence thereof; wherein the subsequence encodes a polypeptide fragment having C4 dicarboxylic acid transporter activity (for a subsequence of SEQ ID NO: 7, SEQ ID NO: 33, SEQ ID NO: 35, or SEQ ID NO: 37), malate dehydrogenase activity (for a subsequence of SEQ ID NO: 17 or SEQ ID NO: 19), or pyruvate carboxylase activity (for a subsequence of SEQ ID NO: 26).

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In one aspect, the polynucleotide is at least 1% pure, e.g., at least 5% pure, at least 10% pure, at least 20% pure, at least 40% pure, at least 60% pure, at least 80% pure, at least 90% pure, at least 95% pure, at least 96% pure, at least 97% pure, at least 98% pure, at least 99% pure, at least 99.5% pure, or 100% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, e.g., at most 8%, at most 6%, at most 5%, at most 4%, at most 3%, at most 2%, at most 1%, or at most 0.5% by weight of other polynucleotide material with which it is natively or recombinantly associated. A substantially pure polynucleotide may, however, include naturally occurring 5' and 3' untranslated regions, such as promoters and terminators. In one aspect, the substantially pure polynucleotide is at least 90% pure, e.g., at least 92% pure, at least 94% pure, at least 95% pure, at least 96% pure, at least 97% pure, at least 98% pure, at least 99% pure, at least 99.5%, or 100% pure by weight of the total polynucleotide material present in the preparation. The polynucleotides are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences. In some instances, a cDNA sequence may be identical to a genomic DNA sequence.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

Control sequences: The term "control sequences" is defined herein to include all components necessary for the expression of a polynucleotide encoding a polypeptide. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide encoding a malate dehydrogenase, a polynucleotide encoding a pyruvate carboxylase, and/or a polynucleotide encoding a C4 dicarboxylic acid transporter.

Artificial variant: When used herein, the term "artificial variant" means a polypeptide having malate dehydrogenase activity produced by an organism expressing a modified polynucleotide sequence (e.g., a modified polynucleotide sequence comprising or consisting of SEQ ID NO: 17); or a homologous sequence thereof. The modified nucleotide sequence is obtained through human intervention by modification of the polynucleotide sequence comprising or consisting of SEQ ID NO: 17; or a homologous sequence thereof.

Variant: The term "variant" means a polypeptide having activity, e.g., C4 dicarboxylic acid transporter activity, comprising an alteration/modification, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more (several), e.g., 1-3 amino acids, adjacent to an amino acid occupying a position.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

The present invention describes the overexpression of specific genes in a filamentous fungus, e.g., *Aspergillus*, to enhance C4 dicarboxylic acid production, such as malic acid production, that encompasses carboxylation of pyruvate to oxaloacetate by a pyruvate carboxylase, reduction of oxaloacetate to malate by a malate dehydrogenase, and/or transport of the C4 dicarboxylic acid out of the cell via a C4 dicarboxylic acid transporter.

The present invention relates to methods of producing C4 dicarboxylic acid (e.g., malic acid), comprising: (a) cultivating in a medium a filamentous fungal host cell comprising one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase;

wherein the filamentous fungal host cell secretes (or is capable of secreting) increased levels of the C4 dicarboxylic acid compared to the filamentous fungal host cell without the one or more (several) heterologous polynucleotides encoding the C4 dicarboxylic acid transporter, the malate dehydrogenase, and the pyruvate carboxylase when cultivated under the same conditions; and (b) recovering the C4 dicarboxylic acid.

The present invention also relates to methods for increasing C4 dicarboxylic acid production (e.g., malic acid production) relative to a parent host cell, comprising: (a) transforming into a filamentous fungal host cell one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase, wherein the filamentous fungal host cell secretes (or is capable of secreting) increased levels of malic acid compared to the filamentous fungal host cell without the one or more (several) heterologous polynucleotides encoding the C4 dicarboxylic acid transporter, the malate dehydrogenase, and the pyruvate carboxylase when cultivated under the same conditions; (b) cultivating the transformed filamentous fungal host cell in a medium; and (c) recovering the C4 dicarboxylic acid.

The present invention also relates to filamentous fungal host cells, comprising one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase, wherein the filamentous fungal host cell secretes (or is capable of secreting) increased levels of the C4 dicarboxylic acid (e.g., malic acid) compared to the filamentous fungal host cell without the one or more (several) heterologous polynucleotides encoding the C4 dicarboxylic acid transporter, the malate dehydrogenase, and the pyruvate carboxylase when cultivated under the same conditions.

In any of these aspects, the C4 dicarboxylic acid is malic acid, succinic acid, oxaloacetic acid, malonic acid, or fumaric acid, or combinations thereof. In some aspects, the C4 dicarboxylic acid is malic acid, succinic acid, or fumaric acid, or combinations thereof. In some aspects, the C4 dicarboxylic acid is malic acid or fumaric acid, or a combination of malic acid and fumaric acid. In some aspects, the C4 dicarboxylic acid is malic acid.

In one aspect, the filamentous fungal host cell comprises a heterologous polynucleotide encoding a C4 dicarboxylic acid transporter. In another aspect, the filamentous fungal host cell comprises a heterologous polynucleotide encoding a malate dehydrogenase. In another aspect, the filamentous fungal host cell comprises a heterologous polynucleotide encoding a pyruvate carboxylase. In another aspect, the filamentous fungal host cell comprises a heterologous polynucleotide encoding a C4 dicarboxylic acid transporter and a heterologous polynucleotide encoding a malate dehydrogenase. In another aspect, the filamentous fungal host cell comprises a heterologous polynucleotide encoding a C4 dicarboxylic acid transporter and a heterologous polynucleotide encoding a pyruvate carboxylase. In another aspect, the filamentous fungal host cell comprises a heterologous polynucleotide encoding a malate dehydrogenase and a heterologous polynucleotide encoding a pyruvate carboxylase. In another aspect, the filamentous fungal host cell comprises a heterologous polynucleotide encoding a C4 dicarboxylic acid transporter, a heterologous polynucleotide encoding a malate dehydrogenase, and a heterologous polynucleotide encoding a pyruvate carboxylase.

In the methods of the present invention, the recombinant filamentous fungal host cell is cultivated in a nutrient medium suitable for production of the C4 dicarboxylic acid transporter, the malate dehydrogenase, and/or the pyruvate carboxylase using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide(s) to be expressed and/or isolated. The cultivation takes place in a suitable nutrient medium comprising carbon and nitrogen sources and inorganic salts, using procedures known in the art. Suitable media are available from commercial suppliers, may be prepared according to published compositions (e.g., in catalogues of the American Type Culture Collection), or may be prepared from commercially available ingredients.

The C4 dicarboxylic acid transporter, malate dehydrogenase, and pyruvate carboxylase can be detected using methods known in the art that are specific for the polypeptides. These detection methods may include use of specific antibodies, formation of an enzyme product, or disappearance of an enzyme substrate. For example, an enzyme assay may be used to determine the activity of the malate dehydrogenase and the pyruvate carboxylase, as described herein.

C4 dicarboxylic acids such as malic acid can be recovered using any method known in the art. See, for example, WO 1998/022611 and U.S. Pat. No. 7,601,865.

In a one aspect, the level of secreted C4 dicarboxylic acid produced by a filamentous fungal host cell comprising a heterologous first polynucleotide encoding a C4 dicarboxylic acid transporter, a heterologous second polynucleotide encoding a malate dehydrogenase, and/or a heterologous third polynucleotide encoding a pyruvate carboxylase is increased at least 25%, e.g., at least 50%, at least 100%, at least 200%, or at 500% compared to the filamentous fungal host cell without the heterologous first polynucleotide, heterologous second polynucleotide, and/or heterologous third polynucleotide when cultivated under the same conditions.

In one aspect, a cultivated preparation of the filamentous fungal host cell produces (or is capable of producing) C4 dicarboxylic acid (e.g., malic acid) at a level greater than about any of 30 g/L, 60 g/L, 90 g/L, 120 g/L, 150 g/L, 175 g/L, 200 g/L, 225 g/L, or 250 g/L. In another aspect, a cultivated preparation of the filamentous fungal host cell produces (or is capable of producing) C4 dicarboxylic acid (e.g., malic acid) at a level greater than about any of 30 g/L, 60 g/L, 90 g/L, 120 g/L, 150 g/L, 175 g/L, 200 g/L, 225 g/L, or 250 g/L within 24, 48, 72, 96, 120, 144, 165, or 192 hours. For example, in one aspect, the preparation produces (or is capable of producing) C4 dicarboxylic acid (e.g., malic acid) at a level greater than about any of 30 g/L, 60 g/L, 90 g/L, 120 g/L, 150 g/L, 175 g/L, 200 g/L, 225 g/L, or 250 g/L within 48 hours. In another aspect, the preparation produces (or is capable of producing) C4 dicarboxylic acid (e.g., malic acid) at a level greater than about any of 30 g/L, 60 g/L, 90 g/L, 120 g/L, 150 g/L, 175 g/L, 200 g/L, 225 g/L, or 250 g/L within 144 hours. In any of these aspects or aspects of the methods herein, a cultivated preparation of the filamentous fungal host cell produces (or is capable of producing) the C4 dicarboxylic acid (e.g., malic acid) at a pH of less than or equal to about 7.0, such as 6.0 to 7.0, 6.0 to 6.5, 6.5 to 7.0, about 6.5, or less than about 6.5.

C4 Dicarboxylic Acid Transporters and Polynucleotides Encoding the C4 Dicarboxylic Acid Transporters In the present invention, the C4 dicarboxylic acid transporter can be any C4 dicarboxylic acid transporter that is suitable for practicing the present invention. In one aspect, the C4 dicarboxylic acid transporter is a transporter that is overexpressed under culture conditions that produces malic acid in high titers.

In one aspect, the C4 dicarboxylic acid transporter is (a) a C4 dicarboxylic acid transporter comprising an amino acid sequence having at least 60% sequence identity with SEQ ID NO: 8, SEQ ID NO: 34, and/or SEQ ID NO: 36; (b) a C4 dicarboxylic acid transporter encoded by a polynucleotide that hybridizes under low stringency conditions with SEQ ID NO: 7, SEQ ID NO: 33, SEQ ID NO: 35 and/or SEQ ID NO: 37; or a full-length complementary strand thereof; (c) a C4 dicarboxylic acid transporter encoded by a polynucleotide comprising a nucleotide sequence having at least 60% sequence identity with SEQ ID NO: 7, SEQ ID NO: 33, SEQ ID NO: 35 and/or SEQ ID NO: 37; (d) a C4 dicarboxylic acid transporter variant comprising a substitution, deletion, and/or insertion of one or more (several) amino acids of the mature polypeptide of SEQ ID NO: 8, SEQ ID NO: 34, and/or SEQ ID NO: 36; or (e) a fragment of the C4 dicarboxylic acid transporter of (a), (b), (c), or (d) that has C4 dicarboxylic acid transporter activity.

In a first aspect, the C4 dicarboxylic acid transporter is (a) a C4 dicarboxylic acid transporter comprising an amino acid sequence having at least 60% sequence identity with SEQ ID NO: 8; (b) a C4 dicarboxylic acid transporter encoded by a polynucleotide that hybridizes under low stringency conditions with SEQ ID NO: 7 or the full-length complementary strand thereof; (c) a C4 dicarboxylic acid transporter encoded by a polynucleotide comprising a nucleotide sequence having at least 60% sequence identity with SEQ ID NO: 7; (d) a C4 dicarboxylic acid transporter variant comprising a substitution, deletion, and/or insertion of one or more (several) amino acids of the mature polypeptide of SEQ ID NO: 8; or (e) a fragment of the C4 dicarboxylic acid transporter of (a), (b), (c), or (d) that has C4 dicarboxylic acid transporter activity.

In one aspect, the C4 dicarboxylic acid transporter comprises an amino acid sequence having a degree of sequence identity to SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which have C4 dicarboxylic acid transporter activity (hereinafter "homologous C4 dicarboxylic acid transporters"). In one aspect, the homologous C4 dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 8.

In one aspect, the C4 dicarboxylic acid transporter comprises the amino acid sequence of SEQ ID NO: 8 or an allelic variant thereof; or a fragment thereof having C4 dicarboxylic acid transporter activity. In another aspect, the C4 dicarboxylic acid transporter comprises the amino acid sequence of SEQ ID NO: 8. In another aspect, the C4 dicarboxylic acid transporter consists of the amino acid sequence of SEQ ID NO: 8 or an allelic variant thereof; or a fragment thereof having C4 dicarboxylic acid transporter activity. In another aspect, the C4 dicarboxylic acid transporter consists of the amino acid sequence of SEQ ID NO: 8.

In one aspect, the C4 dicarboxylic acid transporter is a variant comprising a substitution, deletion, and/or insertion of one or more (several) amino acids of the mature polypeptide of SEQ ID NO: 8. Preferably, amino acid changes are of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for C4 dicarboxylic acid transporter activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In some aspects, the total number of amino acid substitutions, deletions and/or insertions of the mature polypeptide of SEQ ID NO: 8 is not more than 10, e.g., not more than 1, 2, 3, 4, 5, 6, 7, 8 or 9. In another aspect, the total number of amino acid substitutions, deletions and/or insertions of the mature polypeptide of SEQ ID NO: 8 is 1, 2, 3, 4, 5, 6, 7, 8, 9, or 10.

In another aspect, the C4 dicarboxylic acid transporter is a fragment of SEQ ID NO: 8, wherein the fragment has C4 dicarboxylic acid transporter activity. A fragment of SEQ ID NO: 8 is a polypeptide having one or more (several) amino acids deleted from the amino and/or carboxyl terminus of this amino acid sequence. In one aspect, the fragment contains at least 320 amino acid residues, e.g., preferably at least 340 amino acid residues, or at least 360 amino acid residues of SEQ ID NO: 8.

The C4 dicarboxylic acid transporter may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In one aspect, the C4 dicarboxylic acid transporter is encoded by a polynucleotide that hybridizes under at least very low stringency conditions, e.g., low stringency conditions, medium stringency conditions, medium-high stringency conditions, high stringency conditions, or very high stringency conditions with SEQ ID NO: 7, a subsequence thereof, or a full-length complementary strand of the foregoing (J. Sambrook, E. F. Fritsch, and T. Maniatis, 1989, supra). The subsequence may encode a polypeptide fragment having C4 dicarboxylic acid transporter activity. A subsequence of SEQ ID NO: 7, or a homolog thereof, is a nucleotide sequence where one or more (several) nucleotides have been deleted from the 5'- and/or 3'-end. In one aspect, a subsequence contains at least 960 nucleotides, e.g., at least 1020 nucleotides or at least 1080 nucleotides SEQ ID NO: 7.

In one aspect, the C4 dicarboxylic acid transporter is encoded by a polynucleotide comprising or consisting of a nucleotide sequence having a degree of sequence identity to SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which encode polypeptides having C4 dicarboxylic acid transporter activity.

In a second aspect, the C4 dicarboxylic acid transporter is (a) a C4 dicarboxylic acid transporter comprising an amino acid sequence having at least 60% sequence identity with SEQ ID NO: 34; (b) a C4 dicarboxylic acid transporter encoded by a polynucleotide that hybridizes under low stringency conditions with SEQ ID NO: 33 or the full-length complementary strand thereof; (c) a C4 dicarboxylic acid transporter encoded by a polynucleotide comprising a nucleotide sequence having at least 60% sequence identity with SEQ ID NO: 33; (d) a C4 dicarboxylic acid transporter variant comprising a substitution, deletion, and/or insertion of one or more (several) amino acids of the mature polypeptide of SEQ ID NO: 34; or (e) a fragment of the C4 dicarboxylic acid transporter of (a), (b), (c), or (d) that has C4 dicarboxylic acid transporter activity.

In one aspect, the C4 dicarboxylic acid transporter comprises an amino acid sequence having a degree of sequence identity to SEQ ID NO: 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which have C4 dicarboxylic acid transporter activity (hereinafter "homologous C4 dicarboxylic acid transporters"). In one aspect, the homologous C4 dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 34.

In one aspect, the C4 dicarboxylic acid transporter comprises the amino acid sequence of SEQ ID NO: 34 or an allelic variant thereof; or a fragment thereof having C4 dicarboxylic acid transporter activity. In another aspect, the C4 dicarboxylic acid transporter comprises the amino acid sequence of SEQ ID NO: 34. In another aspect, the C4 dicarboxylic acid transporter consists of the amino acid sequence of SEQ ID NO: 34 or an allelic variant thereof; or a fragment thereof having C4 dicarboxylic acid transporter activity. In another aspect, the C4 dicarboxylic acid transporter consists of the amino acid sequence of SEQ ID NO: 34.

In one aspect, the C4 dicarboxylic acid transporter is a variant comprising a substitution, deletion, and/or insertion of one or more (several) amino acids of the mature polypeptide of SEQ ID NO: 34, as described supra. In some aspects, the total number of amino acid substitutions, deletions and/or insertions of the mature polypeptide of SEQ ID NO: 34 is not more than 10, e.g., not more than 1, 2, 3, 4, 5, 6, 7, 8 or 9. In another aspect, the total number of amino acid substitutions, deletions and/or insertions of the mature polypeptide of SEQ ID NO: 34 is 1, 2, 3, 4, 5, 6, 7, 8, 9, or 10.

In another aspect, the C4 dicarboxylic acid transporter is a fragment of SEQ ID NO: 34, wherein the fragment has C4 dicarboxylic acid transporter activity. In one aspect, a fragment contains at least 334 amino acid residues, e.g., at least 354 amino acid residues or at least 374 amino acid residues of SEQ ID NO: 34.

In one aspect, the C4 dicarboxylic acid transporter is encoded by a polynucleotide that hybridizes under at least very low stringency conditions, low stringency conditions, medium stringency conditions, medium-high stringency conditions, high stringency conditions, or very high stringency conditions with SEQ ID NO: 33, a subsequence of thereof, or a full-length complementary strand of the foregoing, (J. Sambrook, E. F. Fritsch, and T. Maniatis, 1989, supra). The subsequence may encode a polypeptide fragment having C4 dicarboxylic acid transporter activity. A subsequence of SEQ ID NO: 33, or a homolog thereof, is a nucleotide sequence where one or more (several) nucleotides have been deleted from the 5'- and/or 3'-end. In one aspect, a subsequence contains at least 1002 nucleotides, e.g., at least 1062 nucleotides or at least 1122 nucleotides SEQ ID NO: 33.

In one aspect, the C4 dicarboxylic acid transporter is encoded by a polynucleotide comprising or consisting of a nucleotide sequence having a degree of sequence identity to SEQ ID NO: 33 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which encode polypeptides having C4 dicarboxylic acid transporter activity.

In a third aspect, the C4 dicarboxylic acid transporter is (a) a C4 dicarboxylic acid transporter comprising an amino acid sequence having at least 60% sequence identity with SEQ ID NO: 36; (b) a C4 dicarboxylic acid transporter encoded by a polynucleotide that hybridizes under low stringency conditions with SEQ ID NO: 35 or SEQ ID NO: 37, or a full-length complementary strand thereof; or (c) a C4 dicarboxylic acid transporter encoded by a polynucleotide comprising a nucleotide sequence having at least 60% sequence identity with SEQ ID NO: 35 or SEQ ID NO: 37; (d) a C4 dicarboxylic acid transporter variant comprising a substitution, deletion, and/or insertion of one or more (several) amino acids of the mature polypeptide of SEQ ID NO: 36; or (e) a fragment of the C4 dicarboxylic acid transporter of (a), (b), (c), or (d) that has C4 dicarboxylic acid transporter activity.

In one aspect, the C4 dicarboxylic acid transporter comprises an amino acid sequence having a degree of sequence identity to SEQ ID NO: 36 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which have C4 dicarboxylic acid transporter activity (hereinafter "homologous C4 dicarboxylic acid transporters"). In one aspect, the homologous C4 dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 36.

In one aspect, the C4 dicarboxylic acid transporter comprises the amino acid sequence of SEQ ID NO: 36 or an allelic variant thereof; or a fragment thereof having C4 dicarboxylic acid transporter activity. In another aspect, the C4 dicarboxylic acid transporter comprises the amino acid sequence of SEQ ID NO: 36. In another aspect, the C4 dicarboxylic acid transporter consists of the amino acid sequence of SEQ ID NO: 36 or an allelic variant thereof; or a fragment thereof having C4 dicarboxylic acid transporter activity. In another aspect, the C4 dicarboxylic acid transporter consists of the amino acid sequence of SEQ ID NO: 36.

In one aspect, the C4 dicarboxylic acid transporter is a variant comprising a substitution, deletion, and/or insertion of one or more (several) amino acids of the mature polypeptide of SEQ ID NO: 36, as described supra. In some aspects, the total number of amino acid substitutions, deletions and/or insertions of the mature polypeptide of SEQ ID NO: 36 is not more than 10, e.g., not more than 1, 2, 3, 4, 5, 6, 7, 8 or 9. In another aspect, the total number of amino acid substitutions, deletions and/or insertions of the mature polypeptide of SEQ ID NO: 36 is 1, 2, 3, 4, 5, 6, 7, 8, 9, or 10.

In another aspect, the C4 dicarboxylic acid transporter is a fragment of SEQ ID NO: 36, wherein the fragment has C4 dicarboxylic acid transporter activity. In one aspect, a fragment contains at least 375 amino acid residues, e.g., at least 395 amino acid residues or at least 415 amino acid residues of SEQ ID NO: 36.

In one aspect, the C4 dicarboxylic acid transporter is encoded by a polynucleotide that hybridizes under at least very low stringency conditions, e.g., low stringency conditions, medium stringency conditions, medium-high stringency conditions, high stringency conditions, or very high stringency conditions with SEQ ID NO: 35 or SEQ ID NO: 37, a subsequence thereof, or a full-length complementary strand of the foregoing (J. Sambrook, E. F. Fritsch, and T. Maniatis, 1989, supra). The subsequence may encode a polypeptide fragment having C4 dicarboxylic acid transporter activity. A subsequence of SEQ ID NO: 35, SEQ ID NO: 37, or a homolog thereof, is a nucleotide sequence where one or more (several) nucleotides have been deleted from the 5'- and/or 3'-end. In one aspect, a subsequence contains at least 1125 nucleotides, e.g., at least 1185 nucleotides or at least 1245 nucleotides of SEQ ID NO: 35 or SEQ ID NO: 37.

In one aspect, the C4 dicarboxylic acid transporter is encoded by a polynucleotide comprising or consisting of a nucleotide sequence having a degree of sequence identity to SEQ ID NO: 35 or SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which encode polypeptides having C4 dicarboxylic acid transporter activity.

The polynucleotide of SEQ ID NO: 7, SEQ ID NO: 33, SEQ ID NO: 35, or SEQ ID NO: 37; or a subsequence thereof; as well as the amino acid sequence of SEQ ID NO: 8, SEQ ID NO: 34, or SEQ ID NO: 36; or a fragment thereof; may be used to design nucleic acid probes to identify and clone DNA encoding C4 dicarboxylic acid transporters from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, at least 70 nucleotides in length. In one aspect, the nucleic acid probe is at least 100 nucleotides in length, e.g., at least 200 nucleotides, at least 300 nucleotides, at least 400 nucleotides, or at least 500 nucleotides in length. Even longer probes may be used, e.g., nucleic acid probes that are at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a C4 dicarboxylic acid transporter. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 7, SEQ ID NO: 33, SEQ ID NO: 35, or SEQ ID NO: 37; or a subsequence thereof; the carrier material is used in a Southern blot. For purposes of the present invention, hybridization indicates that the polynucleotide hybridizes to a labeled nucleotide probe corresponding to the polynucleotide shown in SEQ ID NO: 7, SEQ ID NO: 33, SEQ ID NO: 35, or SEQ ID NO: 37; a complementary strand thereof; or a subsequence of the foregoing, under low to very high stringency conditions. Molecules to which the probe hybridizes can be detected using, for example, X-ray film or any other detection means known in the art.

In one aspect, the nucleic acid probe is SEQ ID NO: 7, SEQ ID NO: 33, SEQ ID NO: 35, SEQ ID NO: 37, or a subsequence thereof. In another aspect, the nucleic acid probe is a polynucleotide sequence that encodes SEQ ID NO: 8, SEQ ID NO: 34, or SEQ ID NO: 36; or a subsequence thereof. In one aspect, the nucleic acid probe is SEQ ID NO: 7. In another aspect, the nucleic acid probe is a polynucleotide sequence that encodes SEQ ID NO: 8, or a subsequence thereof. In another aspect, the nucleic acid probe is SEQ ID NO: 33. In another aspect, the nucleic acid probe is a polynucleotide sequence that encodes SEQ ID NO: 34, or a subsequence thereof. In one aspect, the nucleic acid probe is SEQ ID NO: 35 or SEQ ID NO: 37. In one aspect, the nucleic acid probe is SEQ ID NO: 35. In another aspect, the nucleic acid probe is SEQ ID NO: 37. In another aspect, the nucleic acid probe is a polynucleotide sequence that encodes SEQ ID NO: 36, or a subsequence thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), or at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The C4 dicarboxylic acid transporter may be obtained from microorganisms of any genus. For purposes of the present invention, the term "obtained from" as used herein in connection with a given source shall mean that the C4 dicarboxylic acid transporter encoded by a polynucleotide is produced by the source or by a cell in which the polynucleotide from the source has been inserted. In one aspect, the C4 dicarboxylic acid transporter is transported to the outer membrane.

The C4 dicarboxylic acid transporter may be a bacterial C4 dicarboxylic acid transporter. For example, the C4 dicarboxylic acid transporter may be a Gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* C4 dicarboxylic acid transporter, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* C4 dicarboxylic acid transporter.

In one aspect, the C4 dicarboxylic acid transporter is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* C4 dicarboxylic acid transporter.

In another aspect, the C4 dicarboxylic acid transporter is a *Streptococcus equisimilis*, *Streptococcus pyogenes*, *Streptococcus uberis*, or *Streptococcus equi* subsp. *Zooepidemicus* C4 dicarboxylic acid transporter.

In another aspect, the C4 dicarboxylic acid transporter is a *Streptomyces achromogenes*, *Streptomyces avermitilis*, *Streptomyces coelicolor*, *Streptomyces griseus*, or *Streptomyces lividans* C4 dicarboxylic acid transporter.

The C4 dicarboxylic acid transporter may be a fungal C4 dicarboxylic acid transporter. In one aspect, the fungal C4 dicarboxylic acid transporter is a yeast C4 dicarboxylic acid transporter such as a *Candida*, *Kluyveromyces*, *Pichia*, *Saccharomyces*, *Schizosaccharomyces*, or *Yarrowia* C4 dicarboxylic acid transporter.

In one aspect, the C4 dicarboxylic acid transporter is a *Schizosaccharomyces* C4 dicarboxylic acid transporter, e.g., a *Schizosaccharomyces pombe* C4 dicarboxylic acid transporter, such as a *Schizosaccharomyces pombe* C4 dicarboxylic acid transporter of SEQ ID NO: 36.

In another aspect, the fungal C4 dicarboxylic acid transporter is a filamentous fungal C4 dicarboxylic acid transporter such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* C4 dicarboxylic acid transporter.

In another aspect, the C4 dicarboxylic acid transporter is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* C4 dicarboxylic acid transporter.

In another aspect, the C4 dicarboxylic acid transporter is an *Acremonium cellulolyticus*, *Aspergillus aculeatus*, *Aspergillus awamori*, *Aspergillus flavus*, *Aspergillus fumigatus*, *Aspergillus foetidus*, *Aspergillus japonicus*, *Aspergillus nidulans*, *Aspergillus niger*, *Aspergillus oryzae*, *Aspergillus sojae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium*

*venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* C4 dicarboxylic acid transporter.

In one aspect, the C4 dicarboxylic acid transporter is an *Aspergillus* C4 dicarboxylic acid transporter. In another aspect, the C4 dicarboxylic acid transporter is an *Aspergillus oryzae* C4 dicarboxylic acid transporter, such as an *Aspergillus oryzae* C4 dicarboxylic acid transporter of SEQ ID NO: 8. In another aspect, the C4 dicarboxylic acid transporter is an *Aspergillus terreus* C4 dicarboxylic acid transporter, such as an *Aspergillus terreus* C4 dicarboxylic acid transporter of SEQ ID NO: 34.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The C4 dicarboxylic acid transporter may also be identified and obtained from other sources including microorganisms isolated from nature (e.g., soil, composts, water, etc.) or DNA samples obtained directly from natural materials (e.g., soil, composts, water, etc) using the above-mentioned probes. Techniques for isolating microorganisms and DNA directly from natural habitats are well known in the art. The polynucleotide encoding a C4 dicarboxylic acid transporter may then be derived by similarly screening a genomic or cDNA library of another microorganism or mixed DNA sample. Once a polynucleotide encoding a C4 dicarboxylic acid transporter has been detected with suitable probe(s) as described herein, the sequence may be isolated or cloned by utilizing techniques that are known to those of ordinary skill in the art (see, e.g., J. Sambrook, E. F. Fritsch, and T. Maniatus, 1989, *Molecular Cloning, A Laboratory Manual,* 2d edition, Cold Spring Harbor, N.Y.).

The C4 dicarboxylic acid transporter can also include fused polypeptides or cleavable fusion polypeptides in which another polypeptide is fused at the N-terminus or the C-terminus of the polypeptide or fragment thereof. A fused polypeptide is produced by fusing a polynucleotide (or a portion thereof) encoding another polypeptide to a polynucleotide (or a portion thereof). Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Techniques used to isolate or clone a polynucleotide encoding a C4 dicarboxylic acid transporter are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shares structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus,* or another or related organism and thus, for example, may be an allelic or species variant of the polypeptide encoding region of the nucleotide sequence.

In one aspect, the isolated polynucleotide comprises or consists of SEQ ID NO: 7, SEQ ID NO: 33, SEQ ID NO: 35, or SEQ ID NO: 37. In another aspect, the isolated polynucleotide comprises or consists of SEQ ID NO: 7. In another aspect, the isolated polynucleotide comprises or consists of SEQ ID NO: 33. In another aspect, the isolated polynucleotide comprises or consists of SEQ ID NO: 35 or SEQ ID NO: 37. In another aspect, the isolated polynucleotide encodes a C4 dicarboxylic acid transporter comprising or consisting of SEQ ID NO: 8, SEQ ID NO: 34, or SEQ ID NO: 36. In another aspect, the isolated polynucleotide encodes a C4 dicarboxylic acid transporter comprising or consisting of SEQ ID NO: 8. In another aspect, the isolated polynucleotide encodes a C4 dicarboxylic acid transporter comprising or consisting of SEQ ID NO: 34. In another aspect, the isolated polynucleotide encodes a C4 dicarboxylic acid transporter comprising or consisting of SEQ ID NO: 36. Thus, the present invention encompasses nucleotide sequences that encode polypeptides comprising or consisting of the amino acid sequence of SEQ ID NO: 8, SEQ ID NO: 34, or SEQ ID NO: 36, but which differ from SEQ ID NO: 7, SEQ ID NO: 33, or SEQ ID NO: 35 or SEQ ID NO: 37, respectively, by virtue of the degeneracy of the genetic code.

The present invention also relates to subsequences of SEQ ID NO: 7, SEQ ID NO: 33, SEQ ID NO: 35, or SEQ ID NO: 37 that encode fragments of SEQ ID NO: 8, SEQ ID NO: 34, or SEQ ID NO: 36, respectively, that have C4 dicarboxylic acid transporter activity. In another aspect, the isolated polynucleotide can be a mutant polynucleotide comprising or consisting of at least one mutation in SEQ ID NO: 7, SEQ ID NO: 33, SEQ ID NO: 35, or SEQ ID NO: 37 in which the mutant nucleotide sequence encodes SEQ ID NO: 8, SEQ ID NO: 34, or SEQ ID NO: 36, respectively. In another aspect, the isolated polynucleotide can be a mutant polynucleotide comprising or consisting of at least one mutation in SEQ ID NO: 7, in which the mutant nucleotide sequence encodes SEQ ID NO: 8.

In another aspect, the isolated polynucleotide can be a mutant polynucleotide comprising or consisting of at least one mutation in SEQ ID NO: 33, in which the mutant nucleotide sequence encodes SEQ ID NO: 34. In another aspect, the isolated polynucleotide can be a mutant polynucleotide comprising or consisting of at least one mutation in SEQ ID NO: 35 or SEQ ID NO: 37, in which the mutant nucleotide sequence encodes SEQ ID NO: 36.

In another aspect, the isolated polynucleotide comprises or consists of a nucleotide sequence having a degree of sequence identity to SEQ ID NO: 7, SEQ ID NO: 33, SEQ ID NO: 35, or SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity, which encode active C4 dicarboxylic acid transporters.

For example, in one aspect, the isolated polynucleotide comprises or consists of a nucleotide sequence having a degree of sequence identity to SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity, which encode active C4 dicarboxylic acid transporters. In another aspect, the isolated polynucleotide comprises or consists of a nucleotide sequence having a degree of sequence identity to SEQ ID NO: 33 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity, which encode active C4 dicarboxylic acid transporters. In another aspect, the isolated polynucleotide comprises or consists of a nucleotide sequence having a degree of sequence identity to SEQ ID NO: 35 or SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity, which encode active C4 dicarboxylic acid transporters.

In another aspect, the isolated polynucleotide encoding a C4 dicarboxylic acid transporter hybridizes under at least very low stringency conditions, e.g., low stringency conditions, medium stringency conditions, medium-high stringency conditions, high stringency conditions, or very high stringency conditions with (i) SEQ ID NO: 7, SEQ ID NO: 33, SEQ ID NO: 35, or SEQ ID NO: 37, an allelic variant or subsequence thereof, or a full-length complementary strand of the foregoing (Sambrook et al., 1989, supra), as defined herein.

For example, in one aspect, the isolated polynucleotide encoding a C4 dicarboxylic acid transporter hybridizes under at least very low stringency conditions, e.g., low stringency conditions, medium stringency conditions, medium-high stringency conditions, high stringency conditions, or very high stringency conditions with SEQ ID NO: 7, an allelic variant or subsequence thereof, or a full-length complementary strand of the foregoing, (Sambrook et al., 1989, supra), as defined herein. In another aspect, the isolated polynucleotide encoding a C4 dicarboxylic acid transporter hybridizes under at least very low stringency conditions, low stringency conditions, medium stringency conditions, medium-high stringency conditions, high stringency conditions, or very high stringency conditions with SEQ ID NO: 33, an allelic variant or subsequence thereof, or a full-length complementary strand of the foregoing (Sambrook et al., 1989, supra), as defined herein. In another aspect, the isolated polynucleotide encoding a C4 dicarboxylic acid transporter hybridizes under at least very low stringency conditions, e.g., low stringency conditions, medium stringency conditions, medium-high stringency conditions, high stringency conditions, or very high stringency conditions with SEQ ID NO: 35 or SEQ ID NO: 37, an allelic variant or subsequence thereof, or a full-length complementary strand of the foregoing (Sambrook et al., 1989, supra), as defined herein.

In one aspect, the isolated polynucleotide encoding a C4 dicarboxylic acid transporter is obtained by (a) hybridizing a population of DNA under very low, low, medium, medium-high, high, or very high stringency conditions with SEQ ID NO: 7, SEQ ID NO: 33, SEQ ID NO: 35 or SEQ ID NO: 37, or a full-length complementary strand thereof; and (b) isolating the hybridizing polynucleotide, which encodes a polypeptide having C4 dicarboxylic acid transporter activity.

For example, in one aspect, the isolated polynucleotide encoding a C4 dicarboxylic acid transporter is obtained by (a) hybridizing a population of DNA under very low, low, medium, medium-high, high, or very high stringency conditions with SEQ ID NO: 7, or the full-length complementary strand thereof; and (b) isolating the hybridizing polynucleotide, which encodes a polypeptide having C4 dicarboxylic acid transporter activity. In another aspect, the isolated polynucleotide encoding a C4 dicarboxylic acid transporter is obtained by (a) hybridizing a population of DNA under very low, low, medium, medium-high, high, or very high stringency conditions with SEQ ID NO: 33 or the full-length complementary strand thereof; and (b) isolating the hybridizing polynucleotide, which encodes a polypeptide having C4 dicarboxylic acid transporter activity. In another aspect, the isolated polynucleotide encoding a C4 dicarboxylic acid transporter is obtained by (a) hybridizing a population of DNA under very low, low, medium, medium-high, high, or very high stringency conditions with SEQ ID NO: 35 or SEQ ID NO: 37, or a full-length complementary strand thereof; and (b) isolating the hybridizing polynucleotide, which encodes a polypeptide having C4 dicarboxylic acid transporter activity.

Other C4 dicarboxylic acid transporters that can be used to practice the present invention include, e.g., the *Aspergillus flavus* C4 dicarboxylic acid transporter (AFLA__107340).

Malate Dehydrogenases and Polynucleotides Encoding the Malate Dehydrogenases

In the present invention, the malate dehydrogenase can be any malate dehydrogenase that is suitable for practicing the present invention. In one aspect, the malate dehydrogenase is an enzyme that is present in the cytosol of the host cell.

Malate dehydrogenases that can be used to practice the present invention include, but are not limited to, an *Aspergillus fumigatus* malate dehydrogenase (AFUA__2G13800; Nierman et al., 2005, *Nature* 438: 1151-1156); *Aspergillus nidulans* malate dehydrogenase (AN5031.1, AN6499.1; Sims et al., 2004, *Mycol. Res.* 108: 853-857); *Aspergillus niger* malate dehydrogenase (An11g07190, An12g00160, An15g00070; Pel et al., 2007, *Nature Biotechnology* 25: 221-231); *Aspergillus oryzae* NRRL 3488 malate dehydrogenase (genomic DNA sequence of SEQ ID NO: 19 and the deduced amino acid sequence of SEQ ID NO: 20); *Phytophthora infestans* malate dehydrogenase (PITG 15476.1; Calcagno et al., 2009, *Mycological Research* 113: 771-781); and *Saccharomyces cerevisiae* malate dehydrogenase (YOL126C; Minard and McAlister-Henn, 1991, *Mol. Cell. Biol.* 11: 370-380; YDL078C; McAlister-Henn et al., 1995, *Journal of Biological Chemistry* 270: 21220-21225).

In one aspect, the malate dehydrogenase is (a) a malate dehydrogenase comprising an amino acid sequence having at least 60% sequence identity with SEQ ID NO: 18 or SEQ ID NO: 20; (b) a malate dehydrogenase encoded by a polynucleotide that hybridizes under at least low stringency conditions with (i) SEQ ID NO: 17 or SEQ ID NO: 19, (ii) the cDNA sequence contained in SEQ ID NO: 17 or SEQ ID NO: 19, or (iii) a full-length complementary strand of (i) or (ii); (c) a malate dehydrogenase encoded by a polynucleotide comprising a nucleotide sequence having at least 60% sequence identity with SEQ ID NO: 17 or SEQ ID NO: 19; (d) a malate dehydrogenase variant comprising a substitution, deletion, and/or insertion of one or more (several) amino acids of the mature polypeptide of SEQ ID NO: 18 or SEQ ID NO: 20; or (e) a fragment of the malate dehydrogenase of (a), (b), (c), or (d) that has malate dehydrogenase activity.

In a one aspect, the malate dehydrogenase comprises or consists of an amino acid sequence having a degree of sequence identity to SEQ ID NO: 18 or SEQ ID NO: 20 of at least 60%, e.g., at least 65%, at least 70%, at least 75%, at least 80%, at least 85%, at least 90%, at least 91%, at least 92%, at least 93%, at least 95%, at least 96%, at least 97%, at least 98%, or at least 99%, which has malate dehydrogenase activity (hereinafter "homologous malate dehydrogenases"). In one aspect, the homologous malate dehydrogenase comprises an amino acid sequence that differs by no more than ten amino acids, e.g., by no more than five amino acids, by no more than four amino acids, by no more than three amino acids, by no more than two amino acids, or by one amino acid from SEQ ID NO: 18 or SEQ ID NO: 20.

In one aspect, the malate dehydrogenase comprises or consists of an amino acid sequence having a degree of sequence identity to SEQ ID NO: 18 of at least 60%, e.g., at least 65%, at least 70%, at least 75%, at least 80%, at least 85%, at least 90%, at least 91%, at least 92%, at least 93%, at least 95%, at least 96%, at least 97%, at least 98%, or at least 99%. In one aspect, the homologous malate dehydrogenase comprises an amino acid sequence that differs by no more than ten amino acids, e.g., by no more than five amino acids, by no more than four amino acids, by no more than three amino acids, by no more than two amino acids, or by one amino acid from SEQ ID NO: 18.

In another aspect, the malate dehydrogenase comprises or consists of an amino acid sequence having a degree of sequence identity to SEQ ID NO: 20 of at least 60%, e.g., at least 65%, at least 70%, at least 75%, at least 80%, at least 85%, at least 90%, at least 91%, at least 92%, at least 93%, at least 95%, at least 96%, at least 97%, at least 98%, or at least 99%, which has malate dehydrogenase activity. In one aspect, the homologous malate dehydrogenase comprises an amino acid sequence that differs by no more than ten amino acids, e.g., by no more than five amino acids, by no more than four amino acids, by no more than three amino acids, by no more than two amino acids, by one amino acid from SEQ ID NO: 20.

A substantially homologous malate dehydrogenase may have one or more (several) amino acid substitutions, deletions and/or insertions, as described supra.

In one aspect, the malate dehydrogenase comprises the amino acid sequence of SEQ ID NO: 18 or SEQ ID NO: 20 or an allelic variant thereof; or a fragment thereof having malate dehydrogenase activity. In another aspect, the malate dehydrogenase comprises the amino acid sequence of SEQ ID NO: 18 or SEQ ID NO: 20. In another aspect, the malate dehydrogenase comprises the amino acid sequence of SEQ ID NO: 18. In another aspect, the malate dehydrogenase comprises the amino acid sequence of SEQ ID NO: 20. In another aspect, the malate dehydrogenase consists of the amino acid sequence of SEQ ID NO: 18 or SEQ ID NO: 20 or an allelic variant thereof; or a fragment thereof having malate dehydrogenase activity. In another aspect, the malate dehydrogenase consists of the amino acid sequence of SEQ ID NO: 18 or SEQ ID NO: 20. In another aspect, the malate dehydrogenase consists of the amino acid sequence of SEQ ID NO: 18. In another aspect, the malate dehydrogenase consists of the amino acid sequence of SEQ ID NO: 20.

In another aspect, the malate dehydrogenase is a variant comprising a substitution, deletion, and/or insertion of one or more (several) amino acids of the mature polypeptide of SEQ ID NO: 18 or SEQ ID NO: 20, as described supra. In some aspects, the total number of amino acid substitutions, deletions and/or insertions of the mature polypeptide of SEQ ID NO: 18 or SEQ ID NO: 20 is not more than 10, e.g., not more than 1, 2, 3, 4, 5, 6, 7, 8 or 9. In another aspect, the total number of amino acid substitutions, deletions and/or insertions of the mature polypeptide of SEQ ID NO: 18 or SEQ ID NO: 20 is 1, 2, 3, 4, 5, 6, 7, 8, 9, or 10.

In another aspect, the malate dehydrogenase is a fragment of SEQ ID NO: 18 or SEQ ID NO: 20, wherein the fragment has malate dehydrogenase activity. In one aspect, a fragment of SEQ ID NO: 18 contains at least 290 amino acid residues, e.g., at least 305 amino acid residues or at least 320 amino acid residues. In one aspect, a fragment of SEQ ID NO: 20 contains at least 280 amino acid residues, e.g., at least 295 amino acid residues or at least 310 amino acid residues.

In a another aspect, the malate dehydrogenase is encoded by a polynucleotide that hybridizes under at least very low stringency conditions, e.g., low stringency conditions, medium stringency conditions, medium-high stringency conditions, high stringency conditions, or very high stringency conditions with (i) SEQ ID NO: 17 or SEQ ID NO: 19, (ii) the cDNA sequence contained in SEQ ID NO: 17 or SEQ ID NO: 19, (iii) a subsequence of (i) or (ii), or (iv) a full-length complementary strand of (i), (ii), or (iii) (J. Sambrook, E. F. Fritsch, and T. Maniatis, 1989, supra). The subsequence may encode a polypeptide fragment having malate dehydrogenase activity.

A subsequence of SEQ ID NO: 17 or SEQ ID NO: 19, or a homolog thereof, is a nucleotide sequence where one or more (several) nucleotides have been deleted from the 5'- and/or 3'-end. In one aspect, a subsequence of SEQ ID NO: 17 contains at least 870 nucleotides, e.g., at least 915 nucleotides or at least 960 nucleotides. In another aspect, a subsequence of SEQ ID NO: 19 contains at least 840 nucleotides, e.g., at least 885 nucleotides or at least 930 nucleotides.

The polynucleotide of SEQ ID NO: 17 or SEQ ID NO: 19; or a subsequence thereof; as well as the amino acid sequence of SEQ ID NO: 18 or SEQ ID NO: 20; or a fragment thereof; may be used to design nucleic acid probes to identify and clone DNA encoding malate dehydrogenases from strains of different genera or species, as described supra. Such probes are encompassed by the present invention.

A genomic DNA or cDNA library prepared from such other organisms may be screened for DNA that hybridizes with the probes described above and encodes a malate dehydrogenase, as described supra.

In one aspect, the nucleic acid probe is SEQ ID NO: 17 or SEQ ID NO: 19. In another aspect, the nucleic acid probe is SEQ ID NO: 17. In another aspect, the nucleic acid probe is SEQ ID NO: 19. In another aspect, the nucleic acid probe is a polynucleotide sequence that encodes SEQ ID NO: 18 or SEQ ID NO: 20, or a subsequence thereof. In another aspect, the nucleic acid probe is a polynucleotide sequence that encodes SEQ ID NO: 18, or a subsequence thereof. In another aspect, the nucleic acid probe is a polynucleotide sequence that encodes SEQ ID NO: 20, or a subsequence thereof.

For long probes of at least 100 nucleotides in length, very low to very high stringency and washing conditions are defined as described supra.

For short probes of about 15 nucleotides to about 70 nucleotides in length, stringency and washing conditions are defined as described supra.

In another aspect, the malate dehydrogenase is encoded by a polynucleotide comprising or consisting of a nucleotide sequence having a degree of sequence identity to SEQ ID NO: 17 or SEQ ID NO: 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which encodes a polypeptide having malate dehydrogenase activity.

The malate dehydrogenase may be obtained from microorganisms of any genus. For purposes of the present invention, the term "obtained from" as used herein in connection with a given source shall mean that the malate dehydrogenase encoded by a polynucleotide is produced by the source or by a cell in which the polynucleotide from the source has been inserted.

In one aspect, the malate dehydrogenase may be a bacterial, yeast, or filamentous fungal malate dehydrogenase obtained from the microorganisms described herein.

In another aspect, the malate dehydrogenase is an *Aspergillus oryzae* malate dehydrogenase, e.g., the *Aspergillus oryzae* malate dehydrogenase of SEQ ID NO: 18 or SEQ ID NO: 20.

The malate dehydrogenase may also be identified and obtained from other sources including microorganisms isolated from nature (e.g., soil, composts, water, etc.) or DNA samples obtained directly from natural materials (e.g., soil, composts, water, etc) as described supra.

The malate dehydrogenase can also include fused polypeptides or cleavable fusion polypeptides, as described supra.

Techniques used to isolate or clone a polynucleotide encoding a malate dehydrogenase are described supra.

In another aspect, the malate dehydrogenase is a variant of a parent malate dehydrogenase that comprises one or more (several) modifications of the amino acid sequence, which reduces mitochondrial import in vivo of the malate dehydrogenase.

In another aspect, the malate dehydrogenase is a variant of a parent malate dehydrogenase comprising (i) a deletion at positions equivalent or corresponding to positions 2 to 17 or a portion thereof of SEQ ID NO: 18, and (ii) a substitution at a position equivalent to position 48 of SEQ ID NO: 18; wherein the deletion and the substitution reduce mitochondrial import in vivo of the malate dehydrogenase variant thereby increasing the level of the malate dehydrogenase variant in the cytosol. Such variants are described in detail below.

Conventions for Designation of Malate Dehydrogenase Variants

For purposes of the present invention, the amino acid sequence of the malate dehydrogenase disclosed in SEQ ID NO: 18 is used to determine the corresponding or equivalent amino acid residue in another malate dehydrogenase. The amino acid sequence of another malate dehydrogenase is aligned with the amino acid sequence of the malate dehydrogenase of SEQ ID NO: 18, and based on the alignment the amino acid position number corresponding to any amino acid residue in the amino acid sequence of the malate dehydrogenase of SEQ ID NO: 18 can be determined.

An alignment of polypeptide sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). An alignment of DNA sequences may be done using the polypeptide alignment as a template, replacing the amino acids with the corresponding codon from the DNA sequence.

Pairwise sequence comparison algorithms in common use are adequate to detect similarities between polypeptide sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous polypeptides with the same fold and similar biological function have often diverged to the point where traditional sequence-based comparison fails to detect their relationship (Lindahl and Elofsson, 2000, *J. Mol. Biol.* 295: 613-615). Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide of interest has one or more (several) representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide of interest, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Eng.* 11: 739-747), and implementations of these algorithms can additionally be utilized to query structure databases with a structure of interest in order to discover possible structural homologs (e.g., Holm and Park, 2000, *Bioinformatics* 16: 566-567). These structural alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the malate dehydrogenase variants of the present invention, the nomenclature described below is adapted for ease of reference. In all cases, the accepted IUPAC single letter or triple letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, new inserted amino acid. Accordingly the insertion of lysine after glycine at position 195 is designated "Gly195GlyLys" or "G195GK". Multiple insertions of amino acids are designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would thus be:

| Parent: | Variant: |
|---------|----------|
| 195     | 195 195a 195b |
| G       | G-K-A    |

Parent Malate Dehydrogenases and Polynucleotides Encoding Parent Malate Dehydrogenases In the present invention, the parent malate dehydrogenase can be any malate dehydrogenase that is imported in vivo into the mitochondria of the host cell.

In one aspect, the parent malate dehydrogenase is (a) a malate dehydrogenase comprising an amino acid sequence having at least 60% sequence identity with SEQ ID NO: 18; (b) a malate dehydrogenase encoded by a polynucleotide that hybridizes under at least low stringency conditions with (i) SEQ ID NO: 17, (ii) the cDNA sequence contained in SEQ ID NO: 17, or (iii) the full-length complementary strand of (i) or (ii); or (c) a malate dehydrogenase encoded by a polynucleotide comprising a nucleotide sequence having at least 60% sequence identity with SEQ ID NO: 17, wherein the parent malate dehydrogenase comprises one or more (several) mitochondrial targeting sequences (Claros and Vincens, 1996, supra).

In one aspect, the parent malate dehydrogenase comprises or consists of an amino acid sequence having a degree of sequence identity to SEQ ID NO: 18 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which have malate dehydrogenase activity (hereinafter "homologous dehydrogenases"). In one aspect, the homologous dehydrogenase comprises an amino acid sequence that differs by no more than ten amino acids, e.g., by no more than five amino acids, by no more than four amino acids, by no more than three amino acids, by no more than two amino acids, or by one amino acid from SEQ ID NO: 18.

A substantially homologous parent malate dehydrogenase may have one or more (several) amino acid substitutions, deletions and/or insertions, as described supra.

In one aspect, the parent malate dehydrogenase comprises the amino acid sequence of SEQ ID NO: 18 or an allelic variant thereof; or a fragment thereof having malate dehydrogenase activity. In another aspect, the parent malate dehydrogenase comprises the amino acid sequence of SEQ ID NO: 18. In another aspect, the parent malate dehydrogenase consists of the amino acid sequence of SEQ ID NO: 18 or an allelic variant thereof; or a fragment thereof having malate dehydrogenase activity. In another aspect, the parent malate dehydrogenase consists of the amino acid sequence of SEQ ID NO: 18.

A fragment of SEQ ID NO: 18 is a polypeptide having one or more (several) amino acids deleted from the amino and/or carboxyl terminus of this amino acid sequence. In one aspect, a fragment contains at least 295 amino acid residues, e.g., at least 310 amino acid residues or at least 325 amino acid residues of SEQ ID NO: 18.

In another aspect, the parent malate dehydrogenase is encoded by a polynucleotide that hybridizes under at least very low stringency conditions, e.g., low stringency conditions, medium stringency conditions, medium-high stringency conditions, high stringency conditions, or very high stringency conditions with (i) SEQ ID NO: 17, (ii) the cDNA sequence contained in SEQ ID NO: 17, (iii) a subsequence of (i) or (ii), or (iv) the full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). The subsequence may encode a polypeptide fragment having malate dehydrogenase activity.

A subsequence of SEQ ID NO: 17, or a homolog thereof, is a nucleotide sequence where one or more (several) nucleotides have been deleted from the 5'- and/or 3'-end. In one aspect, a subsequence contains at least 885 nucleotides, e.g., at least 930 nucleotides or at least 975 nucleotides of SEQ ID NO: 17.

The parent enzyme may also be an allelic variant or artificial variant of a malate dehydrogenase.

The polynucleotide of SEQ ID NO: 17; or a subsequence thereof; as well as the amino acid sequence of SEQ ID NO: 18; or a fragment thereof; may be used to design nucleic acid probes to identify and clone DNA encoding parent malate dehydrogenases from strains of different genera or species, as described supra.

A genomic DNA or cDNA library prepared from such other organisms may be screened for DNA that hybridizes with the probes described above and encodes a malate dehydrogenase, as described supra.

In one aspect, the nucleic acid probe is SEQ ID NO: 17. In another aspect, the nucleic acid probe is a polynucleotide sequence that encodes SEQ ID NO: 18, or a subsequence thereof.

For long probes of at least 100 nucleotides in length, very low to very high stringency and washing conditions are defined as described supra.

For short probes that are about 15 nucleotides to about 70 nucleotides in length, stringency and washing conditions are defined as described supra.

In another aspect, the parent malate dehydrogenase is encoded by a polynucleotide comprising or consisting of a nucleotide sequence having a degree of sequence identity to SEQ ID NO: 17 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which encodes a polypeptide having malate dehydrogenase activity.

The parent malate dehydrogenase may be obtained from microorganisms of any genus. For purposes of the present invention, the term "obtained from" as used herein in connection with a given source shall mean that the parent malate dehydrogenase encoded by a polynucleotide is produced by the source or by a cell in which the polynucleotide from the source has been inserted.

In one aspect, the parent malate dehydrogenase may be a bacterial, a yeast, or a filamentous fungal malate dehydrogenase obtained from the microorganisms described herein in the C4 dicarboxylic acid transporter section.

In another aspect, the parent malate dehydrogenase is an *Aspergillus oryzae* malate dehydrogenase, e.g., the *Aspergillus oryzae* malate dehydrogenase of SEQ ID NO: 18.

The parent malate dehydrogenase may also be identified and obtained from other sources including microorganisms isolated from nature (e.g., soil, composts, water, etc.) or DNA samples obtained directly from natural materials (e.g., soil, composts, water, etc) as described supra.

The parent malate dehydrogenase can also include fused polypeptides or cleavable fusion polypeptides, as described supra.

Techniques used to isolate or clone a polynucleotide encoding a parent malate dehydrogenase are described supra.

In one aspect, the isolated polynucleotide comprises or consists of SEQ ID NO: 17. In another aspect, the isolated polynucleotide encodes a parent malate dehydrogenase comprising or consisting of SEQ ID NO: 18. The present invention also encompasses nucleotide sequences that encode polypeptides comprising or consisting of the amino acid sequence of SEQ ID NO: 18, which differ from SEQ ID NO: 17 by virtue of the degeneracy of the genetic code. The present invention also relates to subsequences of SEQ ID NO: 17 that encode fragments of SEQ ID NO: 18 that have malate dehydrogenase activity.

In another aspect, the isolated polynucleotide can be a mutant polynucleotide comprising or consisting of at least one mutation in SEQ ID NO: 17, in which the mutant nucleotide sequence encodes SEQ ID NO: 18.

In another aspect, the isolated polynucleotide comprises or consists of a nucleotide sequence that has a degree of sequence identity to SEQ ID NO: 17 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity, which encodes a parent polypeptide having malate dehydrogenase activity.

In another aspect, the isolated polynucleotide encoding a parent malate dehydrogenase hybridizes under at least very low stringency conditions, e.g., low stringency conditions, medium stringency conditions, medium-high stringency conditions, high stringency conditions, or very high stringency conditions with (i) SEQ ID NO: 17, (ii) the cDNA sequence contained in SEQ ID NO: 17, or (iii) the full-length complementary strand of (i) or (ii); or allelic variants and subsequences thereof (Sambrook et al., 1989, supra), as defined herein.

In another aspect, the isolated polynucleotide encoding a parent malate dehydrogenase is obtained by (a) hybridizing a population of DNA under very low, low, medium, medium-high, high, or very high stringency conditions with (i) SEQ ID NO: 17, (ii) the cDNA sequence contained in SEQ ID NO: 17, or (iii) the full-length complementary strand of (i) or (ii); and (b) isolating the hybridizing polynucleotide, which encodes the parent polypeptide having malate dehydrogenase activity.

Other parent malate dehydrogenases that can be used to practice the present invention include, but are not limited to, a *Aspergillus nidulans* malate dehydrogenase (AN6717.1; SIMS et al., 2004, *Mycol. Res.* 108: 853-857); *Aspergillus niger* malate dehydrogenase (An16g00120; Pel et al., 2007, *Nature Biotechnology* 25: 221-231); *Phytophthora infestans* malate dehydrogenase (PITG 13614.1; Calcagno et al., 2009, *Mycological Research* 113: 771-781); *Saccharomyces cerevisiae* malate dehydrogenase (YKL085W; McAlister-Henn and Thompson, 1987, *J. Bacteriol.* 169: 5157-5166); *Talaromyces emersonii* malate dehydrogenase (AF439996, AF487682; Maloney et al., 2004, *Eur. J. Biochem.* 271: 3115-3126); and *Ustilago maydis* malate dehydrogenase (um00403, um11161; McCann and Snetselaar, 2008, *Fungal Genetics and Biology* 45: S77-S87).

Preparation of Variants

Variants of a parent malate dehydrogenase can be prepared according to any mutagenesis procedure known in the art, such as site-directed mutagenesis, synthetic gene construction, semi-synthetic gene construction, etc.

Site-directed mutagenesis is a technique in which one or several mutations are created at a defined site in a polynucleotide molecule encoding the parent malate dehydrogenase. The technique can be performed in vitro or in vivo.

Synthetic gene construction entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., *Nature* 432:1050-1054) and similar technologies wherein oligonucleotides are synthesized and assembled upon photo-programmable microfluidic chips.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent malate dehydrogenase and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, for example, Scherer and Davis, 1979, *Proc. Natl. Acad. Sci. USA* 76: 4949-4955; and Barton et al., 1990, *Nucleic Acids Research* 18: 7349-4966.

Site-directed mutagenesis can be accomplished in vivo by methods known in the art. See, for example, U.S. Pat. No. 7,314,712; Storici et al., 2001, *Nature Biotechnology* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants of a parent malate dehydrogenase.

Single or multiple amino acid substitutions, deletions, and/or insertions can be made and tested using known methods of mutagenesis followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204) and region-directed mutagenesis (Derbyshire et al., 1986, *Gene* 46:145; Ner et al., 1988, *DNA* 7:127).

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error-prone PCR implication.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotide are synthesized and assembled upon photo-programmable microfluidic chips.

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Variants and Polynucleotides Encoding Malate Dehydrogenase Variants

In the present invention, variants of a parent malate dehydrogenase may comprise (i) a deletion at positions equivalent or corresponding to positions 2 to 17 or a portion thereof of SEQ ID NO: 18, and (ii) a substitution at a position equivalent to position 48 of SEQ ID NO: 18. In a preferred aspect, the variant having malate dehydrogenase activity comprises an amino acid sequence having a degree of sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least about 97%, at least 98%, at least 99% to the amino acid sequence of the parent malate dehydrogenase, e.g., SEQ ID NO: 18. In a preferred aspect, the parent malate dehydrogenase is SEQ ID NO: 18.

In one aspect, a variant of the present invention comprises deletions at positions equivalent to positions 2 to 17 of SEQ ID NO: 18 and a substitution at a position equivalent to position 48 of SEQ ID NO: 18. In another aspect, a variant of the present invention comprises a deletion at one or more (several) positions equivalent to positions 2 to 17 of SEQ ID NO: 18 and a substitution at a position equivalent to position 48 of SEQ ID NO: 18. In another aspect, a variant of the present invention comprises deletions at positions 2 to 17 of SEQ ID NO: 18 and a substitution at position 48 of SEQ ID NO: 18. In another aspect, a variant of the present invention comprises a deletion at one or more (several) positions 2 to 17 of SEQ ID NO: 18 and a substitution at position 48 of SEQ ID NO: 18. In another aspect, the variant comprises a deletion of Ala, Arg, Asn, Asp, Cys, Gln, Glu, Gly, His, Ile, Leu, Lys, Met, Phe, Pro, Ser, Thr, Trp, Tyr, or Val at positions corresponding to positions 2 to 17 and a substitution with Ala, Arg, Asn, Asp, Cys, Gln, Glu, Gly, His, Ile, Leu, Lys, Met, Phe, Pro, Ser, Thr, Trp, Tyr, or Val at a position equivalent to position 48 of SEQ ID NO: 18. In another aspect, the variant comprises a deletion of Ala, Arg, Asn, Asp, Cys, Gln, Glu, Gly, His, Ile, Leu, Lys, Met, Phe, Pro, Ser, Thr, Trp, Tyr, or Val at one or more (several) positions corresponding to positions 2 to 17 and a substitution with Ala, Arg, Asn, Asp, Cys, Gln, Glu, Gly, His, Ile, Leu, Lys, Met, Phe, Pro, Ser, Thr, Trp, Tyr, or Val at a position equivalent to position 48 of SEQ ID NO: 18. In another aspect, the variant comprises deletions of Phe, Ala, Ala, Arg, Gln, Ser, Phe, Asn, Leu, Leu, Gln, Lys, Arg, Ala, Phe, or Ser at positions equivalent to positions 2 to 17 of SEQ ID NO: 18, and Tyr as a substitution at a position equivalent to position 48 of SEQ ID NO: 18. In another aspect, the variant comprises deletions of Phe, Ala, Ala, Arg, Gln, Ser, Phe, Asn, Leu, Leu, Gln, Lys, Arg, Ala, Phe, or Ser at one or more (several) positions equivalent to positions 2 to 17 of SEQ ID NO: 18, and Tyr as a substitution at a position equivalent to position 48 of SEQ ID NO: 18. In another aspect, the variant comprises the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18. In another aspect, the variant comprises one or more (several) of the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18.

The variants may further comprise one or more (several) deletions, substitutions, and/or insertions of the amino acid sequence.

The present invention also relates to isolated polynucleotides that encode variants of a parent malate dehydrogenase, wherein the polynucleotides encode malate dehydrogenase variants comprising (i) a deletion at positions equivalent to positions 2 to 17 or a portion thereof of SEQ ID NO: 18, and (ii) a substitution at a position equivalent to position 48 of SEQ ID NO: 18, wherein the parent malate dehydrogenase is (a) a malate dehydrogenase comprising an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 18; (ii) a malate dehydrogenase encoded by a polynucleotide that hybridizes under at least very low stringency conditions, e.g., low stringency conditions, medium stringency conditions, medium-high stringency conditions, high stringency conditions, or very high stringency conditions with (i) SEQ ID NO: 17, (ii) the cDNA sequence contained in SEQ ID NO: 17, or (iii) the full-length complementary strand of (i) or (ii), wherein the variant has malate dehydrogenase activity.

In one aspect, the isolated polynucleotide encodes a malate dehydrogenase variant comprising deletions at positions equivalent to positions 2 to 17 of SEQ ID NO: 18 and a substitution at a position equivalent to position 48 of SEQ ID NO: 18. In another aspect, the isolated polynucleotide encodes a malate dehydrogenase variant comprising a deletion at one or more (several) positions equivalent to positions 2 to 17 of SEQ ID NO: 18 and a substitution at a position equivalent to position 48 of SEQ ID NO: 18. In another aspect, the isolated polynucleotide encodes a malate dehydrogenase variant comprising deletions at positions 2 to 17 of SEQ ID NO: 18 and a substitution at position 48 of SEQ ID NO: 18. In another aspect, the isolated polynucleotide encodes a malate dehydrogenase variant comprising a deletion at one or more (several) positions 2 to 17 of SEQ ID NO: 18 and a substitution at position 48 of SEQ ID NO: 18. In another aspect, the isolated polynucleotide encodes a malate dehydrogenase variant comprising a deletion of Ala, Arg, Asn, Asp, Cys, Gln, Glu, Gly, His, Ile, Leu, Lys, Met, Phe, Pro, Ser, Thr, Trp, Tyr, or Val at positions corresponding to positions 2 to 17 and a substitution with Ala, Arg, Asn, Asp, Cys, Gln, Glu, Gly, His, Ile, Leu, Lys, Met, Phe, Pro, Ser, Thr, Trp, Tyr, or Val at a position equivalent to position 48 of SEQ ID NO: 18. In another aspect, the isolated polynucleotide encodes a malate dehydrogenase variant comprising a deletion of Ala, Arg, Asn, Asp, Cys, Gln, Glu, Gly, His, Ile, Leu, Lys, Met, Phe, Pro, Ser, Thr, Trp, Tyr, or Val at of one or more (several) positions corresponding to positions 2 to 17 and a substitution with Ala, Arg, Asn, Asp, Cys, Gln, Glu, Gly, His, Ile, Leu, Lys, Met, Phe, Pro, Ser, Thr, Trp, Tyr, or Val at a position equivalent to position 48 of SEQ ID NO: 18. In another aspect, the isolated polynucleotide encodes a malate dehydrogenase variant comprising deletions of Phe, Ala, Ala, Arg, Gln, Ser, Phe, Asn, Leu, Leu, Gln, Lys, Arg, Ala, Phe, or Ser at positions equivalent to positions 2 to 17 of SEQ ID NO: 18, and Tyr as a substitution at a position equivalent to position 48 of SEQ ID NO: 18. In another aspect, the isolated polynucleotide encodes a malate dehydrogenase variant comprising deletions of Phe, Ala, Ala, Arg, Gln, Ser, Phe, Asn, Leu, Leu, Gln, Lys, Arg, Ala, Phe, or Ser at one or more (several) positions equivalent to positions 2 to 17 of SEQ ID NO: 18, and Tyr as a substitution at a position equivalent to position 48 of SEQ ID NO: 18. In another aspect, the isolated polynucleotide encodes a malate dehydrogenase variant comprising the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18. In another aspect, the isolated polynucleotide encodes a malate dehydrogenase variant comprising one or more (several) of the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18.

Pyruvate Carboxylases and Polynucleotides Encoding Pyruvate Carboxylases

In the present invention, the pyruvate carboxylase can be any pyruvate carboxylase that is suitable for practicing the present invention. In one aspect, the pyruvate carboxylase is an enzyme that is present in the cytosol of the host cell.

In one aspect, the pyruvate carboxylase is (a) a pyruvate carboxylase comprising an amino acid sequence having at least 60% sequence identity with SEQ ID NO: 27; (b) a pyruvate carboxylase encoded by a polynucleotide that hybridizes under low stringency conditions with (i) SEQ ID NO: 26, (ii) the cDNA sequence contained in SEQ ID NO: 26, or (iii) the full-length complementary strand of (i) or (ii); (c) a pyruvate carboxylase encoded by a polynucleotide comprising a nucleotide sequence having at least 60% sequence identity with SEQ ID NO: 26; (d) a pyruvate carboxylase variant comprising a substitution, deletion, and/or insertion of one or more (several) amino acids of the mature polypeptide of SEQ ID NO: 26; or (e) a fragment of the pyruvate carboxylase of (a), (b), (c), or (d) that has pyruvate carboxylase activity.

In one aspect, the pyruvate carboxylase comprises or consists of an amino acid sequence having a degree of sequence identity to SEQ ID NO: 27 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which has pyruvate carboxylase activity (hereinafter "homologous pyruvate carboxylases"). In one aspect, the homologous pyruvate carboxylase comprises an amino acid sequence that differs by no more than ten amino acids, e.g., by no more than five amino acids, by no more than four amino acids, by no more than three amino acids, by no more than two amino acids, or by one amino acid from SEQ ID NO: 27.

A substantially homologous pyruvate carboxylase may have one or more (several) amino acid substitutions, deletions and/or insertions, as described supra.

In one aspect, the pyruvate carboxylase comprises the amino acid sequence of SEQ ID NO: 27 or an allelic variant thereof; or a fragment thereof having pyruvate carboxylase activity. In another aspect, the pyruvate carboxylase comprises the amino acid sequence of SEQ ID NO: 27. In another aspect, the pyruvate carboxylase consists of the amino acid sequence of SEQ ID NO: 27 or an allelic variant thereof; or a fragment thereof having pyruvate carboxylase activity. In another aspect, the pyruvate carboxylase consists of the amino acid sequence of SEQ ID NO: 27.

In one aspect, the pyruvate carboxylase is a variant comprising a substitution, deletion, and/or insertion of one or more (several) amino acids of the mature polypeptide of SEQ ID NO: 27, as described supra. In some aspects, the total number of amino acid substitutions, deletions and/or insertions of the mature polypeptide of SEQ ID NO: 27 is not more than 10, e.g., not more than 1, 2, 3, 4, 5, 6, 7, 8 or 9. In another aspect, the total number of amino acid substitutions, deletions and/or insertions of the mature polypeptide of SEQ ID NO: 27 is 1, 2, 3, 4, 5, 6, 7, 8, 9, or 10.

In another aspect, the pyruvate carboxylase is a fragment of SEQ ID NO: 27, wherein the fragment has pyruvate carboxylase activity. In one aspect, a fragment contains at least 1020 amino acid residues, e.g., at least 1080 amino acid residues or at least 1140 amino acid residues SEQ ID NO: 27.

In a another aspect, the pyruvate carboxylase is encoded by a polynucleotide that hybridizes under at least very low stringency conditions, e.g., low stringency conditions, medium stringency conditions, medium-high stringency conditions, high stringency conditions, or very high stringency conditions with (i) SEQ ID NO: 26, (ii) the cDNA sequence contained in SEQ ID NO: 26, (iii) a subsequence of (i) or (ii), or (iv) the full-length complementary strand of (i), (ii), or (iii) (J. Sambrook, E. F. Fritsch, and T. Maniatis, 1989, supra). The subsequence may encode a polypeptide fragment having pyruvate carboxylase activity.

A subsequence of SEQ ID NO: 26, or a homolog thereof, is a nucleotide sequence where one or more (several) nucleotides have been deleted from the 5'- and/or 3'-end. In one aspect, a subsequence contains at least 3060 nucleotides, e.g., at least 3240 nucleotides or at least 3420 nucleotides of SEQ ID NO: 26.

The polynucleotide of SEQ ID NO: 26; or a subsequence thereof; as well as the amino acid sequence of SEQ ID NO: 27; or a fragment thereof; may be used to design nucleic acid probes to identify and clone DNA encoding pyruvate carboxylases from strains of different genera or species, as described supra. Such probes are encompassed by the present invention.

A genomic DNA or cDNA library prepared from such other organisms may be screened for DNA that hybridizes with the probes described above and encodes a pyruvate carboxylase, as described supra.

In one aspect, the nucleic acid probe is SEQ ID NO: 26. In another aspect, the nucleic acid probe is a polynucleotide sequence that encodes SEQ ID NO: 27, or a subsequence thereof.

For long probes of at least 100 nucleotides in length, very low to very high stringency and washing conditions are defined as described supra.

For short probes of about 15 nucleotides to about 70 nucleotides in length, stringency and washing conditions are defined as described supra.

In another aspect, the pyruvate carboxylase is encoded by a polynucleotide comprising or consisting of a nucleotide sequence having a degree of sequence identity to SEQ ID NO: 26 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, which encodes a polypeptide having pyruvate carboxylase activity.

The pyruvate carboxylases may be obtained from microorganisms of any genus. For purposes of the present invention, the term "obtained from" as used herein in connection with a given source shall mean that the pyruvate carboxylase encoded by a polynucleotide is produced by the source or by a cell in which the polynucleotide from the source has been inserted.

In one aspect, the pyruvate carboxylase may be a bacterial, a yeast, or a filamentous fungal pyruvate carboxylase obtained from the microorganisms described herein.

In another aspect, the pyruvate carboxylase is an *Aspergillus oryzae* pyruvate carboxylase, e.g., the *Aspergillus oryzae* pyruvate carboxylase of SEQ ID NO: 27.

The pyruvate carboxylase may also be identified and obtained from other sources including microorganisms isolated from nature (e.g., soil, composts, water, etc.) or DNA samples obtained directly from natural materials (e.g., soil, composts, water, etc) as described supra.

The pyruvate carboxylase can also include fused polypeptides or cleavable fusion polypeptides, as described supra.

The pyruvate carboxylase can also be a variant of a mitochondrial pyruvate carboxylase, such that in vivo importation into the mitochondria is reduced thereby increasing the level of the pyruvate carboxylase variant in the cytosol.

Techniques used to isolate or clone a polynucleotide encoding a pyruvate carboxylase are described supra.

In one aspect, the isolated polynucleotide comprises or consists of SEQ ID NO: 26. In another aspect, the isolated polynucleotide encodes a pyruvate carboxylase comprising or consisting of SEQ ID NO: 27. The present invention also encompasses nucleotide sequences that encode polypeptides comprising or consisting of the amino acid sequence of SEQ ID NO: 27, which differ from SEQ ID NO: 26 by virtue of the degeneracy of the genetic code. The present invention also relates to subsequences of SEQ ID NO: 26 that encode fragments of SEQ ID NO: 27 that have pyruvate carboxylase activity.

In another aspect, the isolated polynucleotide can be a mutant polynucleotide comprising or consisting of at least one mutation in SEQ ID NO: 26, in which the mutant nucleotide sequence encodes SEQ ID NO: 27.

In another aspect, the isolated polynucleotide comprises or consists of nucleotide sequences that have a degree of sequence identity to SEQ ID NO: 26 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity, which encode an active pyruvate carboxylase.

In another aspect, the isolated polynucleotide encoding a pyruvate carboxylase hybridizes under at least very low stringency conditions, e.g., low stringency conditions, medium stringency conditions, medium-high stringency conditions, high stringency conditions, or very high stringency conditions with (i) SEQ ID NO: 26, (ii) the cDNA sequence contained in SEQ ID NO: 26, or (iii) the full-length complementary strand of (i) or (ii); or allelic variants and subsequences thereof (Sambrook et al., 1989, supra), as defined herein.

In another aspect, the isolated polynucleotide encoding a pyruvate carboxylase is obtained by (a) hybridizing a population of DNA under very low, low, medium, medium-high, high, or very high stringency conditions with (i) SEQ ID NO: 26, (ii) the cDNA sequence contained in SEQ ID NO: 26, or (iii) the full-length complementary strand of (i) or (ii); and (b) isolating the hybridizing polynucleotide, which encodes a polypeptide having pyruvate carboxylase activity.

Other pyruvate carboxylases that can be used to practice the present invention include, but are not limited to, a *Aspergillus clavatus* NRRL 1 pyruvate carboxylase (XP_001271664; Direct Submission, Submitted (Oct. 26, 2006), The Institute for Genomic Research, 9712 Medical Center Drive, Rockville, Md. 20850, USA); *Aspergillus fumigatus* Af293 pyruvate carboxylase (XP_752054; Nierman et al., 2005, *Nature* 438: 1151-1156); *Aspergillus nidulans* FGSC A4 pyruvate carboxylase (XP_662066; Galagan et al., 2005, *Nature* 438: 1105-1115); *Aspergillus niger* pyruvate carboxylase (An15g02820; Pel et al., 2007, *Nature Biotechnology* 25: 221-231; ASPNG 5061; Panneman et al., Submitted (July 1998) to the EMBL/GenBank/DDBJ databases); *Aspergillus terreus* pyruvate carboxylase (O93918; Direct Submission, Submitted (October 1998) The Institute for Genomic Research, 9712 Medical Center Drive, Rockville, Md. 20850, USA); *Magnaporthe grisea* 70-15 pyruvate carboxylase (XP_367852; Direct Submission, Submitted (Sep. 26, 2005) Broad Institute of MIT and Harvard, 320 Charles Street, Cambridge, Mass. 02142, USA); *Neurospora crassa* OR74A pyruvate carboxylase (XP_965636; Galagan et al., 2003, *Nature* 422: 859-868); *Rhizopus oryzae* pyruvate carboxylase (RO3G_06931.1); *Saccharomyces cerevisiae* pyruvate carboxylase (NP_009777; Gaffeau et al., 1996, *Science* 274: 546-547); *Schizosaccharomyces pompe* pyruvate carboxylase (NP_595900; Direct Submission, Submitted (29 Jun. 2007) European *Schizosaccharomyces* genome sequencing project, Sanger Institute, The Wellcome Trust Genome Campus, Hinxton, Cambridge CB10 1SA); and *Ustilago maydis* pyruvate carboxylase (um01054; McCann and Snetselaar, 2008, *Fungal Genetics and Biology* 45: S77-S87).

Nucleic Acid Constructs

The present invention also relates to nucleic acid constructs comprising an isolated polynucleotide encoding a C4 dicarboxylic acid transporter, an isolated polynucleotide encoding a malate dehydrogenase, and/or an isolated polynucleotide encoding a pyruvate carboxylase operably linked to one or more (several) control sequences that direct the expression of the coding sequence in a suitable host cell under conditions compatible with the control sequences.

An isolated polynucleotide encoding a C4 dicarboxylic acid transporter, a malate dehydrogenase, and/or a pyruvate carboxylase may be manipulated in a variety of ways to provide for expression of the polypeptide(s). Manipulation of a polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a C4 dicarboxylic acid transporter, malate dehydrogenase, and/or a pyruvate carboxylase. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs in a filamentous fungal host cell are promoters obtained from the genes for *Aspergillus oryzae* TAKA amylase, *Aspergillus oryzae* translation elongation factor, *Aspergillus oryzae* phosphoglycerate kinase, *Aspergillus oryzae* glycerol-3-phosphate dehydrogenase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans acetamidase, Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus nidulans* triose phosphate isomerase); and mutant, truncated, and hybrid promoters thereof.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence; a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding sequence that codes for an amino acid sequence linked to the amino terminus of a polypeptide and directs the encoded polypeptide into a cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Saccharomyces cerevisiae* alpha-factor, *Rhizomucor miehei* aspartic proteinase, and *Myceliophthora thermophila* lactase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound.

Regulatory systems in filamentous fungi include the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a an isolated polynucleotide encoding a C4 dicarboxylic acid transporter, an isolated polynucleotide encoding a malate dehydrogenase, and/or an isolated polynucleotide encoding a pyruvate carboxylase, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors may contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors may contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements may contain a sufficient number of nucleic acids, such as 100 to 10,000 base pairs, e.g., 400 to 10,000 base pairs or 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in a filamentous fungal cell are AMA1 and ANSI. (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The present invention also relates to recombinant filamentous fungal host cells, comprising an isolated polynucleotide encoding a C4 dicarboxylic acid transporter, an isolated polynucleotide encoding a malate dehydrogenase, and/or an isolated polynucleotide encoding a pyruvate carboxylase, a promoter, and transcriptional and translational stop signals, which are advantageously used in the recombinant production of the polypeptides. A vector comprising such a polynucleotide(s) is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any filamentous fungal cell useful in the recombinant production of C4 dicarboxylic acids.

"Filamentous fungi" include all filamentous forms of the subdivision Eumycota and Oomycota (as defined by Hawksworth et al., In, *Ainsworth and Bisby's Dictionary of The Fungi*, 8th edition, 1995, CAB International, University Press, Cambridge, UK). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus flavus, Aspergillus fumigatus, Aspergillus foetidus, Aspergillus japonicus, Aspergillus nidulans, Aspergillus niger, Aspergillus oryzae, Aspergillus parasiticus,* or *Aspergillus sojae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum,*

Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Rhizopus oryzae, Thielavia terrestris, Trametes villosa, Trametes versicolor, Trichoderma harzianum, Trichoderma koningii, Trichoderma longibrachiatum, Trichoderma reesei, or Trichoderma viride cell.

In a preferred aspect, the Aspergillus host cell is Aspergillus oryzae.

Filamentous fungal cells may be transformed by a process involving protoplast formation, transformation of the protoplasts, and regeneration of the cell wall in a manner known per se. Suitable procedures for transformation of Aspergillus and Trichoderma host cells are described in U.S. Pat. No. 5,536,661 and Yelton et al., 1984, Proceedings of the National Academy of Sciences USA 81: 1470-1474. Suitable methods for transforming Fusarium species are described by Malardier et al., 1989, Gene 78: 147-156, and U.S. Pat. No. 5,837,847.

The present invention is further described by the following examples that should not be construed as limiting the scope of the invention.

EXAMPLES

Chemicals used as buffers and substrates were commercial products of at least reagent grade.

Fungal Strains

Aspergillus oryzae NRRL 3488 (or ATCC 56747) was used as source of a C4 dicarboxylic acid transporter gene, a pyruvate carboxylase gene, and malate dehydrogenase genes, mdh1 and mdh3, and for production of malic acid.

Media

YEG medium was composed of 20 g glucose, 5 g yeast extract, and deionized water to 1 liter.

COVE plates were composed of 1 M sucrose, 2% COVE salt solution, 10 mM acetamide, 15 mM CsCl, and 25 g/l Agar Noble.

COVE salt solution was composed of 26 g KCl, 26 g $MgSO_4.7H_2O$, 76 g $KH_2PO_4$, 50 ml of COVE trace elements solution, and deionized water to 1 liter.

COVE trace elements solution was composed of 0.04 g $Na_2B_4O_7.10H_2O$, 0.04 g $CuSO_4.5H_2O$, 1.2 g $FeSO_4.7H_2O$, 0.7 g $MnSO_4.H_2O$, 0.8 g $Na_2MoO_2.2H_2O$, 10 g $ZnSO_4.7H_2O$ and deionized water to 1 liter.

Seed medium B was composed of 30 g glucose, 3 g Bacto Peptone, 560 mg $KH_2PO_4$, 560 mg $K_2HPO_4$, 925 mg $NaH_2PO_4.H_2O$, 820 mg $Na_2HPO_4$, 75 mg $MgSO_4.7H_2O$, 75 mg $CaCl_2.H_2O$, 0.75 ml of 1000× Micronutrient Solution, and deionized water to 1 liter.

Acid production medium C was composed of 100 g glucose, 80 g $CaCO_3$, 6 g Bacto Peptone, 150 mg $KH_2PO_4$, 150 mg $K_2HPO_4$, 100 mg $MgSO_4.7H_2O$, 100 mg $CaCl_2.H_2O$, 1 ml 1000× Micronutrient Solution, and deionized water to 1 liter.

1000× Micronutrient Solution was composed of 5 g NaCl, 5 g $FeSO_4.7H_2O$, 1 g citric acid, and deionized water to 1 liter.

PDA plates were composed of 39 g/l potato dextrose agar.

2XYT+amp plates were composed of 16 g tryptone, 10 g yeast extract, 5 g NaCl, 100 mg ampicillin, 15 g Bacto agar, and deionized water to 1 liter.

Example 1

Cloning of the Aspergillus oryzae NRRL 3488 C4 Dicarboxylic Acid Transporter Gene mae3 and Construction of Expression Vectors pShTh104/mae3

The malic acid transporter gene, mae3, was cloned from Aspergillus oryzae NRRL 3488 genomic DNA by PCR amplification using primers homologous to Aspergillus oryzae ATCC 42149 predicted C4 dicarboxylic acid transporter gene model number A0090023000318 (Galagan et al., 2005, Nature 438: 1105-1115).

Genomic DNA from Aspergillus oryzae NRRL 3488 was isolated by inoculating 100 ml of YEG medium in a shake flask with $2 \times 10^6$ spores and incubating the flask at 37° C. overnight with shaking at 200 rpm. The mycelia were harvested by filtration using a MIRACLOTH® (Calbiochem, San Diego, Calif., USA) lined funnel and approximately 2 g of mycelia were recovered and frozen in liquid nitrogen. The mycelia were disrupted by grinding in a cold mortar and pestle. Genomic DNA was isolated from the powdered mycelia using a DNeasy® Plant Maxi Kit (QIAGEN Inc., Valencia, Calif., USA) according to the manufacturer's instructions. The Aspergillus oryzae mae3 gene was amplified using primer 065266 and primer 065267 shown below.

```
Primer 065266:
                                      (SEQ ID NO: 1)
5'-GTGATAGAACATCGTCCATAATGCTGACACCTCCCAAGTT-3'

Primer 065267:
                                      (SEQ ID NO: 2)
5'-AGTCACCTCTAGTTAATTAATTACTAATCAGATACATCCTCAT-3'
```

The amplification reactions were performed using an EXPAND® High Fidelity PCR System (Roche, Indianapolis, Ind., USA) according to manufacturer's instructions. Each PCR reaction contained 47 ng of Aspergillus oryzae NRRL 3488 genomic DNA, 200 µM dNTPs, 50 pM of primer 065266, 50 pM primer 065267, 1× EXPAND® reaction buffer (Roche, Indianapolis, Ind., USA), and 2.6 units of EXPAND® High Fidelity enzyme mix (Roche, Indianapolis, Ind., USA) in a final volume of 50 µl. The amplification reactions were incubated in an EPPENDORF® MASTERCYCLER® (Eppendorf Scientific Inc., Westbury, N.Y., USA) programmed for 1 cycle at 94° C. for 2 minutes; 30 cycles each at 94° C. for 15 seconds, 60° C. for 30 seconds, and 72° C. for 1 minute; and 1 cycle at 72° C. for 7 minutes.

The PCR product was purified by 1% agarose gel electrophoresis using 50 mM Tris base-50 mM acetate-0.1 mM disodium EDTA (TAE) buffer. A fragment of approximately 1.1 kb was excised from the gel and extracted from the agarose using a QIAQUICK® Gel Extraction Kit (QIAGEN Inc., Valencia, Calif., USA). DNA sequence analysis was used to confirm the integrity of the mae3 coding sequence using primers 996270, 065067, 065130, 065129 shown below.

```
Primer 996270:
5'-CTATAGCGAAATGGATTGATTGTCT-3'  (SEQ ID NO: 3)

Primer 065067:
5'-TGACCTTCCACGCTGACCAC-3'       (SEQ ID NO: 4)

Primer 065130:
5'-CTAATCAGATACATCCTCA-3'        (SEQ ID NO: 5)

Primer 065129:
5'-ATGCTGACACCTCCCAAGT-3'        (SEQ ID NO: 6)
```

Figure 2:
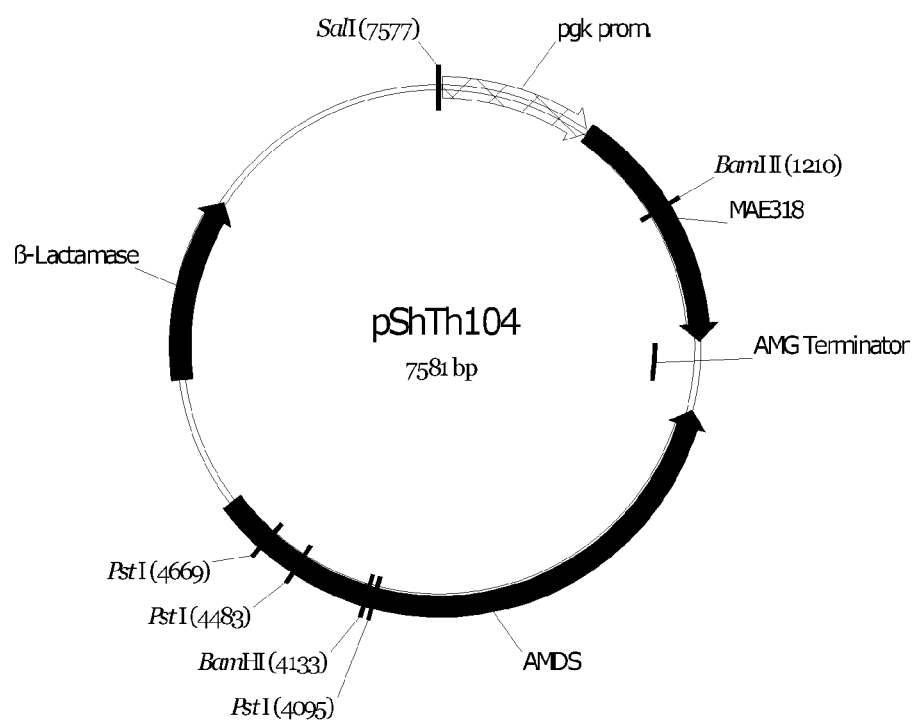
FIG. 2 shows a restriction map of pShTh104.

The 1.1 kb fragment was then cloned into Sex AI/Mung bean nuclease and Pac I digested pShTh60 (FIG. 1) using an IN-FUSION™ Cloning Kit (Clontech, Mountain View, Calif., USA) according to the manufacturer's instructions resulting in plasmid pShTh104 (FIG. 2). Plasmid pShTh60 is an expression vector comprising the *Aspergillus oryzae* Pgk promoter and the *Aspergillus niger* glucoamylase terminator. Plasmid pShTh104 was isolated using a QIAfilter Maxi Plasmid Isolation Kit (QIAGEN Inc., Valencia, Calif., USA).

Example 2

Characterization of *Aspergillus oryzae* NRRL 3488 mae3 C4 Dicarboxylic Acid Transporter Gene DNA sequencing of the *Aspergillus oryzae* NRRL 3488 C4 dicarboxylic acid transporter gene mae3 was performed with an ABI3130XL DNA Analyzer (Applied Biosystems, Inc., Foster City, Calif., USA) using the primer walking technique with dye-terminator chemistry (Giesecke et al., 1992, *J. Virol. Methods* 38: 47-60).

The nucleotide sequence (SEQ ID NO: 7) and deduced amino acid sequence (SEQ ID NO: 8) of the *Aspergillus oryzae* NRRL 3488 C4 dicarboxylic acid transporter mae3 gene are shown in FIG. 3. The genomic coding sequence of 1143 bp (including stop codon) encodes a polypeptide of 380 amino acids with a predicted mass of 42 kDa. The gene contains no introns.

A comparative pairwise global alignment of amino acid sequences in public databases was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Aspergillus oryzae* NRRL 3488 C4 dicarboxylic acid transporter mae3 gene shares 29.5% sequence identity to the deduced amino acid sequence of the *Schizosaccharomyces pombe* C4 dicarboxylic acid transporter gene (mae1; GenBank accession number U21002).

Example 3

Transformation of pShTh104 into *Aspergillus oryzae* NRRL 3488

Protoplasts of *Aspergillus oryzae* NRRL 3488 were prepared by inoculating approximately $2 \times 10^7$ spores into 100 ml of YEG medium and incubating the flask at 27° C. for 16-18 hours at 140 rpm. Mycelia were collected by pouring the culture through a sterile funnel lined with MIRACLOTH® and rinsing with 50 ml of 0.7 M KCl. The washed mycelia were resuspended in a 125 ml flask containing 20 ml of protoplasting solution composed of 5 mg of GLUCANEX™ (Novozymes A/S, Bagsværd, Denmark) and 0.5 mg of chitinase (Sigma Chemical Co., St. Louis, Mo., USA) per ml of 0.7 M KCl (filter sterilized) and incubated at 34° C. for 30 minutes with mixing at 80 rpm. The protoplasting solution was poured through a sterile funnel lined with MIRACLOTH® and rinsed with 50 ml of STC buffer (1 M sorbitol-10 mM Tris-HCl pH 6.5-10 mM $CaCl_2$). The flow-through was collected in two 50 ml polypropylene tubes, which were centrifuged at 1300×g for 10 minutes at room temperature. The supernatants were discarded and the protoplast pellets were resuspended in 20 ml of STC buffer. The protoplasts were washed by two rounds of resuspending the pellets in 20 ml of STC buffer and centrifugation at 1300×g for 10 minutes at room temperature. The final pellets were resuspended in 2 ml of STC buffer. The protoplasts were counted by removing a 10 µl sample and counting them in a hemacytometer (VWR, West Chester, Pa., USA). The volume was adjusted with STC buffer to obtain a protoplast concentration of $2 \times 10^7$ per ml.

Six transformation reactions were prepared for each expression vector. For each transformation reaction, 100 µl of protoplast preparation were transferred to a 12 ml polypropylene tube. Five micrograms of pShTh104 and 250 µl of polyethylene glycol (PEG) were added and gently mix by rotating the tube. The reaction was incubated at 37° C. for 30 minutes. Transformations were diluted with 3 ml of STC buffer and the entire amounts were plated onto COVE plates. The plates were incubated at 30° C. for 7-10 days. Thirty transformants of the resulting transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 4

Production of Malic Acid in Shake Flask Cultures

Spores from each transformant described in Example 3 and *Aspergillus oryzae* NRRL 3488 as a control were plated onto individual COVE plates and allowed to sporulate at 34° C. for 5 to 7 days. Spores were collected in 0.1% TWEEN® 80 and counted using a hemacytometer. Seed cultures were prepared in 250 ml flasks containing 100 ml of seed medium B and inoculated with $2 \times 10^8$ total spores. Seed cultures were grown for approximately 17 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 2-10 days.

Example 5

HPLC Quantitation of Malic Acid of Shake Flask Cultures

Quantitation of malic acid for the shake flask cultures of Example 4 was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5µ C18 125 Å 205×4.6 mm ID column and AQ C18 4×3.0 mm Security Guard Cartridge (Phenomenex, Inc., Torrance, Calif., USA). The mobile phase consisted of 10% methanol (HPLC grade) and 90% 145 mM phosphate pH 1.5 buffer.

Whole culture samples were removed and diluted 1:10 in HPLC Running Buffer composed of 850 ml of 64 mM phosphate buffer and 150 ml of methanol pH 1.65. The samples were then filtered through a 25 mm 0.45 micron polyethersulfone membrane (Whatman, Florham Park, N.J., USA) and 1.5 ml of the filtrates were placed into HPLC vials for acid analysis. The remaining amount of the shake flask cultures were filtered through 3 layers of cheese cloth and rinsed three times with 10 volumes of double distilled sterile water to remove insoluble $CaCO_3$. Cell pellets were harvested from the cheese cloth, placed into a 15 ml culture tube and stored at −20° C.

RP-HPLC was performed using an injection volume of 10 µl at a flow rate of 0.7 ml/minute (isocratic) with a column temperature of 25° C. and run time of 11 minutes. Detection was set at 210 nm, 8 nm bandwidth, with the reference at 360 nm, 40 nm bandwidth. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation (RSD) for replicate injections was ≤5%. Malic acid showed $R^2 \geq 0.9999$ Table 1 shows the relative increase in malic acid titer of transformants *Aspergillus oryzae* ShTh1040-8 and *Aspergillus oryzae* ShTh1040-28 compared to malic acid production of *Aspergillus oryzae* NRRL 3488 as a control after 5 days of shake flask growth. *Aspergillus oryzae* ShTh1040-8 and *Aspergillus oryzae* ShTh1040-28, each containing the heterologous mae3 C4 dicarboxylic acid transporter gene, produced a 2.1-fold and 2.2-fold increase in malic acid titer, respectively, compared to *Aspergillus oryzae* NRRL 3488.

TABLE 1

| Strain | Relative titer of malic acid | % CV |
|---|---|---|
| NRRL 3488 | 1 | 2.70% |
| ShTh1040-8 | 2.1 | 12.60% |
| ShTh1040-28 | 2.2 | 6.10% |

Example 6

Fermentation of *Aspergillus oryzae* ShTh1040 Strains

*Aspergillus oryzae* transformants designated ShTh1040-8, ShTh1040-28, and *Aspergillus oryzae* NRRL 3488 (control) were grown for approximately 7 days at 32° C. on PDA plates. A 5-6 ml volume of sterile 50 mM sodium phosphate buffer (pH 6.8) containing 0.1% TWEEN® 80 was added to each plate and spores were suspended by scraping with an inoculating loop. Each suspension was transferred by pipette to a 50 ml conical tube. For each tube, 25 ml of sterile sodium phosphate buffer was added to a 500 ml unbaffled flask containing 75 ml of seed medium, which was then inoculated with 2 ml of spore suspension. The seed medium was composed of 40 g glucose, 4.0 g (NH$_4$)$_2$SO$_4$, 0.75 g KH$_2$PO$_4$, 0.75 g K$_2$HPO$_4$, 0.1 g MgSO$_4$.7H$_2$O, 0.1 g CaCl$_2$.2H$_2$O, 0.005 g FeSO$_4$.7H$_2$O, 0.005 g NaCl, and deionized water to 1 liter. The flasks were then incubated at 32° C. and 180 rpm for about 24 hours. Three seed flasks were combined to supply the 144 ml inoculum required per tank.

Three-liter fermentors containing 1.8 liters of medium were individually inoculated by introducing 144 ml (8%) of the seed culture broth from three combined seed flasks of either *Aspergillus oryzae* transformant ShTh1040-8, *Aspergillus oryzae* transformant ShTh1040-28, or *Aspergillus oryzae* NRRL 3488. The medium was composed of 120 g glucose, 90 g CaCO$_3$, 6 g Bacto peptone, 0.150 g KH$_2$PO$_4$, 0.150 g K$_2$HPO$_4$, 0.10 g MgSO.7H$_2$O, 0.10 g CaCl$_2$-2H$_2$O, 0.005 g FeSO$_4$.7H$_2$O, 0.005 g NaCl, and deionized water to 1 liter.

The fermentors were equilibrated at 32±0.1° C. and stirred at 500 rpm. Inlet air flow was maintained at 1 v/v/m. No acid or base additions were used for pH control.

Samples were withdrawn daily and analyzed for malic acid production. Fermentations were completed after 7 days.

Example 7

HPLC Quantitation of Malic Acid of Fermentations

Quantitation of malic acid for the fermentations of Example 6 was performed as described in Example 5.

Table 2 shows the relative increase in malic acid titer of transformants *Aspergillus oryzae* ShTh1040-8 and *Aspergillus oryzae* ShTh1040-28 compared to malic acid production of *Aspergillus oryzae* NRRL 3488 as a control. *Aspergillus oryzae* ShTh1040-8 and *Aspergillus oryzae* ShTh1040-28, each containing the heterologous mae3 C4 dicarboxylic acid transporter gene, produced a 1.98-fold and 2.18-fold increase in malic acid titer, respectively, compared to *Aspergillus oryzae* NRRL 3488.

TABLE 2

| Transformant | Relative Malic Acid Titer |
|---|---|
| NRRL 3488 | 1.00 |
| ShTh1040-28 | 1.98 |
| ShTh1040-8 | 2.18 |

Example 8

Cloning of the *Aspergillus oryzae* NRRL 3488 Malate Dehydrogenase genes and Construction of Expression Vectors pShTh71 and pShTh73

Malate dehydrogenase genes mdh1 and mdh3 were cloned from *Aspergillus oryzae* NRRL 3488 genomic DNA by PCR amplification using primers homologous to the mdh1 and mdh3 gene models (AO090005000438, AO090701000013, respectively) found in the published *Aspergillus oryzae* ATCC 42149 genome sequence (Galagan et al., 2005, *Nature* 438: 1105-1115).

The *Aspergillus oryzae* mdh1 gene was amplified using primers 062390 and 062391, and the *Aspergillus oryzae* mdh3 gene was amplified using primers 062388 and 062389 shown below. *Aspergillus oryzae* NRRL 3488 was grown by inoculating 100 ml of YEG medium in a shake flask with $2 \times 10^6$ spores and incubating the flask at 37° C. overnight with shaking at 200 rpm. The mycelia were harvested using a MIRACLOTH® lined funnel and approximately 2 g of tissue was recovered and frozen in liquid nitrogen. The mycelia were disrupted by grinding in a cold mortar and pestle. Genomic DNA was isolated from the powdered mycelia using a DNeasy® Plant Maxi Kit according to the manufacturer's instructions.

Primer 062390:

(SEQ ID NO: 9)
5'-ACACAACTGGCCATGTTCGCTGCTCGCCAGTCTTTCAACCTC
CTCCAGA-3'

Primer 062391:

(SEQ ID NO: 10)
5'-AGTCACCTCTAGTTAATTAATTATTAAGGGTTGGCCTTGACGAAGT
CAATACCCTTCTGA-3'

-continued

Primer 062388:
(SEQ ID NO: 11)
5'-ACACAACTGGCCATGGTCAAAGCTGGTGAGTTAGCAATCCTT

AACAGAT-3'

Primer 062389:
(SEQ ID NO: 12)
5'-AGTCACCTCTAGTTAATTAATTATTACTTTGGTGGTGGGTTCTTAAC

GAAGTCGATGCCT-3'

The amplification reactions were performed using an EXPAND® High Fidelity PCR System according to the manufacturer's instructions. Each PCR reaction contained 47 ng of *Aspergillus oryzae* NRRL 3488 genomic DNA, 200 µM dNTPs, 50 µM forward primer, 50 µM reverse primer, 1× EXPAND® reaction buffer, and 2.6 units of EXPAND® High Fidelity enzyme mix in a final volume of 50 µl. The amplification reactions were incubated in an EPPENDORF® MASTERCYCLER® programmed for 1 cycle at 94° C. for 2 minutes; 10 cycles each at 94° C. for 15 seconds, 62.2° C. for 30 seconds, and 72° C. for 1 minute; 20 cycles each at 94° C. for 15 seconds, 62.2° C. for 30 seconds, and 72° C. for 1 minute plus 0.5 second for each successive cycle; and 1 cycle at 72° C. for 7 minutes.

PCR products from each of the amplification reactions were purified by 1% agarose gel electrophoresis in TAE buffer (50 mM Tris base-50 mM acetate-0.1 mM disodium EDTA). A fragment of approximately 1.3 kb from each amplification reaction was excised from the gels and agarose extracted using a QIAQUICK® Gel Extraction Kit. DNA sequence analysis employing an ABI3130XL DNA Analyzer was used to confirm the integrity of the mdh1 and mdh3 coding sequences using primers 62399, 62400, 62396, 62393 shown below.

```
Primer 62399:
5'-CTTTGGTGTCACCACACTGG-3'      (SEQ ID NO: 13)

Primer 62400:
5'-GGGATTTGAACAGCAGAAGG-3'      (SEQ ID NO: 14)

Primer 62396:
5'-CTTAGCAAGGTCGCGGACAATGG-3'   (SEQ ID NO: 15)

Primer 62393:
5'-GGCACTGGGAATTGAATAC-3'       (SEQ ID NO: 16)
```

Figure 4:
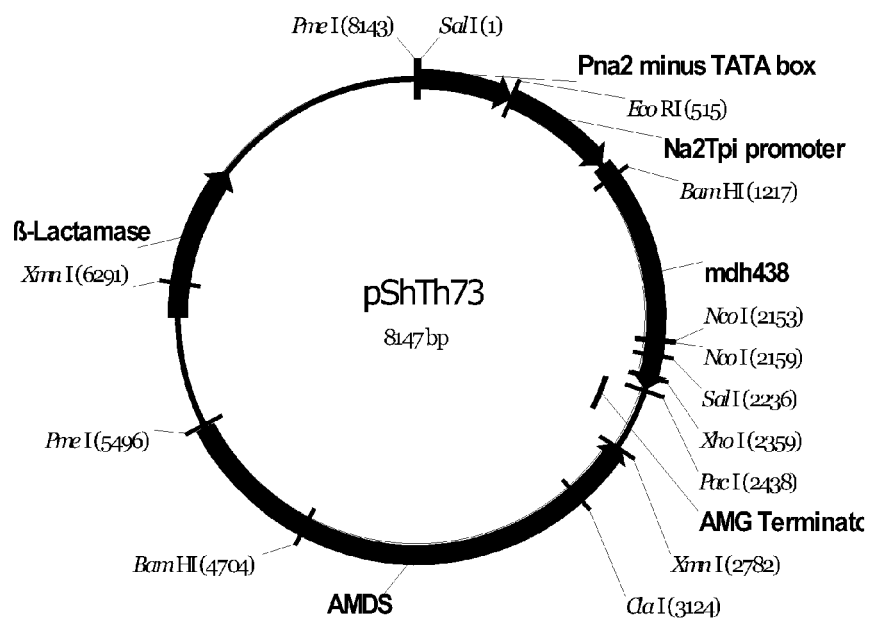
FIG. 4 shows a restriction map of pShTh73.
Figure 6:
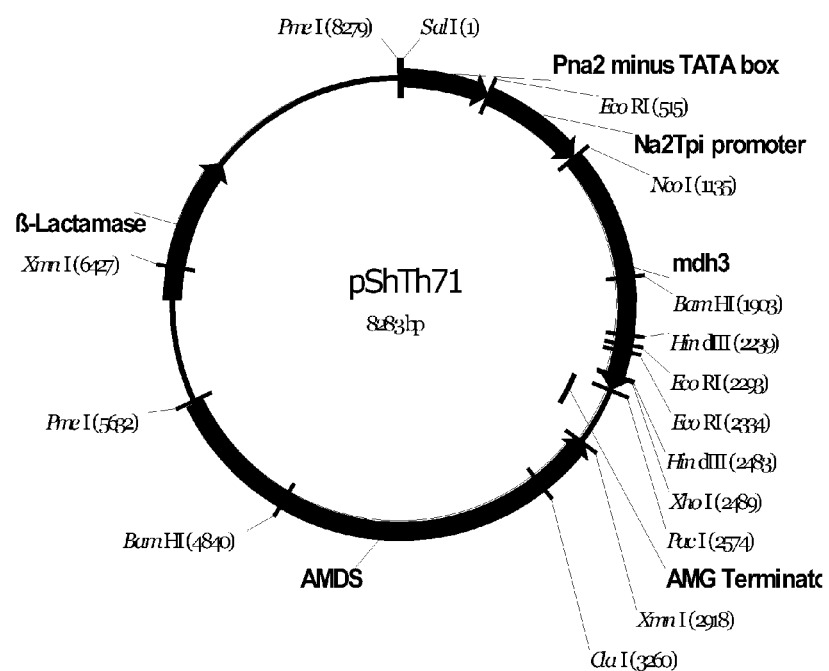
FIG. 6 shows a restriction map of pShTh71.

Each 1.3 kb fragment was then cloned into Nco I and Pac I digested pBM120a (WO 2008/008950) using an In-Fusion™ Cloning Kit according to the manufacturer's instructions resulting in plasmids pShTh73 (FIG. 4) and pShTh71 (FIG. 6) for mdh1 and mdh3, respectively. Plasmid pBM120a is an expression vector comprising the NA2-tpi promoter (a hybrid of the promoters from the genes for *Aspergillus niger* neutral alpha-amylase and *Aspergillus nidulans* triose phosphate isomerase) and the *Aspergillus niger* glucoamylase terminator. Plasmids pShTh71 and pShTh73 were isolated using a QIAfilter Maxi Plasmid Isolation Kit.

Example 9

Characterization of *Aspergillus oryzae* NRRL 3488 Malate Dehydrogenase Genes

DNA sequencing of the *Aspergillus oryzae* NRRL 3488 malate dehydrogenase mdh1 and mdh3 genes was performed with an ABI3130XL DNA Analyzer using the primer walking technique with dye-terminator chemistry (Giesecke et al., 1992, *J. Virol. Methods* 38: 47-60).

The nucleotide sequence (SEQ ID NO: 17) and deduced amino acid sequence (SEQ ID NO: 18) of the *Aspergillus oryzae* NRRL 3488 malate dehydrogenase mdh1 gene are shown in FIG. 5. The genomic coding sequence of 1294 bp (including stop codon) encodes a polypeptide of 340 amino acids with a predicted mass of 36 kDa. The coding sequence is interrupted by 4 introns of 85 bp (67-151 bp), 73 bp (270-342 bp), 60 bp (493-552 bp), and 53 bp (648-700 bp). The G+C content of the mdh1 gene is 56.5% and 60.4% for the coding region.

A comparative pairwise global alignment of amino acid sequences in public databases was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Aspergillus oryzae* NRRL 3488 malate dehydrogenase mdh1 gene shares 61.9% sequence identity (excluding gaps) to the deduced amino acid sequence of the *Saccharomyces cerevisiae* malate dehydrogenase gene (MDH1; accession number YK1085W).

The nucleotide sequence (SEQ ID NO: 19) and deduced amino acid sequence (SEQ ID NO: 20) of the *Aspergillus oryzae* NRRL 3488 malate dehydrogenase mdh3 gene are shown in FIG. 7. The genomic coding sequence of 1430 bp (including stop codon) encodes a polypeptide of 330 amino acids with a predicted mass of 35 kDa. The coding sequence is interrupted by 7 introns of 57 bp (14-70 bp), 70 bp (103-172 bp), 74 bp (284-357 bp), 68 bp (446-513 bp), 58 bp (892-949 bp), 48 bp (1035-1082 bp), and 62 bp (1228-1289 bp). The G+C content of the coding region of the mdh3 gene is 50.3%.

A comparative pairwise global alignment of amino acid sequences in public databases was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Aspergillus oryzae* NRRL 3488 malate dehydrogenase mdh3 gene shares 47.8% sequence identity (excluding gaps) to the deduced amino acid sequence of the *Saccharomyces cerevisiae* malate dehydrogenase gene (MDH3; accession number YD1078C).

Example 10

Construction of Plasmids pShTh74 and pShTh75

Plasmid pShTh74 was constructed to contain a deletion of a putative mitochondrial targeting sequence encoding amino acids 2 to 17 of *Aspergillus oryzae* NRRL 3488 MDH1. Plasmid pShTh75 was constructed to contain a deletion of the predicted mitochondrial targeting sequence encoding amino acids 2 to 17 and a substitution of R48Y of MDH1. Both mutations are intended to prevent mdh1 gene product from being targeted to and imported into the mitochondria, so the malate dehydrogenase variant is localized to the cytoplasm.

Plasmid pShTh74 was constructed by PCR amplifying the mdh1 gene from *Aspergillus oryzae* NRRL 3488 genomic DNA using oligonucleotide primers 063183 shown below and primer 062391 (Example 8).

```
Primer 063183:
(SEQ ID NO: 21)
5'-ACACAACTGGCCATGGCCTCTGCCAGCCAGGTGTG-3'
```

The amplification reaction was composed of 47 ng *Aspergillus oryzae* NRRL 3488 genomic DNA, 200 μM dNTPs, 50 μM forward primer, 50 μM reverse primer, 1× EXPAND® reaction buffer, and 2.6 units EXPAND® High Fidelity enzyme mix. The amplification reaction was incubated in an EPPENDORF® MASTERCYCLER® programmed for 1 cycle at 94° C. for 3 minutes; 29 cycles each at 94° C. for 15 seconds, 62.2° C. for 30 seconds, and 72° C. for 1 minute; and 1 cycle at 72° C. for 7 minutes.

PCR products were purified by 1% agarose gel electrophoresis in TAE buffer. A 1.2 kb fragment was excised from the gel and agarose extracted using a QIAQUICK® Gel Extraction Kit, and then cloned into Nco I and Pac I digested pBM120a (WO 2008/008950) using an In-Fusion™ Cloning Kit resulting in plasmid pShTh74. DNA sequence analysis employing an ABI3130XL DNA Analyzer was used to confirm the integrity of the mdh1 DNA fragment.

Plasmid pShTh74 was mutagenized to pShTh75 using a QUIKCHANGE® II SL Site-Directed Mutagenesis Kit (Stratagene, La Jolla, Calif., USA) to contain amino acid mutation R48Y using primers 063184 and 063186 shown below. Mutation of the arginine residue to tyrosine results in disruption of an amphipathic helix that assists in targeting and transporting proteins across the mitochondrial membrane.

```
Primer 063184:
                                       (SEQ ID NO: 22)
5'-CCTCAAGCTCAACCCCTACGTTTCTGAGCTTGCCCTCTAC-3'

Primer 063186:
                                       (SEQ ID NO: 23)
5'-GTAGAGGGCAAGCTCAGAAACGTAGGGGTTGAGCTTGAGG-3'
```

Plasmids pShTh74 and pShTh75 were isolated using a QIAfilter Maxi Plasmid Isolation Kit.

Example 11

Construction of Expression Vector pSaMF21

Plasmid pSaMF21 was designed to contain the NAD-dependent malate dehydrogenase (mdh3) gene sequence (DOGAN: A0090701000013), a 1430 bp fragment from *Aspergillus oryzae*. The plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The mdh3 gene was amplified from pShTh71 using primers 067522 and 067525.

```
Primer 067522:
                                       (SEQ ID NO: 28)
5'-AGAACATCGTCCATAATGGTCAAAGCTGGTGAGTTA-3'

Primer 067525:
                                       (SEQ ID NO: 29)
5'-GTGTCAGTCACCTCTAGTTATTACTTTGGTGGTGGGTTCT-3'
```

Figure 8:
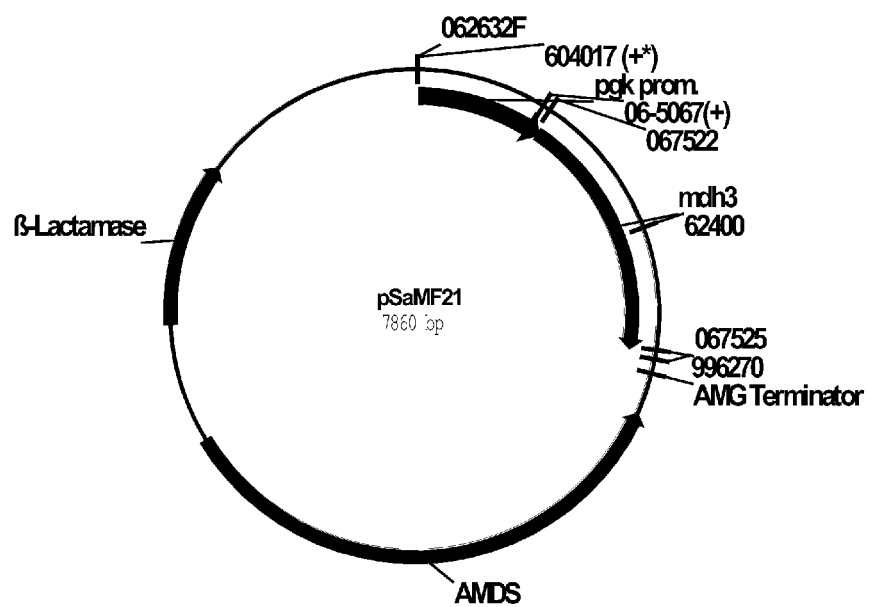
FIG. 8 shows a restriction map of pSaMF21.

The PCR reaction was composed of 5 μl 10× reaction buffer, 1 μl pShTh71 template (87 ng/μl), 1 μl primer 067522 (100 ng/μl), 1 μl primer 067525 (100 ng/μl), 1 μl dNTP mixture (10 mM), 45.5 μl deionized water, and 0.5 μl Herculase® HotStart DNA polymerase (Stratagene, La Jolla, Calif., USA). The amplification reaction was incubated in an EPPENDORF® MASTERCYCLER® programmed for 1 cycle at 95° C. for 2 minutes; 10 cycles each at 95° C. for 10 seconds, 58° C. for 30 seconds, and 72° C. for 1.5 minutes; 20 cycles each at 95° C. for 10 seconds, 50° C. for 30 seconds, and 72° C. for 1.5 minutes plus 10 seconds per cycle. The PCR reaction was subjected to a restriction digest with Dpn I for 1 hour to degrade any plasmid DNA template. The PCR product was then purified using the MinElute® PCR Purification Kit (QIAGEN Inc., Valencia, Calif., USA). The purified PCR product was inserted into the vector using an In-Fusion™ Advantage reaction composed of 2 μl 5× buffer, 0.5 μl purified PCR product (110 ng/μl), 1.7 μl gel-purified Sex AI and Pac I restriction digested pShTh60 (FIG. 1; 78 ng/μl), 1 μl In-Fusion™ enzyme and 4.8 μl deionized water. The reaction was incubated at 37° C. for 15 minutes followed by 50° C. for 15 minutes after which it was placed on ice for 5 minutes and diluted with 40 μl TE buffer resulting in pSaMF21 (FIG. 8). A 2 μl aliquot of the ligation reaction was transformed into ONE SHOT® TOP10 chemically competent *E. coli* cells (Invitrogen, San Diego, Calif., USA) according to the manufacturer's instructions. Transformants were plated onto 2XYT+amp plates and incubated at 37° C. overnight. The resulting transformants were picked and subjected to DNA sequencing to confirm that the mdh3 gene was successfully integrated into the vector.

Example 12

Cloning of the *Aspergillus oryzae* NRRL 3488 and *Aspergillus oryzae* ATCC 56747 Pyruvate Carboxylase Genes Pyruvate carboxylase genes (pyc) were cloned from *Aspergillus oryzae* NRRL 3488 and *Aspergillus oryzae* ATCC 56747 genomic DNA by PCR amplification using primers homologous to the putative pyruvate carboxylase gene model number AO090023000801 found in the published *Aspergillus oryzae* ATCC 42149 genome sequence (Galagan et al., 2005, supra; DDBJ accession numbers AP007150-AP007177) (uniprot accession number Q2UGL1).

The *Aspergillus oryzae* pyc genes were amplified using primers 061929 and 061930 shown below. *Aspergillus oryzae* (NRRL 3488 and ATCC 56747) genomic DNA was isolated as described in Example 1.

```
Primer 061929:
                                       (SEQ ID NO: 24)
5'-ACACAACTGGCCATGGCGGCTCCGTTTCGTCA-3'

Primer 061930
                                       (SEQ ID NO: 25)
5'-AGTCACCTCTAGTTAATTAATTATTACGCTTTGACGATCTTG
CAG-3'
```

The amplification reactions were performed using an EXPAND® High Fidelity PCR System according to manufacturer's instructions. The amplification reactions were composed of 47 ng *Aspergillus oryzae* genomic DNA, 200 μM dNTPs, 50 μM forward primer, 50 pM reverse primer, 1× EXPAND® reaction buffer, and 2.6 units EXPAND® High Fidelity enzyme mix in a final volume of 50 μl. The amplification reactions were incubated in an EPPENDORF® MASTERCYCLER® programmed for 1 cycle at 94° C. for 2 minutes; 10 cycles each at 94° C. for 15 seconds, 60° C. for 30 seconds, and 72° C. for 1 minute; 15 cycles each at 94° C. for 15 seconds, 60° C. for 30 seconds, and 72° C. for 1 minute plus 0.5 second each successive cycle; and 1 cycle at 72° C. for 7 minutes.

PCR products from the amplification reactions were purified by 1% agarose gel electrophoresis in TAE buffer. Each 3.5 kb fragment was excised from the gels and agarose extracted using a QIAQUICK® Gel Extraction Kit.

Example 13

Characterization of the *Aspergillus oryzae* NRRL 3488 and ATCC 56747 Pyruvate Carboxylase Genes DNA sequencing of the *Aspergillus oryzae* NRRL 3488 and ATCC 56747 pyruvate carboxylase genes (pyc) was performed with an ABI3130XL DNA Analyzer using the primer walking technique with dye-terminator chemistry (Giesecke et al., 1992, supra).

The nucleotide sequence (SEQ ID NO: 26) and deduced amino acid sequence (SEQ ID NO: 27) of the *Aspergillus oryzae* pyruvate carboxylase genes are shown in FIGS. 9A and 9B. Both the *Aspergillus oryzae* NRRL 3488 and ATCC 56747 pyruvate carboxylase genes have the same nucleotide sequence. The genomic coding sequence of 3643 bp (including one stop codon) encodes a polypeptide of 1193 amino acids with a predicted mass of 131 kDa. The coding sequence is interrupted by 1 intron of 61 bp (3475-3535 bp). The G+C content of the coding region of the gene is 57.1%.

A comparative pairwise global alignment of amino acid sequences in public databases was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Aspergillus oryzae* NRRL 3488 or ATCC 56747 pyruvate carboxylase pyc gene shares 68.4% sequence identity to the deduced amino acid sequence of the *Saccharomyces cerevisiae* pyruvate carboxylase gene (PYC1; accession number YGI062W).

Example 14

Construction of Expression Vector pRyan1

Plasmid pRyan1 was constructed to contain the pyruvate carboxylase (pyc) gene sequence (DOGAN: AO090023000801), a 3646 bp fragment from *Aspergillus oryzae* (including two stop codons). This plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The pyc gene was amplified from *Aspergillus oryzae* NRRL 3488 genomic DNA using primers 066549 and 067388 shown below.

```
Primer 066549:
                                    (SEQ ID NO: 30)
5'-TAGAACATCGTCCATAATGGCGGCTCCGTTTCGTCA-3'

Primer 067388:
                                    (SEQ ID NO: 31)
5'-GTGTCAGTCACCTCTAGTTATTATTACGCTTTGACGATCT-3'
```

The PCR reaction was composed of 5 µl 10× reaction buffer, 1 µl *Aspergillus oryzae* NRRL3488 genomic DNA (110 ng/µl), 1 µl primer 066549 (100 ng/µl), 1 µl primer 067388 (100 ng/µl), 1 µl dNTP mixture (10 mM), 45.5 µl deionized water, and 0.5 µl Herculase® HotStart DNA polymerase. The amplification reaction was incubated in an EPPENDORF® MASTERCYCLER® programmed for 1 cycle at 95° C. for 2 minutes; 10 cycles each at 95° C. for 10 seconds, 58° C. for 30 seconds, and 72° C. for 3.5 minutes; 20 cycles each at 95° C. for 10 seconds, 58° C. for 30 seconds, and 72° C. for 3.5 minutes plus 10 seconds per cycle. The PCR product was then purified using a MinElute® PCR Purification Kit.

Figure 10:
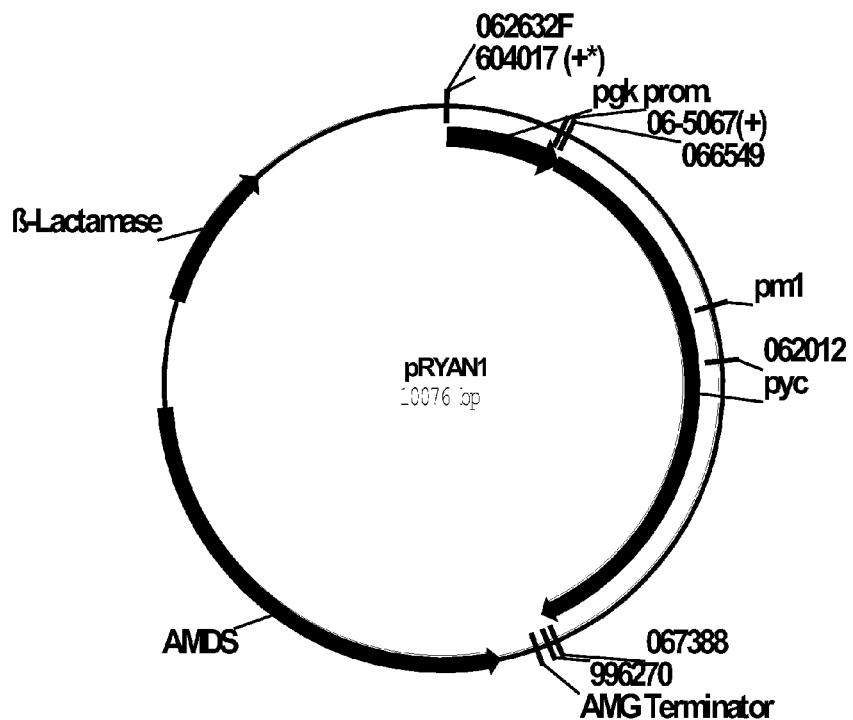
FIG. 10 shows a restriction map of pRYAN1.

The purified PCR product was inserted into the vector using an In-Fusion™ Advantage reaction composed of 2 µl 5× buffer, 1 µl purified PCR product (144 ng/µl), 2 µl gel purified Sex AI and Pac I restriction digested pShTh60 (FIG. 1; 78 ng/µl), 1 µl In-Fusion™ enzyme and 4 µl deionized water. The reaction was incubated at 37° C. for 15 minutes followed by 50° C. for 15 minutes after which it was placed on ice for 5 minutes and diluted with 40 µl TE buffer resulting in pRYAN1 (FIG. 10). A 2 µl aliquot of the ligation reaction was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the pyc gene was successfully integrated into the vector. Nucleotide 1308 was changed from C to T, but did not affect the protein sequence.

Example 15

Transformation of pShTh104, pSaMF21 and pRyan1 into *Aspergillus oryzae* NRRL 3488 (SaMF2103)

Plasmids pShTh104, pSaMF21 and pRyan1 were transformed into *Aspergillus oryzae* NRRL 3488 to assay C4 dicarboxylic acid production for strains containing the mae3 C4 dicarboxylic acid transporter, the mdh3 NBD-dependent malate dehydrogenase, and the pyc pyruvate carboxylase genes described above.

100 µl of protoplast preparation (prepared as described in Example 3) was transferred to a 12 ml polypropylene tube. To this was added 2.6 µg pSaMF21, 5.5 µg pShTh104, 4.73 µg pRyan1 and 250 µl PEG solution (60% w/v polyethylene glycol (PEG), 10 mM Tris 6.5, 10 mM CaCl) followed by gentle mixing and incubation at 37° C. for 30 minutes. Each transformation was diluted with 9 ml of STC buffer, followed by plating three separate 3 ml aliquots onto COVE plates. Each plate was then incubated at 34° C. for 7-10 days. Sixty SaMF2103 transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Extraction of DNA from the top five malic acid producing strains (SaMF2103-14, 29, 37, 39, 53) were performed by inoculating approximately $2\times10^7$ spores into 100 ml YEG medium and incubating the flask at 34° C. for 16-18 hours at 160 rpm. Mycelia were collected by pouring the culture through a sterile vacuum filtration unit. The biomass was incubated in liquid nitrogen for about 10 seconds, then placed onto 2 layers of cheesecloth lined with MIRACLOTH®. The cloth was folded into a pouch and smashed with a hammer 12-15 times. The crushed biomass was transferred to a sterile 50 ml conical tube, to which was added 10 ml of 1× Lysis Buffer (100 mM EDTA, 10 mM Tris pH 8.0, 1% Triton X-100, 0.5 M guanidine-HCl, 200 mM NaCl) and 3 µl 100 mg/ml RNase A. Following 5 minutes of incubation at room temperature, 150 µl 20 mg/ml Proteinase K (QIAGEN Inc., Valencia, Calif., USA) was added, mixed by inversion and incubated at 50° C. for 1 hour. The tubes were centrifuged for 20 minutes at 7240×g. The supernatant was poured into a Midi-Tip (QIAGEN Inc., Valencia, Calif., USA) pre-equilibrated with 4 ml QBT buffer and allowed to flow by gravity.

The tips were washed with 15 ml QC buffer (QIAGEN Inc., Valencia, Calif., USA) then eluted with 5 ml of QF buffer (QIAGEN Inc., Valencia, Calif., USA). To these 3.5 ml of isopropanol was added and mixed, then centrifuged for 20 minutes at 4° C. at 12,380×g. The supernatants were discarded and the pellets were washed with 2 ml cold 70% ethanol before being centrifuged for 10 minutes at 4° C. at 12,380×g. The pellets were air dried, then resuspended in 100 µl EB buffer (QIAGEN Inc., Valencia, Calif., USA). The DNA concentrations were 71 ng/µl SaMF2103-14, 220 ng/µl SaMF2103-29, 210 ng/µl SaMF2103-37, 230 ng/µl SaMF2103-39, 233 ng/µl SaMF2103-53.

```
Primer 062012:
5'-GGAAACGTCAAGCGGCTTGC-3'   (SEQ ID NO: 32)
```

PCR reactions to test for the presence of the pShTh104 expression cassette were composed of 2.5 µl 10× reaction buffer, 1 µl template (80-300 ng/µl), 0.5 µl primer 065067 (Example 1; 50 pM), 0.5 µl primer 065130 (Example 1; 50 pM), 0.5 µl dNTP mixture (10 mM), 19.75 µl deionized water, and 0.25 µl Herculase® HotStart DNA polymerase. PCR reactions to test for the presence of the pSaMF21 expression cassette were composed of 2.5 µl 10× reaction buffer, 1 µl template (80-300 ng/µl), 0.5 µl primer 065067 (Example 1; 50 pM), 0.5 µl primer 062400 (Example 8; 50 pM), 0.5 µl dNTP mixture (10 mM), 19.75 µl deionized water, and 0.25 µl of Herculase® HotStart DNA polymerase. PCR reactions to test for the presence of the pRyan1 expression cassettes were composed of 2.5 µl 10× reaction buffer, 1 µl template (80-300 ng/µl), 0.5 µl primer 065067 (Example 1; 50 pM), 0.5 µl primer 062012 (see above; 50 µM), 0.5 µl dNTP mixture (10 mM), 19.75 µl deionized water, and 0.25 µl Herculase® HotStart DNA polymerase. *Aspergillus oryzae* NRRL 3488 genomic DNA (110 ng/µl) was used as a negative control template for all three expression cassettes and the plasmids (diluted to 20 ng/µl) were used as positive control templates. The amplification reactions were incubated in an EPPENDORF® MASTERCYCLER® programmed for 1 cycle at 95° C. for 2 minutes; 10 cycles each at 95° C. for 10 seconds, 55° C. for 30 seconds, and 72° C. for 1.5 minutes; 20 cycles each at 95° C. for 10 seconds, 50° C. for 30 seconds, and 72° C. for 1.5 minute plus 10 seconds per cycle. The PCR products (5 µl) from each sample (in this order pShTh104, pSaMF21, pRyan1) were analyzed by 0.8% agarose gel electrophoresis. The five samples tested (and positive controls) had expected band sizes while the *Aspergillus oryzae* NRRL 3488 control samples did not.

Example 16

Production of Malic Acid in Shake Flask Cultures

Spores from each transformant described in Example 15 and *Aspergillus oryzae* NRRL 3488 as a control were plated onto individual PDA plates and allowed to sporulate at 34° C. for 5 to 7 days. Spores were collected in 0.05% TWEEN® 80. Seed cultures were prepared in 250 ml flasks containing 100 ml of seed medium B and inoculated with 300 µl spore stock. Seed cultures were grown for approximately 22 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 3 days.

*Aspergillus oryzae* SaMF2103 transformants which contain the heterologous mae3 C4 dicarboxylic acid transporter gene, the heterologous mdh3 NBD-dependent malate dehydrogenase gene, and the heterologous pyc pyruvate carboxylase gene (Example 15), produced malic acid increases in titer of up to 2.6-fold compared to *Aspergillus oryzae* NRRL 3488 control.

Example 17

Fermentation of *Aspergillus oryzae* ShTh1040 and SaMF2103 Strains

*Aspergillus oryzae* strains ShTh1040-31 and ShTh1040-44 (each containing the mae3 C4 dicarboxylic acid transporter gene; Example 3), and SaMF2103-37 and SaMF2103-39 (each containing the mae3 C4 dicarboxylic acid transporter gene, the mdh3 NBD-dependent malate dehydrogenase gene, and the pyc pyruvate carboxylase gene; Example 15) were grown for approximately 7 days at 34° C. on PDA plates. A 5-6 ml volume of sterile 50 mM sodium phosphate pH 6.8 buffer containing 0.2% TWEEN® 80 was added to each of the plates and spores were suspended by scraping with an inoculating loop. Each of the suspended spores was transferred from the plate by pipette to a 50 ml conical tube. For each tube, 25 ml of the sterile 50 mM sodium phosphate pH 6.8 buffer containing 0.2% TWEEN® 80 was added to a 500 ml unbaffled flask containing 75 ml of seed medium, which was then inoculated with 2 ml of spore suspension. The seed medium was composed of 40 g glucose, 6 g Bacto peptone, 0.75 g $KH_2PO_4$, 0.75 g $K_2HPO_4$, 0.1 g $MgSO_4.7H_2O$, 0.1 g $CaCl_2.2H_2O$, 0.005 g $FeSO_4.7H_2O$, 0.005 g NaCl, and deionized water to 1 liter. The flasks were then incubated at 34° C. and 180 rpm for approximately 24 hours. Three seed flasks were combined to supply 144 ml inoculum per tank. Three-liter fermentors containing 1.8 liters of medium were individually inoculated with the strain of choice by introducing 144 ml (8%) of the seed culture broth from three combined seed flasks of either *Aspergillus oryzae* transformant ShTh1040-31, *Aspergillus oryzae* transformant ShTh1040-44, *Aspergillus oryzae* transformant SaMF2103-37 or *Aspergillus oryzae* transformant SaMF2103-39. The medium was composed of 120 g glucose, 120 g $CaCO_3$, 9 g Bacto peptone, 0.150 g $KH_2PO_4$, 0.150 g $K_2HPO_4$, 0.10 g $MgSO.7H_2O$, 0.10 g $CaCl_2.2H_2O$, 0.005 g $FeSO_4.7H_2O$, 0.005 g NaCl, 1.22 mg biotin, and deionized water to 1 liter.

The fermentors were equilibrated at 34±0.1° C. and stirred at 500 rpm. Inlet air flow was maintained at 1 v/v/m. No acid or base additions were used for pH control. Feeds consisting of 20% glucose were administered to each tank at rate of approximately 7.3 g/hr beginning at about 43 hours into the fermentations. An additional 100 g of $CaCO_3$ was introduced to each tank on day 5 of the fermentations. Samples were withdrawn daily and analyzed for malic acid production. Fermentations were completed after 8 days.

Example 18

HPLC Quantitation of Malic Acid of Fermentations

Quantitation of malic acid for the fermentations of Example 17 was performed as described in Example 5.

Table 3 shows the relative malic acid titer of *Aspergillus oryzae* transformants ShTh1040-44, SaMF2103-37, SaMF2103-39, and ShTh1040-31. The relative ranking of each type of transformant is consistent with the shake flask results. Both SaMF2103 transformants which contain the heterologous mae3 C4 dicarboxylic acid transporter gene, the heterologous mdh3 NBD-dependent malate dehydrogenase gene, and the heterologous pyc pyruvate carboxylase gene (Example 15) yielded higher malic acid titers than either ShTh1040 transformant which contain the heterologous mae3 C4 dicarboxylic acid transporter gene, but not the heterologous mdh3 NBD-dependent malate dehydrogenase gene or the heterologous pyc pyruvate carboxylase gene (Example 3).

TABLE 3

| Transformant | Relative Malic Acid Titer |
|---|---|
| ShTh1040-31 | 1.00 |
| ShTh1040-44 | 1.21 |
| SaMF2103-37 | 1.40 |
| SaMF2103-39 | 1.50 |

Example 19

Figure 11:
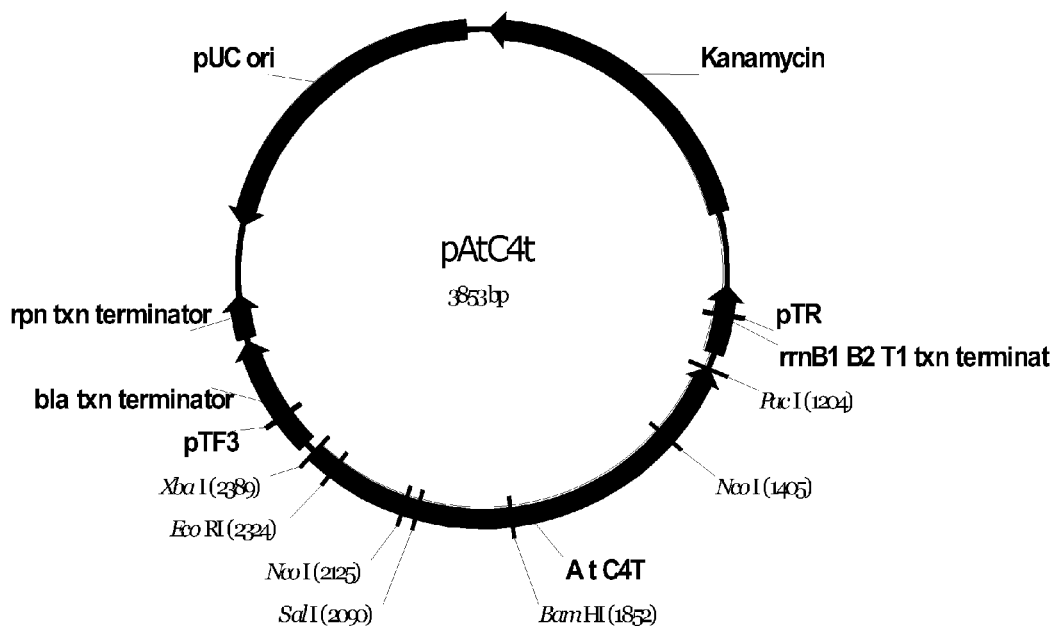
FIG. 11 shows a restriction map of pAtC4T.

Cloning of a *Aspergillus terreus* C4 Dicarboxylic Acid Transporter Gene and Construction of Expression Vector pShTh122AtC4T The 1182 bp *Aspergillus terreus* C4 dicarboxylic acid transport protein gene atc4t (ATEG_00085) was synthetically constructed into pAtC4T (FIG. 11; DNA2.0, Menlo Park, Calif., USA). The atc4t gene was amplified from pAtC4T using primers 069739 and 069740 shown below.

```
Primer 069739:
                                    (SEQ ID NO: 38)
5'-GTGTGATAGAACATCGTCCATAATGTTTGAGAACACTGCCCC-3'

Primer 069740:
                                    (SEQ ID NO: 39)
5'-GTCAGTCACCTCTAGTTAATTAATTACTCCACCACATCCTCGTC-3'
```

The PCR reaction mixture was composed of 50 ng of pAtC4T template, 200 μM dNTP mixture, 50 pM of primer 069739, 50 pM primer 069740, 1×Pol1 reaction buffer (New England Biolabs, MA, USA), 3% DMSO, 1 unit of Vent DNA Polymerase (New England Biolabs), and deionized water 50 μl. The PCR reaction was incubated in an EPPENDORF MASTERCYCLER® programmed for 1 cycle at 94° C. for 3 minutes; 35 cycles each at 94° C. for 15 seconds, 59° C. for 30 seconds, and 72° C. for 1 minute; and 1 cycle at 72° C. for 5 minutes. The PCR product was purified by 1% agarose gel electrophoresis in TAE buffer and purified using a QIAQUICK® Gel Extraction Kit.

Figure 12:
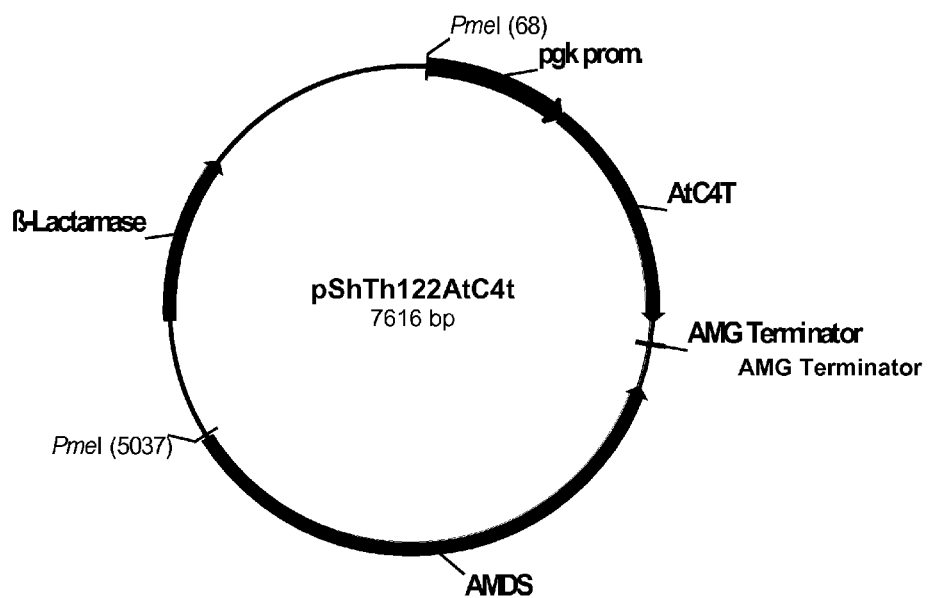
FIG. 12 shows a restriction map of pShTh122AtC4t.

Plasmid pShTh60 (FIG. 1) was digested with Sex AI and Pac I then separated by 0.8% agarose gel electrophoresis in TBE buffer (10.8 g/L Tris Base, 5.5 g/L boric acid, 2 mM EDTA, pH 8.0) and purified using a QIAQUICK® Gel Extraction Kit. The purified PCR product above was then inserted into the digested vector using an InFusion™ Cloning Kit according to the manufacturer's instructions resulting in plasmid pShTh122AtC4T (FIG. 12). Plasmid pShTh122AtC4T was isolated using a QIAfilter Maxi Plasmid Isolation Kit. DNA sequence analysis was used to confirm the integrity of the atc4t coding sequence using primers 996270 and 065067 described in the Examples above.

The nucleotide sequence (SEQ ID NO: 33) and deduced amino acid sequence (SEQ ID NO: 34) of the atc4t gene are shown in FIG. 13. The genomic coding sequence of 1182 bp (including stop codon) encodes a polypeptide of 393 amino acids with a predicted mass of 43.2 kDa and an isoelectric pH of 6.54. The gene contains no introns.

Example 20

Transformation of pShTh12AtC4T into *Aspergillus oryzae* NRRL3488

The pShTh12AtC4T vector in Example 19 was prepared for transformation by restriction digestion with Pme I. The approximately 5 kb expression cassette was separated from the vector sequences by 0.8% agarose gel electrophoresis in TBE buffer and purified using a QIAQUICK® Gel Extraction Kit.

Four transformation reactions were prepared. For each reaction, a 100 μl solution of protoplast preparation (prepared as described in Example 3) was transferred to a 12 ml polypropylene tube, to which was added 2-5 μg of digested plasmid vector above and 250 μl of polyethylene glycol solution (60% w/v polyethylene glycol (PEG), 10 mM Tris 6.5, 10 mM CaCl), followed by gentle mixing and incubation at 37° C. for 30 minutes. Each transformation reaction was diluted with 6 ml STC, followed by three separate aliquots onto COVE plates. Each plate was then incubated at 34° C. for 7-10 days. The resulting transformants were transferred to individual COVE plates and incubated at 34° C. for 5 days. Spore stocks were prepared by collecting the spores in 0.1% TWEEN® 80. Cultures were stored by preparing a glycerol stock of each (800 μl spore stock, 200 μl 0.1% TWEEN® 80) and frozen at −80° C.

Example 21

Production of Malic Acid in Shake Flask Cultures

Spores from each transformant described in Example 20 (ShTh1220) and *Aspergillus oryzae* NRRL 3488 as a control were plated onto individual PDA plates and allowed to sporulate at 34° C. for 5 to 7 days. Spores were collected in 0.05% TWEEN® 80. Seed cultures were prepared in 250 ml flasks containing 100 ml of seed medium B and inoculated with 300 μl spore stock. Seed cultures were grown for approximately 22 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 3 days.

*Aspergillus oryzae* ShTh1220 transformants, which contain the heterologous *Aspergillus terreus* C4 dicarboxylic acid transport protein gene atc4t, produced malic acid increases in titer of up to 1.9-fold compared to *Aspergillus oryzae* NRRL 3488 control.

Example 22

Fermentation of *Aspergillus oryzae* ShTh1220 Strains

*Aspergillus oryzae* ShTh1220-11, ShTh1220-22 and ShTh1220-25 were grown for approximately 7 days at 34° C. on PDA plates. A 5-6 ml volume of sterile 50 mM sodium phosphate pH 6.8 buffer containing 0.2% TWEEN® 80 was added to each of the plates and spores were suspended by scraping with an inoculating loop. Each of the suspended spores was transferred from the plate by pipette to a 50 ml conical tube. For each tube, 25 ml of the sterile 50 mM sodium phosphate pH 6.8 buffer containing 0.2% TWEEN® 80 was added to a 500 ml unbaffled flask containing 75 ml of seed medium, which was then inoculated with 2 ml of spore suspension. The seed medium was composed of 40 g glucose, 6 g Bacto-peptone, 0.75 g $KH_2PO_4$, 0.75 g $K_2HPO_4$, 0.1 g $MgSO_4.7H_2O$, 0.1 g $CaCl_2.2H_2O$, 0.005 g $FeSO_4.7H_2O$, 0.005 g NaCl, and deionized water to 1 liter. The flasks were then incubated at 34° C. and 180 rpm for approximately 24 hours. Three seed flasks were combined to supply 144 ml inoculum per tank. Three-liter fermentors containing 1.8 liters of medium were individually inoculated with the strain of choice by introducing 144 ml (8%) of the seed culture broth from three combined seed flasks of either *Aspergillus oryzae* transformant ShTh1220-11, *Aspergillus oryzae* transformant ShTh1220-22 or *Aspergillus oryzae* transformant ShTh1220-25. The medium was composed of 60 g glucose, 120 g $CaCO_3$, 9 g Bacto-peptone, 0.150 g $KH_2PO_4$, 0.150 g $K_2HPO_4$, 0.10 g $MgSO.7H_2O$, 0.10 g $CaCl_2.2H_2O$, 0.005 g $FeSO_4.7H_2O$, 0.005 g NaCl, 1.22 mg biotin, and deionized water to 1 liter.

The fermentors were equilibrated at 34±0.1° C. and stirred at 500 rpm. Inlet air flow was maintained at 1 v/v/m. No acid or base additions were used for pH control. Feeds consisting of 25% glucose were administered to each tank at the rate of approximately 7.3 g/hr beginning at about 43 hours into the fermentations. After about 92 hours of fermentation the feed rates were increased to approximately 9.3 g/hr, and then returned to approximately 7.3 g/hr at about 164 hours. An additional 100 g of $CaCO_3$ was introduced to each tank on day 5 of the fermentations. Samples were withdrawn daily and analyzed for malic acid production. Fermentations were completed after 8 days.

Example 23

HPLC Quantitation of Malic Acid of Fermentations

Quantitation of malic acid for the fermentations of Example 22 was performed as described in Example 5.

Table 4 shows the relative malic acid titer of *Aspergillus oryzae* transformants ShTh1220-11, ShTh1220-22, and ShTh1220-25 compared to the malic acid production of ShTh1040-22. The relative ranking of each transformant is consistent with the shake flask results by demonstrating that ShTh1220 transformants (which contain the heterologous *Aspergillus terreus* C4 dicarboxylic acid transport protein gene atc4t) yielded similar malic acid titer to the ShTh1040 transformant (which contains the heterologous mae3 C4 dicarboxylic acid transporter gene and is shown in Example 7 to have increased titer over the *Aspergillus oryzae* NRRL 3488 control lacking a heterologous C4 dicarboxylic acid transporter).

TABLE 4

| Transformant | Relative Malic Acid Titer |
|---|---|
| ShTh1040-22 | 1.00 |
| ShTh1220-11 | 0.97 |
| ShTh1220-22 | 0.96 |
| ShTh1220-25 | 0.96 |

Example 24

Cloning of a *Schizosaccharomyces pombe* C4 Dicarboxylic Acid Transporter Gene and Construction of Expression Vector pSaMF27

Figure 14:
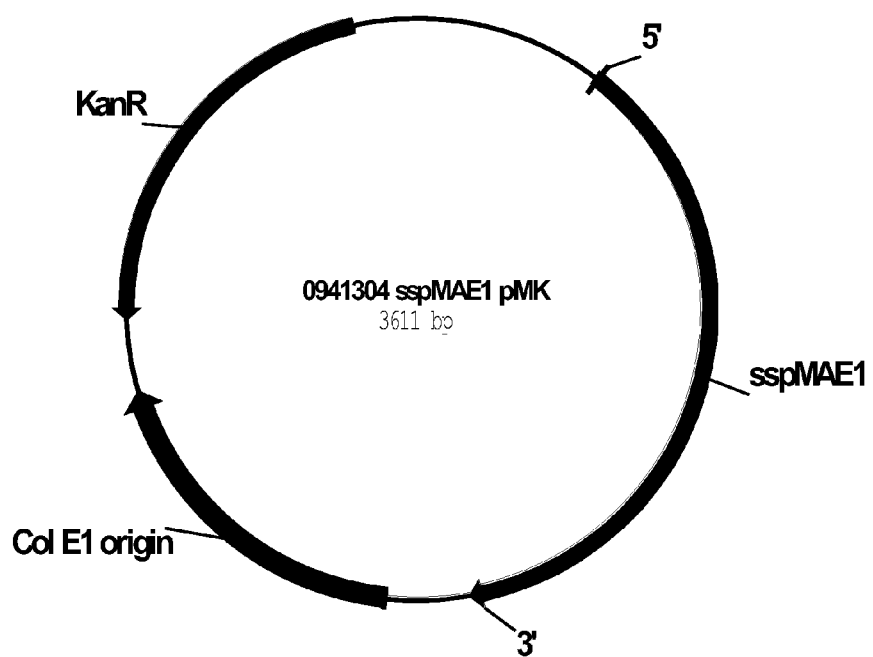
FIG. 14 shows a restriction map of p0941304 sspMAE1_pMK.

The putative *Schizosaccharomyces pombe* C4 dicarboxylic acid transport protein gene mae1 (GenBank: U21002.1) was codon optimized for expression in *Aspergillus oryzae* and synthetically constructed into p0941304_sspMAE1_pMK (FIG. 14; GENEART, Burlingame, Calif., USA). The mae1 gene was amplified from p0941304_sspMAE1_pMK using primers 068320 and 068808 shown below.

Primer 068320:
(SEQ ID NO: 40)
5'-GAACATCGTCCATAATGGGAGAATTGAAGGAAATTC-3'

Primer 068808:
(SEQ ID NO: 41)
5'-GGTGTCAGTCACCTCTAGTTATTATTAGACCGACTCGTGT-3'

The PCR reaction was composed of 5 µl 10× reaction buffer, 1 µl 0941304_sspMAE1_pMK template (50 ng/µl), 1 µl primer 068320 (100 ng/µl), 1 µl primer 068808 (100 ng/µl), 1 µl dNTP mixture (10 mM), 45.5 µl deionized water, and 0.5 µl Herculase® HotStart DNA polymerase. The amplification reaction was incubated in an EPPENDORF® MASTERCYCLER® programmed for 1 cycle at 95° C. for 2 minutes; 10 cycles each at 95° C. for 10 seconds, 55° C. for 30 seconds, and 72° C. for 1.5 minutes; 20 cycles each at 95° C. for 10 seconds, 55° C. for 30 seconds, and 72° C. for 1.5 minutes plus 10 seconds per cycle. The PCR reaction was subjected to restriction digestion with Dpn I for 1 hour to degrade any plasmid DNA template then purified using the Qiagen MinElute® PCR purification kit.

Figure 15:
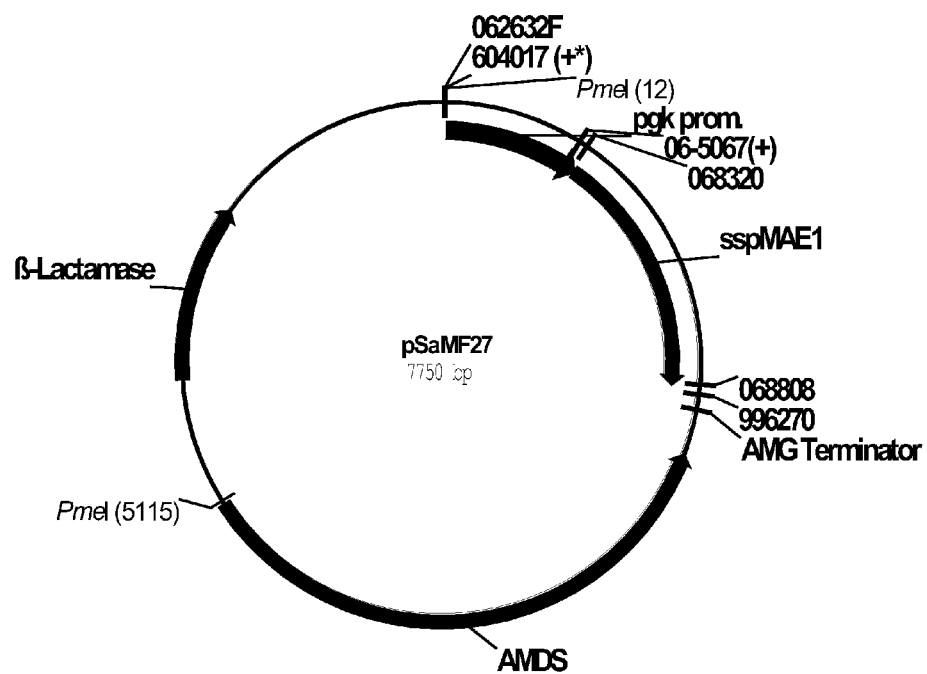
FIG. 15 shows a restriction map of pSaMF27.

Plasmid pShTh60 (FIG. 1) was digested with Sex AI and Pac I then separated by 0.8% agarose gel electrophoresis in TBE buffer and purified using a QIAQUICK® Gel Extraction Kit. The purified PCR product above was then inserted into the digested vector using an In-Fusion Advantage™ Reaction Kit in a reaction composed of 2 µl 5× buffer, 0.5 µl purified PCR product (148 ng/µl), 2.5 µl digested and gel purified pShTh60 (78 ng/µl), 1 µl InFusion™ enzyme and 4 µl deionized water. The reaction was incubated at 37° C. for 15 minutes then 50° C. for 15 minutes after which it was placed on ice for 5 minutes and diluted with 40 µl TE buffer resulting in pSaMF27 (FIG. 15).

A 2 µl aliquot of the ligation reaction above was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing using primers 065067 and 996270 (see Examples above) to confirm that the mae1 gene was successfully integrated into the vector.

The codon-optimized nucleotide sequence (CO), deduced amino acid sequence, and wild-type nucleotide sequence (WT) of the *Schizosaccharomyces pombe* mae1 gene are shown in FIGS. 16A and 16B (SEQ ID NO: 35, SEQ ID NO: 36, and SEQ ID NO:37, respectively). The coding sequence is 1317 bp including the stop codon. The encoded predicted protein is 439 amino acids with a predicted mass of 49.4 kDa and an isoelectric pH of 8.24. The gene contains no introns. Using the SignalP program (Nielsen et al., 1997, Protein Engineering 10:1-6), a signal peptide of 49 residues was predicted. Based on this program, the predicted mature protein contains 389 amino acids with a predicted molecular mass of 43.7 kDa and an isoelectric pH of 7.67.

Example 25

Transformation of pSaMF27 into *Aspergillus oryzae* NRRL3488

The pSaMF27 vector in Example 24 was prepared for transformation by restriction digestion with Pme I for 1 hour at 37° C. The 5103 bp expression cassette was purified by 0.8% agarose gel electrophoresis in TBE buffer and a QIAQUICK® Gel Extraction Kit according to manufacturer's instructions.

Three transformation reactions were prepared. For each reaction, 100 µl of protoplast preparation (prepared as described in Example 3) was transferred to a 12 ml polypropylene tube. To this was added 5 µg of ampicillin marker-free, linearized pSaMF27 vector and 250 µl of polyethylene glycol (PEG) followed by gentle mixing and incubation at 37° C. for 30 minutes. Each transformation was diluted with 3 ml of STC buffer followed by plating onto COVE plates. Each plate was then incubated at 34° C. for 7-10 days. The resulting transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 26

Production of Malic Acid in Shake Flask Cultures

Spores from each transformant described in Example 25 and *Aspergillus oryzae* NRRL 3488 as a control were plated onto individual PDA plates and allowed to sporulate at 34° C. for 5 to 7 days. Spores were collected in 0.05% TWEEN® 80. Seed cultures were prepared in 250 ml flasks containing 100 ml of seed medium B and inoculated with 300 µl spore stock. Seed cultures were grown for approximately 22 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 3 days.

*Aspergillus oryzae* SaMF27 transformants, which contain the heterologous *S. pombe* C4 dicarboxylic acid transport protein gene mae1, produced malic acid increases in titer of up to 1.9-fold compared to *Aspergillus oryzae* NRRL 3488 control.

Example 27

Fermentation of *Aspergillus oryzae* SaMF27 strains

*Aspergillus oryzae* ShTh1040-44, SaMF27-2, SaMF27-4 and SaMF27-7 were grown for approximately 7 days at 34° C. on PDA plates. A 5-6 ml volume of sterile 50 mM sodium phosphate pH 6.8 buffer containing 0.2% TWEEN® 80 were added to each of the plates and spores were suspended by scraping with an inoculating loop. Each of the suspended spores was transferred from the plate by pipette to a 50 ml conical tube. For each tube, 25 ml of the sterile 50 mM sodium phosphate pH 6.8 buffer containing 0.2% TWEEN® 80 was added to a 500 ml unbaffled flask containing 75 ml of seed medium, which was then inoculated with 2 ml of spore suspension. The seed medium was composed of 40 g glucose, 6 g Bacto peptone, 0.75 g $KH_2PO_4$, 0.75 g $K_2HPO_4$, 0.1 g $MgSO_4.7H_2O$. 0.1 g $CaCl_2.2H_2O$, 0.005 g $FeSO_4.7H_2O$, 0.005 g NaCl, and deionized water to 1 liter. The flasks were then incubated at 34° C. and 180 rpm for approximately 24 hours. Three seed flasks were combined to supply 144 ml inoculum per tank. Three-liter fermentors containing 1.8 liters of medium were individually inoculated with the strain of choice by introducing 144 ml (8%) of the seed culture broth from three combined seed flasks of either *Aspergillus oryzae* transformant ShTh1040-44, *Aspergillus oryzae* transformant SaMF27-2, *Aspergillus oryzae* transformant SaMF27-4 or *Aspergillus oryzae* transformant SaMF27-7. The medium was composed of 120 g glucose, 120 g $CaCO_3$, 9 g Bacto peptone, 0.150 g $KH_2PO_4$, 0.150 g $K_2HPO_4$, 0.10 g $MgSO.7H_2O$, 0.10 g $CaCl_2.2H_2O$, 0.005 g $FeSO_4.7H_2O$, 0.005 g NaCl, 1.22 mg biotin, and deionized water to 1 liter.

The fermentors were equilibrated at 34±0.1° C. and stirred at 500 rpm. Inlet air flow was maintained at 1 v/v/m. No acid or base additions were used for pH control. Feeds consisting of 20% glucose were administered to each tank at rate of approximately 7.3 g/hr beginning at about 43 hours into the fermentations. An additional 100 g of $CaCO_3$ was introduced to each tank on day 5 of the fermentations. Samples were withdrawn daily and analyzed for malic acid production. Fermentations were completed after 8 days.

Example 28

HPLC Quantitation of Malic Acid of Fermentations

Quantitation of malic acid for the fermentations of Example 27 was performed as described in Example 5.

Table 5 shows the relative malic acid titer of *Aspergillus oryzae* transformants SaMF27-2, SaMF27-4, and SaMF27-7 compared to the malic acid production of ShTh1040-44. The relative ranking of each transformant is consistent with the shake flask results by demonstrating that SaMF27 transformants (which contain the heterologous *S. pombe* C4 dicarboxylic acid transport protein gene mae1) gave similar malic acid yields to the ShTh1040 transformant (which contains the heterologous mae3 C4 dicarboxylic acid transporter gene and is shown in Example 7 to have increased titer over the *Aspergillus oryzae* NRRL 3488 control lacking a heterologous C4 dicarboxylic acid transporter).

TABLE 5

| Transformant | Relative Malic Acid Titer |
|---|---|
| ShTh1040-44 | 1.00 |
| SaMF27-2 | 0.89 |
| SaMF27-4 | 0.95 |
| SaMF27-7 | 0.84 |

The present invention may be further described by the following numbered paragraphs:

[1] A method of producing a C4 dicarboxylic acid (e.g., malic acid), comprising: (a) cultivating in a medium a filamentous fungal host cell comprising one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase; wherein the filamentous fungal host cell secretes (or is capable of secreting) increased levels of the C4 dicarboxylic acid compared to the filamentous fungal host cell without the one or more (several) heterologous polynucleotides encoding the C4 dicarboxylic acid transporter, the malate dehydrogenase, and the pyruvate carboxylase when cultivated under the same conditions; and (b) recovering the C4 dicarboxylic acid.

[2] The method of paragraph [1], wherein the C4 dicarboxylic acid transporter is selected from the group consisting of (a) a C4 dicarboxylic acid transporter comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 8, SEQ ID NO: 34, or SEQ ID NO: 36; (b) a C4 dicarboxylic acid transporter encoded by a polynucleotide that hybridizes under at least low stringency conditions, e.g., medium stringency conditions, medium-high stringency conditions, high stringency conditions, or very high stringency conditions with SEQ ID NO: 7, SEQ ID NO: 33, SEQ ID NO: 35, or SEQ ID NO: 37; or a full-length complementary strand thereof; (c) a C4 dicarboxylic acid transporter encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 7, SEQ ID NO: 33, SEQ ID NO: 35, or SEQ ID NO: 37; (d) a C4 dicarboxylic acid transporter variant comprising a substitution, deletion, and/or insertion of one or more (several) amino acids of the mature polypeptide of SEQ ID NO: 8, SEQ ID NO: 34, or SEQ ID NO: 36; and (e) a fragment of the C4 dicarboxylic acid transporter of (a), (b), (c), or (d) that has C4 dicarboxylic acid transporter activity.

[3] The method of paragraph 1 or 2, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 8.

[4] The method of any one of paragraphs 1-3, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 34.

[5] The method of any one of paragraphs 1-4, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 36.

[6] The method of any one of paragraphs 1-5, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 7 or the full-length complementary strand thereof.

[7] The method of any one of paragraphs 1-6, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 33 or the full-length complementary strand thereof.

[8] The method of any one of paragraphs 1-7, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 35 or SEQ ID NO: 37; or a full-length complementary strand thereof.

[9] The method of any one of paragraphs 1-8, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 7.

[10] The method of any one of paragraphs 1-9, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 33.

[11] The method of any one of paragraphs 1-10, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 35 or SEQ ID NO: 37.

[12] The method of any one of paragraphs 1-11, wherein the C4 dicarboxylic acid transporter comprises or consists of SEQ ID NO: 8.

[13] The method of any one of paragraphs 1-11, wherein the C4 dicarboxylic acid transporter comprises or consists of SEQ ID NO: 34.

[14] The method of any one of paragraphs 1-11, wherein the C4 dicarboxylic acid transporter comprises or consists of SEQ ID NO: 36.

[15] The method of any of paragraphs 1-14, wherein the heterologous first polynucleotide encoding the C4 dicarboxylic acid transporter is operably linked to a promoter foreign to the first polynucleotide.

[16] The method of any of paragraphs 1-15, wherein the malate dehydrogenase is selected from the group consisting of (a) a malate dehydrogenase comprising an amino acid sequence having at least 60% sequence identity, e.g., at least 65%, at least 70%, at least 75%, at least 80%, at least 85%, at least 90%, at least 95%, or 100% sequence identity with SEQ ID NO: 18 or SEQ ID NO: 20; (b) a malate dehydrogenase encoded by a polynucleotide that hybridizes under at least low stringency conditions, e.g., medium stringency conditions, medium-high stringency conditions, high stringency conditions, or very high stringency conditions with (i) SEQ ID NO: 17 or SEQ ID NO: 19, (ii) the cDNA sequence contained in SEQ ID NO: 17 or SEQ ID NO: 19, or (iii) a full-length complementary strand of (i) or (ii); (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 17 or SEQ ID NO: 19; (d) a malate dehydrogenase variant comprising a substitution, deletion, and/or insertion of one or more (several) amino acids of the mature polypeptide of SEQ ID NO: 18 or SEQ ID NO: 20; and (e) a fragment of the malate dehydrogenase of (a), (b), (c), or (d) that has malate dehydrogenase activity.

[17] The method of any of paragraphs 1-16, wherein the malate dehydrogenase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 18.

[18] The method of any of paragraphs 1-17, wherein the malate dehydrogenase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 20.

[19] The method of any of paragraphs 1-18, wherein the malate dehydrogenase is encoded by a polynucleotide that hybridizes under low stringency conditions, medium stringency conditions, medium-high stringency conditions, or high stringency conditions with (i) SEQ ID NO: 17, (ii) the cDNA sequence contained in SEQ ID NO: 17, or (iii) the full-length complementary strand of (i) or (ii).

[20] The method of any of paragraphs 1-19, wherein the malate dehydrogenase is encoded by a polynucleotide that hybridizes under low stringency conditions, medium stringency conditions, medium-high stringency conditions, or high stringency conditions with (i) SEQ ID NO: 19, (ii) the cDNA sequence contained in SEQ ID NO: 19, or (iii) the full-length complementary strand of (i) or (ii).

[21] The method of any of paragraphs 1-20, wherein the malate dehydrogenase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 17.

[22] The method of any of paragraphs 1-21, wherein the malate dehydrogenase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 19.

[23] The method of any of paragraphs 1-22, wherein the malate dehydrogenase comprises or consists of SEQ ID NO: 18.

[24] The method of any of paragraphs 1-22, wherein the malate dehydrogenase comprises or consists of SEQ ID NO: 20.

[25] The method of any of paragraphs 1-15, wherein the malate dehydrogenase is a variant of a parent malate dehydrogenase comprising (i) a deletion at positions equivalent to or corresponding to amino acids positions 2 to 17 or a portion thereof of SEQ ID NO: 18, and (ii) a substitution at a position equivalent to amino acid 48 of SEQ ID NO: 18; wherein the deletion and the substitution reduce mitochondrial import in vivo of the malate dehydrogenase variant thereby increasing the level of the malate dehydrogenase variant in the cytosol, and wherein the filamentous fungal host cell secretes (or is capable of secreting) increased levels of the C4 dicarboxylic acid (e.g., malic acid) compared to the filamentous fungal host cell without the polynucleotide encoding the malate dehydrogenase variant when cultivated under the same conditions.

[26] The method of paragraph 25, wherein the parent malate dehydrogenase is selected from the group consisting of (a) a malate dehydrogenase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 18; (b) a malate dehydrogenase encoded by a polynucleotide that hybridizes under at least low stringency conditions, e.g., medium stringency conditions, medium-high stringency conditions, high stringency conditions, or very high stringency conditions with SEQ ID NO: 17, or its full-length complementary strand; and (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 17.

[27] The method of paragraph 26, wherein the parent malate dehydrogenase comprises or consists of SEQ ID NO: 18.

[28] The method of any of paragraphs 25-27, wherein the malate dehydrogenase variant comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to the amino acid sequence of SEQ ID NO: 18.

[29] The method of any of paragraphs 25-28, wherein the variant comprises the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18.

[30] The method of any of paragraphs 1-29, wherein the heterologous second polynucleotide encoding the malate dehydrogenase is operably linked to a promoter foreign to the second polynucleotide.

[31] The method of any of paragraphs 1-30, wherein the pyruvate carboxylase is selected from the group consisting of (a) a pyruvate carboxylase comprising an amino acid sequence having at least 60% sequence identity, e.g., at least 65%, at least 70%, at least at least 98%, at least 99%, or 100% with SEQ ID NO: 27; (b) a pyruvate carboxylase encoded by a polynucleotide that hybridizes under at least low stringency conditions, e.g., medium stringency conditions, medium-high stringency conditions, high stringency conditions, or very high stringency conditions with (i) SEQ ID NO: 26, (ii) the cDNA sequence contained in SEQ ID NO: 26, or (iii) the full-length complementary strand of (i) or (ii); (c) a pyruvate carboxylase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 26; (d) a pyruvate carboxylase variant comprising a substitution, deletion, and/or insertion of one or more (several) amino acids of the mature polypeptide of SEQ ID NO: 26; and (e) a fragment of the pyruvate carboxylase of (a), (b), (c), or (d) that has pyruvate carboxylase activity.

[32] The method of any of paragraphs 1-31, wherein the pyruvate carboxylase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% with SEQ ID NO: 27.

[33] The method of any of paragraphs 1-32, wherein the pyruvate carboxylase is encoded by a polynucleotide that hybridizes under low stringency conditions, medium stringency conditions, medium-high stringency conditions, or high stringency conditions with (i) SEQ ID NO: 26, (ii) the cDNA sequence contained in SEQ ID NO: 26, or (iii) the full-length complementary strand of (i) or (ii).

[34] The method of any of paragraphs 1-33, wherein the pyruvate carboxylase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 26.

[35] The method of any of paragraphs 1-34, wherein the pyruvate carboxylase comprises or consists of SEQ ID NO: 27.

[36] The method of any of paragraphs 1-35, wherein the pyruvate carboxylase is a variant of a mitochondrial pyruvate carboxylase.

[37] The method of any of paragraphs 1-36, wherein the heterologous third polynucleotide encoding the pyruvate carboxylase is operably linked to a promoter foreign to the third polynucleotide.

[38] The method of any of paragraphs 1-37, wherein the filamentous fungal host cell comprises a heterologous first polynucleotide encoding a C4 dicarboxylic acid transporter.

[39] The method of any of paragraphs 1-37, wherein the filamentous fungal host cell comprises a heterologous second polynucleotide encoding a malate dehydrogenase.

[40] The method of any of paragraphs 1-37, wherein the filamentous fungal host cell comprises a heterologous third polynucleotide encoding a pyruvate carboxylase.

[41] The method of any of paragraphs 1-37, wherein the filamentous fungal host cell comprises a heterologous first polynucleotide encoding a C4 dicarboxylic acid transporter and a heterologous second polynucleotide encoding a malate dehydrogenase.

[42] The method of any of paragraphs 1-37, wherein the filamentous fungal host cell comprises a heterologous first polynucleotide encoding a C4 dicarboxylic acid transporter and a heterologous third polynucleotide encoding a pyruvate carboxylase.

[43] The method of any of paragraphs 1-37, wherein the filamentous fungal host cell comprises a heterologous second polynucleotide encoding a malate dehydrogenase and a heterologous third polynucleotide encoding a pyruvate carboxylase.

[44] The method of any of paragraphs 1-37, wherein the filamentous fungal host cell comprises a heterologous first polynucleotide encoding a C4 dicarboxylic acid transporter, a heterologous second polynucleotide encoding a malate dehydrogenase, and a heterologous third polynucleotide encoding a pyruvate carboxylase.

[45] The method of any of paragraphs 1-44, wherein the filamentous fungal host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma* cell.

[46] The method of paragraph 45, wherein the host cell is an *Aspergillus* host cell, such as *Aspergillus oryzae.*

[47] The method of any of paragraphs 1-46, wherein the level of the C4 dicarboxylic acid (e.g., malic acid) is increased by at least 25%, e.g., by at least 50%, at least 100%, at least 200%, or at 500% compared to the filamentous fungal host cell without the one or more (several) heterologous polynucleotides encoding the C4 dicarboxylic acid transporter, the malate dehydrogenase, and the pyruvate carboxylase when cultivated under the same conditions.

[48] A method for increasing C4 dicarboxylic acid (e.g., malic acid) production, comprising: (a) transforming into a filamentous fungal host cell one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase, wherein the filamentous fungal host cell secretes (or is capable of secreting) increased levels of the C4 dicarboxylic acid compared to the filamentous fungal host cell without the one or more (several) heterologous polynucleotides encoding the C4 dicarboxylic acid transporter, the malate dehydrogenase, and the pyruvate carboxylase when cultivated under the same conditions; (b) cultivating the transformed filamentous fungal host cell in a medium; and (c) recovering the C4 dicarboxylic acid.

[49] The method of paragraph 48, wherein the C4 dicarboxylic acid transporter is selected from the group consisting of (a) a C4 dicarboxylic acid transporter comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 8, SEQ ID NO: 34, or SEQ ID NO: 36; (b) a C4 dicarboxylic acid transporter encoded by a polynucleotide that hybridizes under at least low stringency conditions, e.g., medium stringency conditions, medium-high stringency conditions, high stringency conditions, or very high stringency conditions with SEQ ID NO: 7, SEQ ID NO: 33, SEQ ID NO: 35 or SEQ ID NO: 37, or a full-length complementary strand thereof; (c) a C4 dicarboxylic acid transporter encoded by a polynucleotide comprising a nucleotide sequence having at least 60% sequence identity, e.g., at least 65%, at least 70%, at least 75%, at least 80%, at least 85%, at least 90%, at least 95%, or 100% sequence identity with SEQ ID NO: 7, SEQ ID NO: 33, SEQ ID NO: 35, or SEQ ID NO: 37; (d) a C4 dicarboxylic acid transporter variant comprising a substitution, deletion, and/or insertion of one or more (several) amino acids of the mature polypeptide of SEQ ID NO: 8, SEQ ID NO: 34, or SEQ ID NO: 36; and (e) a fragment of the C4 dicarboxylic acid transporter of (a), (b), (c), or (d) that has C4 dicarboxylic acid transporter activity.

[50] The method of paragraph 48 or 49, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 8.

[51] The method of any one of paragraphs 48-50, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 34.

[52] The method of any one of paragraphs 48-51, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 36.

[53] The method of any one of paragraphs 48-52, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 7 or the full-length complementary strand thereof.

[54] The method of any one of paragraphs 48-53, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 33, or the full-length complementary strand thereof.

[55] The method of any one of paragraphs 48-54, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 35 or SEQ ID NO: 37, or a full-length complementary strand thereof.

[56] The method of any one of paragraphs 48-55, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 7.

[57] The method of any one of paragraphs 48-56, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 33.

[58] The method of any one of paragraphs 48-57, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 35 or SEQ ID NO: 37.

[59] The method of any one of paragraphs 48-58, wherein the C4 dicarboxylic acid transporter comprises or consists of SEQ ID NO: 8.

[60] The method of any one of paragraphs 48-58, wherein the C4 dicarboxylic acid transporter comprises or consists of SEQ ID NO: 34.

[61] The method of any one of paragraphs 48-58, wherein the C4 dicarboxylic acid transporter comprises or consists of SEQ ID NO: 36.

[62] The method of any of paragraphs 48-61, wherein the heterologous first polynucleotide encoding the C4 dicarboxylic acid transporter is operably linked to a promoter foreign to the first polynucleotide.

[63] The method of any of paragraphs 48-62, wherein the malate dehydrogenase is selected from the group consisting of (a) a malate dehydrogenase comprising an amino acid sequence having at least 60% sequence identity, e.g., at least 65%, at least 70%, at least 75%, at least 80%, at least 85%, at least 90%, at least 95%, or 100% sequence identity with SEQ ID NO: 18 or SEQ ID NO: 20; (b) a malate dehydrogenase encoded by a polynucleotide that hybridizes under at least low stringency conditions, e.g., medium stringency conditions, medium-high stringency conditions, high stringency conditions, or very high stringency conditions with (i) SEQ ID NO: 17 or SEQ ID NO: 19, (ii) the cDNA sequence contained in SEQ ID NO: 17 or SEQ ID NO: 19, or (iii) a full-length complementary strand of (i) or (ii); (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 95%, or 100% sequence identity with SEQ ID NO: 17 or SEQ ID NO: 19; (d) a malate dehydrogenase variant comprising a substitution, deletion, and/or insertion of one or more (several) amino acids of the mature polypeptide of SEQ ID NO: 18 or SEQ ID NO: 20; and (e) a fragment of the malate dehydrogenase of (a), (b), (c), or (d) that has malate dehydrogenase activity.

[64] The method of any of paragraphs 48-63, wherein the malate dehydrogenase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 18.

[65] The method of any of paragraphs 48-64, wherein the malate dehydrogenase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 20.

[66] The method of any of paragraphs 48-65, wherein the malate dehydrogenase is encoded by a polynucleotide that hybridizes under low stringency conditions, medium stringency conditions, medium-high stringency conditions, high stringency conditions, or very high stringency conditions with (i) SEQ ID NO: 17, (ii) the cDNA sequence contained in SEQ ID NO: 17, or (iii) the full-length complementary strand of (i) or (ii).

[67] The method of any of paragraphs 48-66, wherein the malate dehydrogenase is encoded by a polynucleotide that hybridizes under low stringency conditions, medium stringency conditions, medium-high stringency conditions, high stringency conditions, or very high stringency conditions with (i) SEQ ID NO: 19, (ii) the cDNA sequence contained in SEQ ID NO: 19, or (iii) the full-length complementary strand of (i) or (ii).

[68] The method of any of paragraphs 48-67, wherein the malate dehydrogenase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 17.

[69] The method of any of paragraphs 48-68, wherein the malate dehydrogenase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 19.

[70] The method of any of paragraphs 48-69, wherein the malate dehydrogenase comprises or consists of SEQ ID NO: 18.

[71] The method of any of paragraphs 48-69, wherein the malate dehydrogenase comprises or consists of SEQ ID NO: 20.

[72] The method of any of paragraphs 48-62, wherein the malate dehydrogenase is a variant of a parent malate dehydrogenase comprising (i) a deletion at positions equivalent to amino acids positions 2 to 17 or a portion thereof of SEQ ID NO: 18, and (ii) a substitution at a position equivalent to amino acid 48 of SEQ ID NO: 18; wherein the deletion and the substitution reduce mitochondrial import in vivo of the malate dehydrogenase variant thereby increasing the level of the malate dehydrogenase variant in the cytosol, and wherein the filamentous fungal host cell secretes (or is capable of secreting) increased levels of the C4 dicarboxylic acid (e.g., malic acid) compared to the filamentous fungal host cell without the polynucleotide encoding the malate dehydrogenase variant when cultivated under the same conditions.

[73] The method of paragraph 72, wherein the parent malate dehydrogenase is selected from the group consisting of (a) a malate dehydrogenase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 18; (b) a malate dehydrogenase encoded by a polynucleotide that hybridizes under at least low stringency conditions, e.g., medium stringency conditions, medium-high stringency conditions, high stringency conditions, or very high stringency conditions with SEQ ID NO: 17 or its full-length complementary strand; and (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 96%, at least 97%, at least 98%, at least 99%, or 100% sequence identity to SEQ ID NO: 17.

[74] The method of paragraph 73, wherein the parent malate dehydrogenase comprises or consists of SEQ ID NO: 18.

[75] The method of any of paragraphs 72-74, wherein the malate dehydrogenase variant comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to the amino acid sequence of SEQ ID NO: 18.

[76] The method of any of paragraphs 72-75, wherein the variant comprises the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18.

[77] The method of any of paragraphs 48-76, wherein the heterologous second polynucleotide encoding the malate dehydrogenase is operably linked to a promoter foreign to the second polynucleotide.

[78] The method of any of paragraphs 48-77, wherein the pyruvate carboxylase is selected from the group consisting of (a) a pyruvate carboxylase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 27; (b) a pyruvate carboxylase encoded by a polynucleotide that hybridizes under at least low stringency conditions, e.g., medium stringency conditions, medium-high stringency conditions, high stringency conditions, or very high stringency conditions with (i) SEQ ID NO: 26, (ii) the cDNA sequence contained in SEQ ID NO: 26, or (iii) the full-length complementary strand of (i) or (ii); (c) a pyruvate carboxylase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 26; (d) a pyruvate carboxylase variant comprising a substitution, deletion, and/or insertion of one or more (several) amino acids of the mature polypeptide of SEQ ID NO: 27; and (e) a fragment of the pyruvate carboxylase of (a), (b), (c), or (d) that has pyruvate carboxylase activity.

[79] The method of any of paragraphs 48-78, wherein the pyruvate carboxylase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% with SEQ ID NO: 27.

[80] The method of any of paragraphs 48-79, wherein the pyruvate carboxylase is encoded by a polynucleotide that hybridizes under low stringency conditions, medium stringency conditions, medium-high stringency conditions, high stringency conditions, or very high stringency conditions with (i) SEQ ID NO: 26, (ii) the cDNA sequence contained in SEQ ID NO: 26, or (iii) the full-length complementary strand of (i) or (ii).

[81] The method of any of paragraphs 48-80, wherein the pyruvate carboxylase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 26.

[82] The method of any of paragraphs 48-81, wherein the pyruvate carboxylase comprises or consists of SEQ ID NO: 27.

[83] The method of any of paragraphs 48-82, wherein the pyruvate carboxylase is a variant of a mitochondrial pyruvate carboxylase.

[84] The method of any of paragraphs 48-83, wherein the heterologous third polynucleotide encoding the pyruvate carboxylase is operably linked to a promoter foreign to the third polynucleotide.

[85] The method of any of paragraphs 48-84, wherein the filamentous fungal host cell comprises a heterologous first polynucleotide encoding a C4 dicarboxylic acid transporter.

[86] The method of any of paragraphs 48-84, wherein the filamentous fungal host cell comprises a heterologous second polynucleotide encoding a malate dehydrogenase.

[87] The method of any of paragraphs 48-84, wherein the filamentous fungal host cell comprises a heterologous third polynucleotide encoding a pyruvate carboxylase.

[88] The method of any of paragraphs 48-84, wherein the filamentous fungal host cell comprises a heterologous first polynucleotide encoding a C4 dicarboxylic acid transporter and a heterologous second polynucleotide encoding a malate dehydrogenase.

[89] The method of any of paragraphs 48-84, wherein the filamentous fungal host cell comprises a heterologous first polynucleotide encoding a C4 dicarboxylic acid transporter and a heterologous third polynucleotide encoding a pyruvate carboxylase.

[90] The method of any of paragraphs 48-84, wherein the filamentous fungal host cell comprises a heterologous second polynucleotide encoding a malate dehydrogenase and a heterologous third polynucleotide encoding a pyruvate carboxylase.

[91] The method of any of paragraphs 48-84, wherein the filamentous fungal host cell comprises a heterologous first polynucleotide encoding a C4 dicarboxylic acid transporter, a heterologous second polynucleotide encoding a malate dehydrogenase, and a heterologous third polynucleotide encoding a pyruvate carboxylase.

[92] The method of any of paragraphs 48-91, wherein the filamentous fungal host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Rhizopus, Schizophyllum, Talaromyces, Thermoascus, Thielavia, Tolypocladium, Trametes*, and *Trichoderma* cell.

[93] The method of paragraph 92, wherein the host cell is an *Aspergillus* host cell, such as *Aspergillus oryzae*.

[94] The method of any of paragraphs 48-93, wherein the level of the C4 dicarboxylic acid (e.g., malic acid) is increased by at least 25%, e.g., by at least 50%, at least 100%, at least 200%, or at 500% compared to the filamentous fungal host cell without the one or more (several) heterologous polynucleotides encoding the C4 dicarboxylic acid transporter, the malate dehydrogenase, and the pyruvate carboxylase when cultivated under the same conditions.

[95] A filamentous fungal host cell comprising one or more (several) polynucleotides selected from the group consisting of a heterologous first polynucleotide encoding a C4 dicarboxylic acid transporter, a heterologous second polynucleotide encoding a malate dehydrogenase, and a heterologous third polynucleotide encoding a pyruvate carboxylase; wherein the filamentous fungal host cell secretes (or is capable of secreting) increased levels of the C4 dicarboxylic acid (e.g., malic acid) compared to the filamentous fungal host cell without the one or more (several) heterologous polynucleotides encoding the C4 dicarboxylic acid transporter, the malate dehydrogenase, and the pyruvate carboxylase when cultivated under the same conditions.

[96] The filamentous fungal host cell of paragraph 95, wherein the C4 dicarboxylic acid transporter is selected from the group consisting of (a) a C4 dicarboxylic acid transporter comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 8, SEQ ID NO: 34, or SEQ ID NO: 36; (b) a C4 dicarboxylic acid transporter encoded by a polynucleotide that hybridizes under at least low stringency conditions, e.g., medium stringency conditions, medium-high stringency conditions, high stringency conditions, or very high stringency conditions with SEQ ID NO: 7, SEQ ID NO: 33, SEQ ID NO: 35, or SEQ ID NO: 37, or a full-length complementary strand thereof; (c) a C4 dicarboxylic acid transporter encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 7, SEQ ID NO: 33, SEQ ID NO: 35, or SEQ ID NO: 37; (d) a C4 dicarboxylic acid transporter variant comprising a substitution, deletion, and/or insertion of one or more (several) amino acids of the mature polypeptide of SEQ ID NO: 8, SEQ ID NO: 34, or SEQ ID NO: 36; and (e) a fragment of the C4 dicarboxylic acid transporter of (a), (b), (c), or (d) that has C4 dicarboxylic acid transporter activity.

[97] The filamentous fungal host cell of paragraph 95 or 96, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 8.

[98] The filamentous fungal host cell of any one of paragraphs 95-97, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 34.

[99] The filamentous fungal host cell of any one of paragraphs 95-98, wherein the C4 dicarboxylic acid transporter comprises an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 36.

[100] The filamentous fungal host cell of any one of paragraphs 95-99, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 7 or the full-length complementary strand thereof.

[101] The filamentous fungal host cell of any one of paragraphs 95-100, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 33 or the full-length complementary strand thereof.

[102] The filamentous fungal host cell of any one of paragraphs 95-101, wherein the C4 dicarboxylic acid transporter is encoded by a polynucleotide that hybridizes under very low stringency conditions, low stringency conditions, medium stringency conditions, medium-high stringency conditions, high stringency conditions, or very high stringency conditions with SEQ ID NO: 35 or SEQ ID NO: 37, or a full-length complementary strand thereof.

[103] The filamentous fungal host cell of any one of paragraphs 95-102, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 7.

[104] The filamentous fungal host cell of any one of paragraphs 95-103, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 33.

[105] The filamentous fungal host cell of any one of paragraphs 95-104, wherein the C4 dicarboxylic acid transporter is encoded by a polynucleotide comprising a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 35 or SEQ ID NO: 37.

[106] The filamentous fungal host cell of any one of paragraphs 95-105, wherein the C4 dicarboxylic acid transporter comprises or consists of SEQ ID NO: 8.

[107] The filamentous fungal host cell of any one of paragraphs 95-105, wherein the C4 dicarboxylic acid transporter comprises or consists of SEQ ID NO: 34.

[108] The filamentous fungal host cell of any one of paragraphs 95-105, wherein the C4 dicarboxylic acid transporter comprises or consists of SEQ ID NO: 36.

[109] The filamentous fungal host cell of any of paragraphs 95-108, wherein the heterologous first polynucleotide encoding the C4 dicarboxylic acid transporter is operably linked to a promoter foreign to the third polynucleotide.

[110] The filamentous fungal host cell of any of paragraphs 95-109, wherein the malate dehydrogenase is selected from the group consisting of (a) a malate dehydrogenase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 18 or SEQ ID NO: 20; (b) a malate dehydrogenase encoded by a polynucleotide that hybridizes under at least low stringency conditions, e.g., medium stringency conditions, medium-high stringency conditions, high stringency conditions, or very high stringency conditions with (i) SEQ ID NO: 17 or SEQ ID NO: 19, (ii) the cDNA sequence contained in SEQ ID NO: 17 or SEQ ID NO: 19, or (iii) a full-length complementary strand of (i) or (ii); (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 17 or SEQ ID NO: 19; (d) a malate dehydrogenase variant comprising a substitution, deletion, and/or insertion of one or more (several) amino acids of the mature polypeptide of SEQ ID NO: 18 or SEQ ID NO: 20; and (e) a fragment of the malate dehydrogenase of (a), (b), (c), or (d) that has malate dehydrogenase activity.

[111] The filamentous fungal host cell of any of paragraphs 95-110, wherein the malate dehydrogenase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 18.

[112] The filamentous fungal host cell of any of paragraphs 95-111, wherein the malate dehydrogenase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 20.

[113] The filamentous fungal host cell of any of paragraphs 95-112, wherein the malate dehydrogenase is encoded by a polynucleotide that hybridizes under low stringency conditions, medium stringency conditions, medium-high stringency conditions, high stringency conditions, or very high stringency conditions with (i) SEQ ID NO: 17, (ii) the cDNA sequence contained in SEQ ID NO: 17, or (iii) the full-length complementary strand of (i) or (ii).

[114] The filamentous fungal host cell of any of paragraphs 95-113, wherein the malate dehydrogenase is encoded by a polynucleotide that hybridizes under low stringency conditions, medium stringency conditions, medium-high stringency conditions, high stringency conditions, or very high stringency conditions with (i) SEQ ID NO: 19, (ii) the cDNA sequence contained in SEQ ID NO: 19, or (iii) the full-length complementary strand of (i) or (ii).

[115] The filamentous fungal host cell of any of paragraphs 95-114, wherein the malate dehydrogenase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 17.

[116] The filamentous fungal host cell of any of paragraphs 95-115, wherein the malate dehydrogenase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 19.

[117] The filamentous fungal host cell of any of paragraphs 95-116, wherein the malate dehydrogenase comprises or consists of SEQ ID NO: 18.

[118] The filamentous fungal host cell of any of paragraphs 95-116, wherein the malate dehydrogenase comprises or consists of SEQ ID NO: 20.

[119] The filamentous fungal host cell of any of paragraphs 95-109, wherein the malate dehydrogenase is a variant of a parent malate dehydrogenase comprising (i) a deletion at positions equivalent to amino acids positions 2 to 17 or a portion thereof of SEQ ID NO: 18, and (ii) a substitution at a position equivalent to amino acid 48 of SEQ ID NO: 18; wherein the deletion and the substitution reduce mitochondrial import in vivo of the malate dehydrogenase variant thereby increasing the level of the malate dehydrogenase variant in the cytosol, and wherein the filamentous fungal host cell secretes (or is capable of secreting) increased levels of the C4 dicarboxylic acid (e.g., malic acid) compared to the filamentous fungal host cell without the polynucleotide encoding the malate dehydrogenase variant when cultivated under the same conditions.

[120] The filamentous fungal host cell of paragraph 119, wherein the parent malate dehydrogenase is selected from the group consisting of (a) a malate dehydrogenase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 18; (b) a malate dehydrogenase encoded by a polynucleotide that hybridizes under at least low stringency conditions, e.g., medium stringency conditions, medium-high stringency conditions, high stringency conditions, or very high stringency conditions with SEQ ID NO: 17, or its full-length complementary strand; and (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 17.

[121] The filamentous fungal host cell of paragraph 120, wherein the parent malate dehydrogenase comprises or consists of SEQ ID NO: 18.

[122] The filamentous fungal host cell of any of paragraphs 119-121, wherein the malate dehydrogenase variant comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to the amino acid sequence of SEQ ID NO: 18.

[123] The filamentous fungal host cell of any of paragraphs 119-122, wherein the variant comprises the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18.

[124] The filamentous fungal host cell of any of paragraphs 119-123, wherein the heterologous second polynucleotide encoding the malate dehydrogenase is operably linked to a promoter foreign to the first polynucleotide.

[125] The filamentous fungal host cell of any of paragraphs 95-124, wherein the pyruvate carboxylase is selected from the group consisting of (a) a pyruvate carboxylase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 27; (b) a pyruvate carboxylase encoded by a polynucleotide that hybridizes under at least low stringency conditions, e.g., medium stringency conditions, medium-high stringency conditions, high stringency conditions, or very high stringency conditions with (i) SEQ ID NO: 26, (ii) the cDNA sequence contained in SEQ ID NO: 26, or (iii) the full-length complementary strand of (i) or (ii); (c) a pyruvate carboxylase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 26; (d) a pyruvate carboxylase variant comprising a substitution, deletion, and/or insertion of one or more (several) amino acids of the mature polypeptide of SEQ ID NO: 27; and (e) a fragment of the pyruvate carboxylase of (a), (b), (c), or (d) that has pyruvate carboxylase activity.

[126] The filamentous fungal host cell of any of paragraphs 95-125, wherein the pyruvate carboxylase comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% with SEQ ID NO: 27.

[127] The filamentous fungal host cell of any of paragraphs 95-126, wherein the pyruvate carboxylase is encoded by a polynucleotide that hybridizes under low stringency conditions, medium stringency conditions, medium-high stringency conditions, high stringency conditions, or very high stringency conditions with (i) SEQ ID NO: 26, (ii) the cDNA sequence contained in SEQ ID NO: 26, or (iii) the full-length complementary strand of (i) or (ii).

[128] The filamentous fungal host cell of any of paragraphs 95-127, wherein the pyruvate carboxylase is encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity with SEQ ID NO: 26.

[129] The filamentous fungal host cell of any of paragraphs 95-128, wherein the pyruvate carboxylase comprises or consists of SEQ ID NO: 27.

[130] The filamentous fungal host cell of any of paragraphs 95-129, wherein the pyruvate carboxylase is a variant of a mitochondrial pyruvate carboxylase.

[131] The filamentous fungal host cell of any of paragraphs 95-130, wherein the heterologous third polynucleotide encoding the pyruvate carboxylase is operably linked to a promoter foreign to the second polynucleotide.

[132] The filamentous fungal host cell of any of paragraphs 95-131, which comprises a heterologous first polynucleotide encoding a C4 dicarboxylic acid transporter.

[133] The filamentous fungal host cell of any of paragraphs 95-131, which comprises a heterologous second polynucleotide encoding a malate dehydrogenase.

[134] The filamentous fungal host cell of any of paragraphs 95-131, which comprises a heterologous third polynucleotide encoding a pyruvate carboxylase.

[135] The filamentous fungal host cell of any of paragraphs 95-131, which comprises a heterologous first polynucleotide encoding a C4 dicarboxylic acid transporter and a heterologous second polynucleotide encoding a malate dehydrogenase.

[136] The filamentous fungal host cell of any of paragraphs 95-131, which comprises a heterologous first polynucleotide encoding a C4 dicarboxylic acid transporter and a heterologous third polynucleotide encoding a pyruvate carboxylase.

[137] The filamentous fungal host cell of any of paragraphs 95-131, which comprises a heterologous second polynucleotide encoding a malate dehydrogenase and a heterologous third polynucleotide encoding a pyruvate carboxylase.

[138] The filamentous fungal host cell of any of paragraphs 95-131, which comprises a heterologous first polynucleotide encoding a C4 dicarboxylic acid transporter, a heterologous second polynucleotide encoding a malate dehydrogenase, and a heterologous third polynucleotide encoding a pyruvate carboxylase.

[139] The filamentous fungal host cell of any of paragraphs 95-138, which is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Rhizopus, Schizophyllum, Talaromyces, Thermoascus, Thielavia, Tolypocladium, Trametes*, and *Trichoderma* cell.

[140] The filamentous fungal host cell of paragraph 139, wherein the host cell is an *Aspergillus* host cell, such as *Aspergillus oryzae*.

[141] The filamentous fungal host cell of any of paragraphs 95-140, wherein the level of the C4 dicarboxylic acid (e.g., malic acid) is increased by at least 25%, e.g., by at least 50%, at least 100%, at least 200%, or at 500% compared to the filamentous fungal host cell without the one or more (several) heterologous polynucleotides encoding the C4 dicarboxylic acid transporter, the malate dehydrogenase, and the pyruvate carboxylase when cultivated under the same conditions.

[142] An isolated variant of a parent malate dehydrogenase, comprising (i) a deletion at positions equivalent to amino acids positions 2 to 17 or a portion thereof of SEQ ID NO: 18, and (ii) a substitution at a position equivalent to amino acid 48 of SEQ ID NO: 18.

[143] The variant of paragraph 142, wherein the parent malate dehydrogenase is (a) a malate dehydrogenase comprising an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 18; or (b) a malate dehydrogenase encoded by a polynucleotide that hybridizes under at least low stringency conditions, e.g., medium stringency conditions, medium-high stringency conditions, high stringency conditions, or very high stringency conditions with SEQ ID NO: 17 or its full-length complementary strand; or (c) a malate dehydrogenase encoded by a polynucleotide comprising a nucleotide sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 17.

[144] The variant of paragraph 142, wherein the parent malate dehydrogenase comprises or consists of SEQ ID NO: 18.

[145] The variant of any of paragraphs 142-144, which comprises an amino acid sequence having at least 60% sequence identity, e.g., at least 65%, at least 70%, at least 75%, at least 80%, at least 85%, at least 90%, at least 95%, at least 96%, at least 97%, at least 98%, at least 99%, or 100% sequence identity to the amino acid sequence of the parent malate dehydrogenase.

[145] The variant of any of paragraphs 142-145, which comprises the deletions Phe2*+Ala3*+Ala4*+Arg5*+Gln6*+Ser7*+Phe8*. Asn9*+Leu10*+Leu11*+Gln12*+Lys13*+Arg14*+Ala15*+Phe16*+Ser17* of SEQ ID NO: 18 and the substitution Arg48Tyr of SEQ ID NO: 18.

[146] An isolated polynucleotide encoding the variant of any of paragraphs 142-146.

[147] A nucleic acid construct comprising the polynucleotide of paragraph 147.

[148] A recombinant expression vector comprising the polynucleotide of paragraph 147.

[149] A recombinant host cell comprising the polynucleotide of paragraph 147.

[150] The method of any one of paragraphs 1-94, wherein the C4 dicarboxylic acid is malic acid.

[151] The filamentous fungal host cell of any of paragraphs 95-140, wherein the C4 dicarboxylic acid is malic acid.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An *Aspergillus oryzae* host cell comprising a heterologous polynucleotide encoding a malic acid transporter, wherein the malic acid transporter is selected from the group consisting of:
  (a) a malic acid transporter comprising an amino acid sequence having at least 95% sequence identity with SEQ ID NO: 8;
  (b) a malic acid transporter encoded by a polynucleotide that hybridizes under very high stringency conditions with the full-length complementary strand to SEQ ID NO: 7; and
  (c) a malic acid transporter encoded by a polynucleotide comprising a nucleotide sequence having at least 95% sequence identity with SEQ ID NO: 7;
  and wherein the host cell is capable of secreting at least 50% more malic acid compared to the host cell without the heterologous polynucleotide encoding the malic acid transporter when cultivated under the same conditions.

2. The host cell of claim 1, wherein the malic acid transporter comprises or consists of SEQ ID NO: 8.

3. The host cell of claim 1, wherein the heterologous polynucleotide encoding the malic acid transporter is operably linked to a promoter foreign to the polynucleotide encoding the malic acid transporter.

4. The host cell of claim 1, further comprising a heterologous polynucleotide encoding a malate dehydrogenase.

5. The host cell of claim 4, wherein the malate dehydrogenase comprises or consists of SEQ ID NO: 18 or SEQ ID NO: 20.

6. The host cell of claim 1, wherein the host cell further comprises a heterologous polynucleotide encoding a pyruvate carboxylase.

7. The host cell of claim 6, wherein the pyruvate carboxylase comprises or consists of SEQ ID NO: 27.

8. The host cell of claim 1, wherein host cell is capable of secreting at least 75% more malic acid compared to the host cell without the polynucleotide encoding the malic acid transporter when cultivated under the same conditions.

9. A method of producing malic acid, comprising:
  (a) cultivating the host cell of claim 1 in a medium; and
  (b) recovering the malic acid.

10. The host cell of claim 1, wherein the malic acid transporter comprises an amino acid sequence having at least 97% sequence identity with SEQ ID NO: 8.

11. The host cell of claim 1, wherein the malic acid transporter comprises an amino acid sequence having at least 98% sequence identity with SEQ ID NO: 8.

12. The host cell of claim 1, wherein the malic acid transporter comprises an amino acid sequence having at least 99% sequence identity with SEQ ID NO: 8.

13. The host cell of claim 1, wherein the malic acid transporter is encoded by a polynucleotide that hybridizes under very high stringency conditions with the full-length complementary strand to SEQ ID NO: 7.

14. The host cell of claim 1, wherein the malic acid transporter is encoded by a polynucleotide comprising a nucleotide sequence having at least 97% sequence identity with SEQ ID NO: 7.

15. The host cell of claim 1, wherein the malic acid transporter is encoded by a polynucleotide comprising a nucleotide sequence having at least 98% sequence identity with SEQ ID NO: 7.

16. The host cell of claim 1, wherein the malic acid transporter is encoded by a polynucleotide comprising a nucleotide sequence having at least 99% sequence identity with SEQ ID NO: 7.

17. The host cell of claim 1, wherein the malic acid transporter comprises an amino acid sequence having at least 95% sequence identity with SEQ ID NO: 8.

18. The host cell of claim 1, wherein the malic acid transporter is encoded by a polynucleotide comprising a nucleotide sequence having at least 95% sequence identity with SEQ ID NO: 7.

19. The host cell of claim 1, wherein the host cell is capable of producing malic acid at a level greater than 120 g/L.

20. An *Aspergillus oryzae* host cell comprising a heterologous polynucleotide encoding a malic acid transporter, wherein the malic acid transporter differs by no more than ten amino acids from SEQ ID NO: 8;
  and wherein the host cell is capable of secreting more malic acid compared to the host cell without the heterologous polynucleotide encoding the malic acid transporter when cultivated under the same conditions.

21. The host cell of claim 20, wherein the malic acid transporter differs by no more than ten conservative substitutions from SEQ ID NO: 8.

22. The host cell of claim 20, wherein the cell is capable of secreting at least 50% more malic acid compared to the host cell without the heterologous polynucleotide encoding the malic acid transporter when cultivated under the same conditions.

23. The host cell of claim 20, wherein the malic acid transporter differs by no more than five amino acids from SEQ ID NO: 8.

24. The host cell of claim 20, wherein the malic acid transporter differs by no more than five conservative substitutions from SEQ ID NO: 8.

25. The host cell of claim 20, wherein the malic acid transporter differs by no more than three amino acids from SEQ ID NO: 8.

26. The host cell of claim 20, wherein the malic acid transporter differs by no more than three conservative substitutions from SEQ ID NO: 8.

27. The host cell of claim 20, wherein the malic acid transporter differs by no more than two amino acids from SEQ ID NO: 8.

28. The host cell of claim 20, wherein the malic acid transporter differs by no more than two conservative substitutions from SEQ ID NO: 8.

29. The host cell of claim 20, wherein the malic acid transporter differs by no more than one amino acid from SEQ ID NO: 8.

30. The host cell of claim 20, wherein the malic acid transporter differs by no more than one conservative substitution from SEQ ID NO: 8.

31. The host cell of claim 30, wherein the cell is capable of secreting at least 50% more malic acid compared to the host cell without the heterologous polynucleotide encoding the malic acid transporter when cultivated under the same conditions.

* * * * *